(12) United States Patent
Kun et al.

(10) Patent No.: US 8,377,985 B2
(45) Date of Patent: Feb. 19, 2013

(54) TREATMENT OF CANCER

(75) Inventors: Ernest Kun, Mill Valley, CA (US); Jerome Mendeleyev, San Francisco, CA (US); Carol Basbaum, San Francisco, CA (US); Hassan Lemjabbar-Alaoui, Danville, CA (US); Valeria S. Ossovskaya, San Francisco, CA (US)

(73) Assignee: BiPar Sciences, Inc., Bridgewater, NJ (US)

( * ) Notice: Subject to any disclaimer, the term of this patent is extended or adjusted under 35 U.S.C. 154(b) by 171 days.

(21) Appl. No.: 12/165,437

(22) Filed: Jun. 30, 2008

(65) Prior Publication Data

US 2008/0319054 A1    Dec. 25, 2008

Related U.S. Application Data

(63) Continuation of application No. 11/458,379, filed on Jul. 18, 2006, now Pat. No. 7,405,227.

(60) Provisional application No. 60/700,446, filed on Jul. 18, 2005.

(51) Int. Cl.
*A61K 31/47* (2006.01)
*A61K 31/165* (2006.01)
*A61K 31/195* (2006.01)

(52) U.S. Cl. .................. 514/457; 514/619; 514/562

(58) Field of Classification Search .............. 514/457, 514/619, 562
See application file for complete search history.

(56) References Cited

U.S. PATENT DOCUMENTS

| | | | |
|---|---|---|---|
| 2,006,735 A | 7/1935 | Fischer at al. |
| 2,937,204 A | 5/1950 | Harris at al. |
| 2,669,583 A | 2/1954 | Clinton at al. |
| 3,161,564 A | 12/1964 | Morehouse |
| 3,228,833 A | 1/1966 | Crounse at al. |
| 4,536,516 A | 8/1985 | Harper et al. |
| 4,604,463 A | 8/1986 | Miyasaka et al. |
| 4,808,614 A | 2/1989 | Hertel |
| 4,923,885 A | 5/1990 | Hupe et al. |
| 5,032,617 A | 7/1991 | Lee et al. |
| 5,041,653 A | 8/1991 | Lee et al. |
| 5,162,532 A | 11/1992 | Comins et al. |
| 5,177,075 A | 1/1993 | Sato et al. |
| 5,191,082 A | 3/1993 | Comins et al. |
| 5,200,524 A | 4/1993 | Comins et al. |
| 5,215,738 A | 6/1993 | Lee et al. |
| 5,223,608 A | 6/1993 | Chou et al. |
| 5,232,735 A | 8/1993 | Kurtz et al. |
| 5,243,050 A | 9/1993 | Comins et al. |
| 5,247,089 A | 9/1993 | Comins et al. |
| 5,262,564 A | 11/1993 | Kun et al. |
| 5,283,352 A | 2/1994 | Backström et al. |
| 5,321,140 A | 6/1994 | Comins et al. |
| 5,420,319 A | 5/1995 | Okamoto et al. |
| 5,434,254 A | 7/1995 | Chou et al. |
| 5,464,871 A | 11/1995 | Kun et al. |
| 5,472,949 A | 12/1995 | Arasaki et al. |
| 5,473,074 A | 12/1995 | Kun et al. |
| 5,482,833 A | 1/1996 | Pero et al. |
| 5,482,975 A | 1/1996 | Kun et al. |
| 5,484,951 A | 1/1996 | Kun et al. |
| 5,516,941 A | 5/1996 | Kun et al. |
| 5,519,053 A | 5/1996 | Kun et al. |
| 5,583,155 A | 12/1996 | Kun et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,633,282 A | 5/1997 | Collins et al. |
| 5,637,618 A | 6/1997 | Kurtz et al. |

(Continued)

FOREIGN PATENT DOCUMENTS

| CN | 1768732 A | 5/2006 |
|---|---|---|
| CN | 1768733 | 5/2006 |

(Continued)

OTHER PUBLICATIONS

Goodman and Gilman the pharmacological Basis of Therapeutic $9^{th}$ Edition pp. (1996) 1225-1232, 1269-1271.*

(Continued)

*Primary Examiner* — Shirley V Gembeh
(74) *Attorney, Agent, or Firm* — Morrison & Foerster LLP

(57) ABSTRACT

Methods of treating bone cancer are disclosed. The methods comprise administering to a patient a therapeutically effective amount of a compound of formula (Ia)

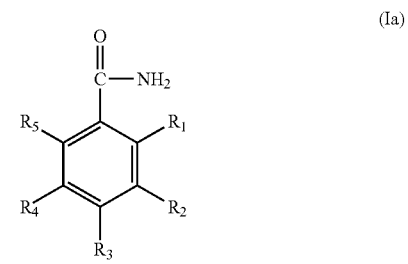

wherein $R_1$, $R_2$, $R_3$, $R_4$, and $R_5$ are described herein, wherein at least two of the five $R_1$, $R_2$, $R_3$, $R_4$, and $R_5$ substituents are always hydrogen, at least one of the five substituents is always nitro, and at least one substituent positioned adjacent to a nitro is always iodo, and pharmaceutically acceptable salts thereof.

9 Claims, 18 Drawing Sheets

U.S. PATENT DOCUMENTS

| | | | |
|---|---|---|---|
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,652,260 A | 7/1997 | Kun et al. |
| 5,652,367 A | 7/1997 | Kun et al. |
| 5,654,311 A | 8/1997 | Kurtz et al. |
| 5,665,755 A | 9/1997 | Kurtz et al. |
| 5,670,518 A | 9/1997 | Kun et al. |
| 5,700,792 A | 12/1997 | Kurtz et al. |
| 5,703,053 A | 12/1997 | Kurtz et al. |
| 5,719,151 A | 2/1998 | Shall et al. |
| 5,734,056 A | 3/1998 | Burk et al. |
| 5,736,576 A | 4/1998 | Kun et al. |
| 5,753,674 A | 5/1998 | Kun et al. |
| 5,756,510 A | 5/1998 | Griffin et al. |
| 5,770,599 A | 6/1998 | Gibson |
| 5,783,599 A | 7/1998 | Kun et al. |
| 5,837,729 A | 11/1998 | Bourinbaiar |
| 5,866,608 A | 2/1999 | Kurtz et al. |
| 5,874,444 A | 2/1999 | West et al. |
| 5,877,185 A | 3/1999 | Kun et al. |
| 5,908,861 A | 6/1999 | Kun |
| 5,922,775 A | 7/1999 | Kun et al. |
| 5,959,133 A | 9/1999 | Ohnishi |
| 5,981,575 A | 11/1999 | Kuhajda et al. |
| 6,004,978 A | 12/1999 | Kun et al. |
| 6,008,250 A | 12/1999 | Kurtz et al. |
| 6,015,792 A | 1/2000 | Kurtz et al. |
| 6,015,827 A | 1/2000 | Griffin et al. |
| 6,017,958 A | 1/2000 | Kun et al. |
| 6,100,283 A | 8/2000 | Griffin et al. |
| 6,121,278 A | 9/2000 | Jackson et al. |
| 6,156,739 A | 12/2000 | Griffin et al. |
| 6,169,104 B1 | 1/2001 | Tusé et al. |
| 6,201,020 B1 | 3/2001 | Zhang et al. |
| 6,235,748 B1 | 5/2001 | Li et al. |
| 6,277,990 B1 | 8/2001 | Jagtap et al. |
| 6,303,629 B1 | 10/2001 | Kun |
| 6,310,082 B1 | 10/2001 | Griffin et al. |
| 6,316,455 B1 | 11/2001 | Griffin et al. |
| 6,316,495 B1 | 11/2001 | Kun et al. |
| 6,326,517 B1 | 12/2001 | Kume et al. |
| 6,380,193 B1 | 4/2002 | Li et al. |
| 6,387,902 B1 | 5/2002 | Zhang et al. |
| 6,395,749 B1 | 5/2002 | Li et al. |
| 6,407,079 B1 | 6/2002 | Müller et al. |
| 6,423,696 B1 | 7/2002 | Collins et al. |
| 6,426,415 B1 | 7/2002 | Jackson et al. |
| 6,448,271 B1 | 9/2002 | Lubisch et al. |
| 6,476,048 B1 | 11/2002 | Szabo et al. |
| 6,495,541 B1 | 12/2002 | Webber et al. |
| 6,514,983 B1 | 2/2003 | Li et al. |
| 6,531,491 B1 | 3/2003 | Kania et al. |
| 6,548,494 B1 | 4/2003 | Webber et al. |
| 6,653,316 B1 | 11/2003 | South et al. |
| 6,664,269 B2 | 12/2003 | Martin et al. |
| 6,677,333 B1 | 1/2004 | Seko et al. |
| 6,723,733 B2 | 4/2004 | Li et al. |
| 6,903,098 B1 | 6/2005 | Lubisch et al. |
| 6,924,284 B2 | 8/2005 | Beaton et al. |
| 6,989,388 B2 | 1/2006 | Pellicciari et al. |
| 7,179,484 B2 | 2/2007 | Singh |
| RE39,608 E | 5/2007 | Lubisch et |
| 7,405,227 B2 | 7/2008 | Kun et al. |
| 7,538,252 B2 | 5/2009 | Ossovskaya et al. |
| 7,994,222 B2 | 8/2011 | Ossovskaya et al. |
| 2002/0028815 A1 | 3/2002 | Ator et al. |
| 2002/0142334 A1 | 10/2002 | Brown et al. |
| 2002/0156050 A1 | 10/2002 | Li et al. |
| 2002/0164633 A1 | 11/2002 | Szabo et al. |
| 2004/0034078 A1 | 2/2004 | Skalitzky et al. |
| 2004/0077667 A1 | 4/2004 | Matsuoka et al. |
| 2004/0198693 A1 | 10/2004 | DeNinno et al. |
| 2004/0248879 A1 | 12/2004 | Canan-Koch et al. |
| 2004/0249841 A1 | 12/2004 | Cameron et al. |
| 2005/0004038 A1 | 1/2005 | Lyon et al. |
| 2005/0020595 A1 | 1/2005 | Kalish et al. |
| 2005/0026933 A1 | 2/2005 | Greenberger et al. |
| 2005/0054631 A1 | 3/2005 | Jiang et al. |
| 2005/0059824 A1 | 3/2005 | Vaidyanathan et al. |
| 2005/0080096 A1 | 4/2005 | Ishida et al. |
| 2005/0113283 A1 | 5/2005 | Solow-Cordero et al. |
| 2005/0142621 A1 | 6/2005 | Thompson et al. |
| 2005/0143370 A1 | 6/2005 | Helleday et al. |
| 2005/0171036 A1 | 8/2005 | Arakawa et al. |
| 2005/0171101 A1 | 8/2005 | Yamamoto et al. |
| 2005/0182040 A1 | 8/2005 | Imazaki et al. |
| 2005/0227919 A1 | 10/2005 | Ashworth et al. |
| 2005/0287120 A1 | 12/2005 | Fisher et al. |
| 2006/0063767 A1 | 3/2006 | Javaid et al. |
| 2006/0074073 A1 | 4/2006 | Steinfeldt et al. |
| 2006/0084650 A1 | 4/2006 | Doug et al. |
| 2006/0094676 A1 | 5/2006 | Lahav et al. |
| 2006/0100198 A1 | 5/2006 | Liu et al. |
| 2006/0204981 A1 | 9/2006 | Li et al. |
| 2006/0229289 A1 | 10/2006 | Zhu et al. |
| 2006/0229351 A1 | 10/2006 | Zhu et al. |
| 2007/0015814 A1 | 1/2007 | Kun et al. |
| 2007/0015837 A1 | 1/2007 | Kun et al. |
| 2007/0265324 A1 | 11/2007 | Wernet et al. |
| 2007/0281948 A1 | 12/2007 | Peukert et al. |
| 2007/0292883 A1 | 12/2007 | Ossovskaya et al. |
| 2008/0025990 A1 | 1/2008 | Ludwig |
| 2008/0039633 A1 | 2/2008 | Jung et al. |
| 2008/0076737 A1 | 3/2008 | Ossovskaya et al. |
| 2008/0076778 A1 | 3/2008 | Ossovskaya et al. |
| 2008/0103104 A1 | 5/2008 | Moore et al. |
| 2008/0103208 A1 | 5/2008 | Ossovskaya et al. |
| 2008/0167345 A1 | 7/2008 | Jones et al. |
| 2008/0171786 A1 | 7/2008 | Brugemeier et al. |
| 2008/0176946 A1 | 7/2008 | Ossovskaya et al. |
| 2008/0262062 A1 | 10/2008 | Ossovskaya et al. |
| 2008/0293795 A1 | 11/2008 | Donawho et al. |
| 2009/0076122 A1 | 3/2009 | Kun et al. |
| 2009/0123419 A1 | 5/2009 | Sherman et al. |
| 2009/0131529 A1 | 5/2009 | Sherman et al. |
| 2009/0149397 A1 | 6/2009 | Ossovskaya et al. |
| 2009/0149417 A1 | 6/2009 | Ossovskaya et al. |
| 2009/0275608 A1 | 11/2009 | Ossovskaya et al. |
| 2009/0291924 A1 | 11/2009 | Ossovskaya et al. |

FOREIGN PATENT DOCUMENTS

| | | |
|---|---|---|
| CN | 1768733 A | 5/2006 |
| CN | 101190211 A | 6/2008 |
| DE | 10 2005 023 834 A1 | 5/2006 |
| EP | 0 602 454 B1 | 4/1996 |
| EP | 0 841 924 B1 | 5/1998 |
| EP | 1 127 052 B1 | 8/2001 |
| EP | 1348432 A1 | 10/2003 |
| EP | 1 500 643 A1 | 1/2005 |
| EP | 1 082 416 B1 | 3/2007 |
| FR | 2456731 | 12/1980 |
| GB | 1 013 907 A | 12/1965 |
| GB | 1 064 629 A | 4/1967 |
| GB | 1 463 575 | 2/1977 |
| GB | 2 136 425 A | 9/1984 |
| GB | 2 447 796 B | 3/2009 |
| JP | 2000191612 | 7/2000 |
| JP | 2005336083 | 12/2005 |
| WO | WO-91/18591 A1 | 12/1991 |
| WO | WO-92/06687 A1 | 4/1992 |
| WO | WO-94/05664 A1 | 3/1994 |
| WO | WO-94/10202 A1 | 5/1994 |
| WO | WO 94/26730 A2 | 11/1994 |
| WO | WO 94/27584 A2 | 12/1994 |
| WO | WO 94/26730 A3 | 1/1995 |
| WO | WO 94/27584 A3 | 5/1995 |
| WO | WO 96/22791 A1 | 8/1996 |

| | | |
|---|---|---|
| WO | WO-96/40210 A1 | 12/1996 |
| WO | WO 97/34593 A1 | 9/1997 |
| WO | WO 98/45253 A1 | 10/1998 |
| WO | WO-98/51307 A1 | 11/1998 |
| WO | WO-99/11624 A1 | 3/1999 |
| WO | WO-99/11628 A1 | 3/1999 |
| WO | WO 01/04086 A1 | 1/2001 |
| WO | WO 02/49992 A2 | 6/2002 |
| WO | WO 02/049992 A3 | 9/2002 |
| WO | WO 03/007955 A2 | 1/2003 |
| WO | WO 03/007955 A3 | 5/2003 |
| WO | WO-03/062392 A2 | 7/2003 |
| WO | WO-03/062392 A3 | 7/2003 |
| WO | WO-2005/012305 A2 | 2/2005 |
| WO | WO-2005/012305 A3 | 2/2005 |
| WO | WO-2005/054201 A1 | 6/2005 |
| WO | WO-2005/054209 A1 | 6/2005 |
| WO | WO-2005/054210 A1 | 6/2005 |
| WO | WO-2005/058843 A1 | 6/2005 |
| WO | WO-2005/097750 A1 | 10/2005 |
| WO | WO-2006/003146 A1 | 1/2006 |
| WO | WO-2006/003147 A1 | 1/2006 |
| WO | WO-2006/003148 A1 | 1/2006 |
| WO | WO-2006/003150 A1 | 1/2006 |
| WO | WO-2006/020681 A2 | 2/2006 |
| WO | WO-2006/020681 A3 | 2/2006 |
| WO | WO-2006/033006 A2 | 3/2006 |
| WO | WO-2006/033006 A3 | 3/2006 |
| WO | WO-2006/046735 A1 | 5/2006 |
| WO | WO-2006/067472 A1 | 6/2006 |
| WO | WO 2007/011962 A2 | 1/2007 |
| WO | WO-2007/084532 A2 | 7/2007 |
| WO | WO-2007/084532 A3 | 7/2007 |
| WO | WO-2007/107305 A2 | 9/2007 |
| WO | WO-2007/107305 A3 | 9/2007 |
| WO | WO 2007/011962 A3 | 12/2007 |
| WO | WO 2008/030883 A2 | 3/2008 |
| WO | WO-2008/030891 A2 | 3/2008 |
| WO | WO-2008/030891 A3 | 3/2008 |
| WO | WO-2008/089272 A1 | 7/2008 |
| WO | WO-2008/107478 A1 | 9/2008 |
| WO | WO-2008/147418 A1 | 12/2008 |
| WO | WO-2009/064444 A2 | 5/2009 |
| WO | WO-2009/064738 A2 | 5/2009 |
| WO | WO-2009/073869 A1 | 6/2009 |
| WO | WO-2009/100159 A2 | 8/2009 |
| WO | WO-2009/100159 A3 | 8/2009 |
| WO | WO-2010/091140 A1 | 8/2010 |

OTHER PUBLICATIONS

Aachmann, F. L. et al. (2003). "Structural Background of Cyclodextrin-Protein Interactions," *Prot. Eng.* 16(12):905-912.

Arnold, N. et al. (May 1996). "Overrepresentation of 3q and 8q Material and Loss of 18q Material Are Recurrent Findings in Advanced Human Ovarian Cancer," *Genes Chromosomes Cancer* 16(1):46-54.

Arnone, C. et al. (Apr. 18, 1997). Nucleophilic Substitution Reactions of 1-Halogeno-4-COR-2- Nitrobenzenes and 1-Halogen-6-COR-2 Nitrobenzenes with Sodium Benzenethiolate and Piperidine. Can an Inverted Built-In Solvation be Responsible for the Peculiar Activation by an *o*-Carboxamido Group in $S_nAr$ Reactions With an Anionic Nucleophile? *J. Org. Chem.* 62(10):3093-3097.

Audebert, M. et al. (Dec. 31, 2004)."Involvement of Poly(ADP-Ribose) Polymerase-1 and XRCC1/DNA Ligase III in an Alternative Route for DNA Double-Strand Breaks Rejoining," *J. Biol. Chem.* 279(53):55117-55126. Epub Oct. 21, 2004.

Ayhan, A. et al. (2006). "Topotecan as a Second-Line Therapy in Patients With Ovarian and Primary Peritoneal Cancer: Initial Response and Long-Term Follow-Up," *Eur. J. Gynaecol Oncol.* 27(6):603-606.

Bale, A. E. et al. (1997). "The Nevoid Basal Cell Carcinoma Syndrome: Genetics and Mechanism of Carcinogenesis," *Cancer Invest.* 15(2):180-186.

Ball, H. G. et al. (Aug. 1996). "A Phase II Trial of Paclitaxel in Patients With Advanced or Recurrent Adenocarcinoma of the Endometrium: A Gynecologic Oncology Group Study," *Gynecologic Oncology* 62(2):278-281.

Banasik, M. et al. (Jan. 25, 1992). "Specific Inhibitors of Poly(ADP-Ribose) Synthetase and Mono(ADP-Ribosyl)Transferase," *J. Biol. Chem.* 267(3):1569-1575.

Bauer, P. I. et al. (2002). "Anti-Cancer Action of 4-lodo-3-Introbenzamide in Combination With Buthionine Sulfoximine: Inactivation of Poly(ADP-Ribose) Polymerase and Tumor Glycolysis and the Appearance of a Poly(ADP-Ribose) Polymerase Protease," *Biochem. Pharmacol.* 63(3):455-462.

Bauer, P. I. et al. (2005). "The Influence of ATP on Poly(ADP-Ribose) Metabolism," *Int'l J. Mol. Med.* 16:321-324.

Bello, M. J. et al. (Jan. 15, 1990). "Chromosome Aberrations in Metastatic Ovarian Cancer: Relationship with Abnormalities in Primary Tumors," *Int. J. Cancer* 45(1):50-54.

Ben-Hur, E. et al. (1984). "Inhibitors of Poly (ADP-Ribose) Synthesis Enhance Radiation Response by Differentially Affecting Repair of Potentially Lethal Versus Sublethal Damage," *British Journal of Cancer* 49(Suppl. 6):34-42.

Bentle, M. S. et al. (2006). "New Tricks for Old Drugs: the Anticarcinogenic Potential of DNA Repair Inhibitors," *J. Mol. Histol.* 37(5-7):203-218.

Berchuck, A. et al. (Jan. 1991). "Overexpression of HER-2/Neu in Endometrial Cancer is Associated With Advanced Stage Disease," *Am. J. Obstet. Gynecol.* 164(1 Pt. 1):15-21.

Berger, N. A. (Jan. 1985). "Poly(ADP-Ribose) in the Cellular Response to DNA Damage," *Radiation Research* 101(1):4-15.

Berkow, R. ed., (Aug. 1987). "Chapter 105. Oncology—Treatment and Prognosis," in *The Merck Manual of Diagnosis and Therapy*, 15th ed. Merck & Co., Inc., pp. 1218-1225 and Table of Contents.

Bhattacharjee, A. et al. (Nov. 20, 2001). "Classification of Human Lung Carcinomas by mRNA Expression Profiling Reveals Distinct Adenocarcinoma Subclasses," *Proc. Natl. Acad. Sci. USA* 98(24):13790-13795. (Epub. Nov. 13, 2001).

Bonadonna, G. et al. (Jan. 1998). "Primary Chemotherapy in Operable Breast Cancer: Eight-Year Experience at the Milan Cancer Institute," *J. Clin. Oncol.* 16(1):93-100.

Borczuk, A. C. et al. (Nov. 2003). "Non-Small-Cell Lung Cancer Molecular Signatures Recapitulate Lung Development Pathways," *Am. J. Pathol.* 163(5):1949-1960.

Bouchard, V. et al. (Jun. 2003). "PARP-1, a Determinant of Cell Survival in Response to DNA Damage," *Exp. Hematol.* 31(6):446-454.

Bryant, H.E. et al. (Apr. 14, 2005). "Specific Killing of BRCA2-Deficient Tumours with Inhibitors of Poly(ADP-Ribose) Polymerase," *Nature* 434(7035):913-917; and *Erratum in Nature* (May 17, 2007) 447(7142):346.

Buki, K. G. et al. (Sep. 1991). "Destabilization of $Zn^{2+}$ Coordination in ADP-Ribose Transferase (Polymerizing) by 6-Nitroso-1,2-Benzopyrone Coincidental With Inactivation of the Polymerase but not the DNA Binding Function," *FEBS Lett.* 290(1/2):181-185.

Buki, K.G. et al. (1992). "Inactivation of the Polymerase but not the DNA Binding Function of ADPRT by Destabilization of one of its $Zn^{2+}$ Coordination Centers by 6-Nitroso-1,2-Benzopryone," in *ADP-Ribosylation Reactions*, Poirier, G.G. et al., eds., Springer-Verlag: New York, NY, pp. 329-333.

Cepeda, V. et al. (2006). "Poly(ADP-ribose) Polymerase-1 (PARP-1) Inhibitors in Cancer Chemotherapy," *Rec. Pat. Anti-Cancer Drug Discov.* 1:39-53.

Chakraborty, A. K. et al. (Mar. 1, 2008). "Co-Targeting Insulin-Like Growth Factor I Receptor and HER2: Dramatic Effects of HER2 Inhibitors on Nonoverexpressing Breast Cancer," *Cancer Res.* 68(5):1538-1545.

Chang, J. W. et al. (May 2000). "Correlation of Genetic Instability With Mismatch Repair Protein Expression and *P53* Mutations in Non-Small Cell Lung Cancer," *Clin. Cancer Research* 6(5):1639-1646.

Chang, P. et al. (Dec. 2, 2004). "Poly(ADP-ribose) is Required for Spindle Assembly and Structure," *Nature* 432(7017):645-649.

Chen, Q.-R. et al. (Feb. 2007). "Diagnosis of the Small Round Blue Cell Tumors Using Multiplex Polymerase Chain Reaction," *Journal of Molecular Diagnostics* 9(1):80-88.

Chevallier, B. et al. (1993). "Inflammatory Breast Cancer. Pilot Study of Intensive Chemotherapy (FEC-HD) Results in a High Histologic Response Rate," *Am. J. Clin. Oncol.* 16:223-228.

Chin, K. et al. (Dec. 2006). "Genomic and Transcriptional Aberrations Linked to Breast Cancer Pathophysiologies," *Cancer Cell* 10(6)529-541.

Christie, M. et al. (Jun. 2006). "Molecular Pathology of Epithelial Ovarian," *Journal of the British Menopause Society* 12(2):57-63.

Chu, S. et al. (Aug. 24, 2007). "Poly(ADP-Ribose) Polymerase-1 Regulates Vimentin Expression in Lung Cancer Cells," *Am. J. Physiol.: Lung, Cell. Mol. Physiol.* 293:L1127-L1134.

Chuang, A. J. et al. (1994). "Comparison of the Cytotoxic and Antiretroviral Effects of 3-Nitrosobenzamide and 4-Iodo-3-Nitrobenzamide," *Proc. West. Pharmacol. Soc.* 37:117-119.

Classen, S. et al. (Sep. 16, 2003). "Structure of the Topoisomerase II ATPase Region and its Mechanism of Inhibition by the Chemotherapeutic Agent ICRF-187," *Proc. Natl. Acad. Sci. USA* 100(19):10629-10634, including Erratum published on Nov. 25, 2003, *Proc. Natl. Acad. Sci. USA* 100(24):14510-14511.

Cleator, S. et al. (Mar. 2007). "Triple-Negative Breast Cancer: Therapeutic Options," *Lancet Oncol.* 8:235-244.

Clinical Trials. US Government (2008). Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma, Verified by BiPar Sciences, Jul. 2009, first Received: May 28, 2008, last Updated: Jul. 23, 2009, located at http://clinicaltrials.gov/ct2/show/NCT00687687, last visited on Sep. 18, 2009.

Comen, E. A. et al. (May 20, 2008). "Prevalence of *BRCA1* and *BRCA2* Mutations in Jewish Women with Triple Negative Breast Cancer," *44th Annual Meeting of the American Society of Clinical Oncology*, May 30-Jun. 3, 2008, Chicago, IL, a supplement to the *J. Clin. Oncol.* 26(15S):749s, Abstract 22002, which can be located at <http://www.jco.ascopubs.org/cgi/mgca...>, last visited on Jun. 14, 2009, eight pages total.

Cosi, C. et al. (1994). "Poly(ADP-Ribose) Polymerase: Early Involvement in Glutamate-Induced Neurotoxicity in Cultured Cerebellar Granule Cells," *J. Neurosci. Res.* 39:38-46.

Cosi, C. et al. (2002). "New Inhibitors of Poly(ADP-Ribose) Polymerase and Their Therapeutic Targets," *Exp. Opin. Therapeut. Pat.* 12(7):1047-1071.

Costantino, G. et al. (2001). "Modeling of Poly(ADP-Ribose)Polymerase (PARP) Inhibitors. Docking of Ligands and Quantitative Structure-Activity Relationship Analysis," *J. Med. Chem.* 44(23):3786-3794 (ePUB 10/1308).

Curtin, J. P. et al. (Nov. 2001). "Paclitaxel in the Treatment of Carcinosarcoma of the Uterus: A Gynecologic Oncology Group Study," *Gynecologic Oncology* 83(2):268-270.

D'Adda Di Fagagna, F. et al. (Sep. 1999). "Functions of Poly(ADP-Ribose) Polymerase in Controlling Telomere Length and Chromosomal Stability," *Nature Genetics* 23(1):76-80.

D'Amours, D. et al. (Sep. 1, 1999). "Poly (ADP-Ribosyl)ation Reactions in the Regulation of Nuclear Functions," *Biochem J.* 342(Part 2):249-268.

Deger, R. B. et al. (Jul. 15, 1997). "Karyotic Analysis of 32 Malignant Epithelial Ovarian Tumors," *Cancer Genet. Cytogenet.* 96(2):166-173.

Delattre, O. et al. (Sep. 10, 1992). "Gene Fusion With an *ETS* DNA-Binding Domain Caused by Chromosome Translocation in Human Tumours," *Nature* 359(6391):162-165.

Delattre, O. et al. (Aug. 4, 1994). "The Ewing Family of Tumors—A Subgroup of Small-Round-Cell Tumors Defined by Specific Chimeric Transcripts," *N. Engl. J. Med.* 331(5):294-299.

Dent, R. et al. (Aug. 1, 2007). "Triple-Negative Breast Cancer: Clinical Features and Patterns of Recurrence," *Clin. Cancer Res.* 13(15 Pt 1):4429-4434.

De Soto, J. A. et al. (Jul. 15, 2006). "PARP-1 Inhibitors: Are They the Long-Sought Genetically Specific Drugs for BRCA1/2-Associated Breast Cancers?" *Int. J. Med. Sci.* 3(4):117-123.

De Soto, J. et al. (2006). "The Inhibition and Treatment of Breast Cancer with Poly (ADP-Ribose) Polymerase (PARP-1) Inhibitors," *Int. J. Biol. Sci.* 2(4):179-185.

Diebold, J. et al. (Apr. 2000). "20q13 and Cyclin D1 in Ovarian Carcinomas. Analysis by Fluorescence in Situ Hybridization," *J. Pathol.* 190(5):564-571.

Donawho, C. K. et al. (May 1, 2007). "ABT-888, an Orally Active Poly(ADP-Ribose) Polymerase Inhibitor that Potentiates DNA-Damaging Agents in Preclinical Tumor Models," *Clin. Cancer Res.* 13(19):2728-2737.

Donawho, C. K. et al. (2008). "The PARP Inhibitor, ABT-888 Overcomes Resistance in Temozolomide-Refractory Prostate and Breast Xenograft Tumors Implanted in Metastatic Sites in Vivo," Meeting Poster No. 555 (one page), and Palma, J. et al. (Oct. 24, 2008). "The PARP Inhibitor, ABT-888 Overcomes Resistance in Temozolomide-Refractory Prostate and Breast Xenograft Tumors Implanted in Metastatic Sites in Vivo," *20th EORTC-NCI-AACR, Symposium on Molecular Targets and Cancer Therapeutics, European Journal of Cancer* Supplements 6(12):175, poster No. 555.

Donegan, W. L. et al., eds., (1988). *Cancer of the Breast, 3rd Edition*, W. B. Saunders: Philadelphia, PA, in Chapter 17 entitled Endocrine Therapy of Breast Cancer, by C. G. Cardinal, pp. 504-506.

Dracopoli, N. C. et al. (Aug. 1, 1987). "Loss of Heterozygosity at Autosomal and X-Linked Loci During Tumor Progression in a Patient With Melanoma," *Cancer Research* 47(15):3995-4000.

Drew, Y. et al. (Sep. 2008). "The Potential of PARP Inhibitors in Genetic Breast and Ovarian Cancers," *Ann. N.Y. Acad. Sci.* 1138:136-145.

Durkacz, B. W. et al. (Feb. 7, 1980). "(ADP-Ribose)n. Participates in DNA Excision Repair," *Nature* 283:593-596.

Ellis, M.K. et al. (Apr. 15, 1992). "Reactions of Nitrosonitrobenzenes with Biological Thiols: Identification and Reactivity of Glutathion-S-yl Conjugates," *Chem. Biol. Interactions* 82(2):151-163.

Eyer, P. et al. (1980). "Biotransformation of Nitrosobenzene in the Red Cell and the Role of Glutathione," *Xenobiotica* 10(7/8):517-526.

Farmer, H. et al. (Apr. 14, 2005). "Targeting the DNA Repair Defect in *BRCA* Mutant Cells as a Therapeutic Strategy," *Nature* 434(7035):917-921.

Filmus, J. et al. (Jan. 1987). "Epidermal Growth Factor Receptor Gene-Amplified MDA-468 Breast Cancer Cell Line and its Nonamplified Variants," *Mol. Cell. Biol.* 7(1):251-257.

Fisher, B. et al. (Jul. 1997). "Effect of Preoperative Chemotherapy on Local-Regional Disease in Women With Operable Breast Cancer: Findings From the National Surgical Adjuvant Breast and Bowel Project B-18," *J. Clin. Oncol.* 15(7):2483-2493.

Fisher, B. et al. (Aug. 1998). "Effect of Preoperative Chemotherapy on the Outcome of Women With Operable Breast Cancer," *J. Clin. Oncol.* 16(8):2672-2685.

Flemming, G. F. (Jun. 1, 2004). "Phase III Trial of Doxorubicin plus Cisplatin With or Without Paclitaxel Plus Filgrastim in Advanced Endometrial Carcinoma: A Gynecologic Oncology Group Study," *J. Clin. Oncol.* 22(11):2159-2166; and comment in *Curr. Oncol. Rep.* (Nov. 2004). 6(6):455.

Flemming, G. F. et al. (Aug. 2004). "Phase III Randomized Trial of Doxorubicin + Cisplatin Versus Doxorubicin + 24-h Paclitaxel + Filgrastim in Endometrial Carcinoma, A Gynecologic Oncology Group Study," *Ann. Oncol.* 15(8):1173-1178.

Fletcher, J. A. et al. (Mar. 1991). "Ovarian Granulosa-Stromal Cell Tumors Are Characterized by Trisomy 12," *Am. J. Pathol.* 138(3):515-520.

Fong, P. C. et al. (2006). "Phase I Pharmacokinetic (PK) and Pharmacodynamic (PD) Evaluation of a Small Molecule Inhibitor of Poly ADP-Ribose Polymerase (PARP), KU-0059436 (Ku) in Patients (p) With Advanced Tumours," *Supplement to Journal of Clinical Oncology, 2006 ASCO Annual Meeting Proceedings*, Part I. vol. 24, No. 18S, Part I of II, (Jun. 20, 2006), p. 126s, abstract No. 3022.

Gäken, J. O. et al. (Jun. 1996). "Efficient Retroviral Infection of Mammalian Cells is Blocked by Inhibition of Poly(ADP-Ribose) Polymerase Activity," *Journal of Virology* 70(6):3992-4000.

Gallion, H. H. et al. (Sep. 1990). "Chromosome Abnormalities in Human Epithelial Ovarian Malignancies," *Gynecol. Oncol.* 38(3):473-477.

Garber, M. E. et al. (Nov. 20, 2001). "Diversity of Gene Expression in Adenocarcinoma of the Lung," *Proc. Natl. Acad. Sci. USA* 98(24):13784-13789. (Epub Nov. 13, 2001) and Erratum in *Proc. Natl. Acad. Sci. USA* (Jan. 22, 2002). 99(2):1098.

Garber, J. E. et al. (Dec. 14-17, 2006). "Neo-Adjuvant Cisplatin (CDDP) in 'Triple-Negative' Breast Cancer (BC)," *Breast Cancer*

Research and Treatment, Special Issue, 29th San Antonio Breast Cancer Symposium 2006; vol. 100, Poster Session III, p. S149, Abstract No. 3074.

Goldstein, J. (Feb. 13, 2008). "Latest Avastin Breast Cancer Study Unlikely to Sway FDA," The Wall Street Journal located at http://blogs.wsj.com/health/2008/02/13/latest-avastin-breast-cancer-study-unlikely-to-sway-fda/, last visited on Feb. 15, 2008, 3 pages total.

Griffin, R. J. et al. (Sep. 1995). "Novel Potent Inhibitors of the DNA Repair Enzyme Poly(ADP-Ribose)Polymerase (PARP)," Anticancer Drug Design 10(6):507-514.

Griffin, R. J. et al. (Jan. 10, 1996). "Novel Benzimidazole and Quinazolinone Inhibitors of the DNA Repair Enzyme Poly(ADP-Ribose)Polymerase," Pharmaceutical Sciences 2(1):43-47.

Griffin, R. J. et al. (1998). "Resistance-Modifying Agents. 5. Synthesis and Biological Properties of Quinazolinone Inhibitors of the DNA Repair Enzyme Poly(ADP-Ribose) Polymerase (PARP)," J. Med. Chem. 41(26):5247-5256.

Gudmundsdottir, K. et al. (Sep. 25, 2006). "The Roles of BRCA1 and BRCA2 and Associated Proteins in the Maintenance of Genomic Stability," Oncogene 25(43):5864-5874.

Hakam, A. et al. (Feb. 1987). "Catalytic Activities of Synthetic Octadeoxyribonucleotides as Coenzymes of Poly(ADP-Ribose) Polymerase and the Identification of a New Enzyme Inhibitory Site," FEBS Lett. 212(1):73-78.

Harris, N. L. et al. (Dec. 1999). "World Health Organization Classification of Neoplastic Diseases of the Hematopoietic and Lymphoid Tissues: Report of the Clinical Advisory Committee Meeting-Airlie House, Virginia, Nov. 1997," J. Clin. Oncol. 17(12)3835-3849.

Hassa, P. O. et al. (Dec. 7, 2001). "The Enzymatic and DNA Binding Activity of PARP-1 Are Not Required for NF-κB Coactivator Function," J. Biol. Chem. 276(49):45588-45597.

Hassa, P. O. et al. (Sep. 2006). "Nuclear ADP-Ribosylation Reactions in Mammalian Cells: Where Are We Today and Where Are We Going?" Microbiol. Mol. Biol. Rev. 70(3):789-829.

Heighway, J. et al. (Oct. 31, 2002). "Expression Profiling of Primary Non-Small Cell Lung Cancer for Target Identification," Oncogene 21(50):7749-7763.

Helleday, T. et al. (Mar. 2008). "DNA Repair Pathways as Targets for Cancer Therapy," Nat. Rev. Cancer. 8(3):193-204.

Hellström, I. et al. (Mar. 15, 2001). "Overexpression of HER-2 in Ovarian Carcinomas," Cancer Res. 61(6):2420-2423.

Henderson, L. E. et al. (Aug. 25, 1981). "Primary Structure of the Low Molecular Weight Nucleic Acid-binding Proteins of Murine Leukemia Viruses," J. Biol. Chem. 256(16):8400-8403.

Herceg, Z. et al. (Jun. 2, 2001). "Functions of Poly(ADP-Ribose) Polymerase (PARP) in DNA Repair, Genomic Integrity and Cell Death," Mutat. Res. 477(1-2):97-110.

Hickman, J. A. (Sep. 1975). "Protection Against the Effects of the Antitumour Agent CB 1954 by Certain Imidazoles and Related Compounds," Biochemical Pharmacology 24(17):1947-1952.

Higashi, T. et al. (1983). "Retrospects and Prospects," Glutathione: Storage, Transport and Turnover in Mammals, eds., Sakamoto, Y. et al. Japan Sci. Soc. Press, Tokyo,/VNU Science Press, Utrecht, pp. 3-9.

Hod, Y. (Dec. 1992). "A Simplified Ribonuclease Protection Assay," Biotechniques 13(6):852-854.

Höglund, M. et al. (Jun. 15, 2003). "Ovarian Carcinoma Develops Through Multiple Modes of Chromosomal Evolution," Cancer Research 63(12):3378-3385.

Homesley, H. D. et al. (Feb. 10, 2007). "Phase III Trial of Ifosfamide With or Without Paclitaxel in Advanced Uterine Carcinosarcoma: A Gynecologic Oncology Group Study," J. Clin. Oncol. 25(5):526-531.

Honkoop, A. H. et al. (1998). "Prognostic Role of Clinical, Pathological and Biological Characteristics in Patients with Locally Advanced Breast Cancer," Br. J. Cancer 77(4):621-626.

Hubert, A. et al. (Aug.-Sep. 2004). "PARP-1, PARP-2 and ATM in the DNA Damage Response: Functional Synergy in Mouse Development," DNA Repair (Amst). 3(8-9):1103-1108.

Hwang, S. J. et al. (Aug. 2003). "Lung Cancer Risk in Germline p53 Mutation Carriers: Association Between an Inherited Cancer Predisposition, Cigarette Smoking, and Cancer Risk," Hum. Genet. 113(3):238-243. (Epub. Jun. 11, 2003).

Irvin, J. W. Jr. et al. (Dec. 2008). "What is Triple-Negative Breast Cancer?" Eur. J. Cancer 44(18):2799-2805.

Iwabuchi, H. et al. (Dec. 15, 1995). "Genetic Analysis of Benign, Low-Grade, and High-Grade Ovarian Tumors," Cancer Res. 55(24):6172-6180.

Jacob, D. A. et al. (2007). "Combination Therapy of Poly (ADP-Ribose) Polymerase Inhibitor 3-Aminobenzamide and Gemcitabine Shows Strong Antitumor Activity in Pancreatic Cancer Cells," J. Gastroenterol. Hepatol. 22:738-748.

Jagtap, P. et al. (2002). "Novel Phenanthridinone Inhibitors of Poly (Adenosine 5'Diphosphate-Ribose) Synthetase: Potent Cytoprotective and Antishock Agents," Crit. Care Med. 30(5):1071-1082.

Jagtap, P. et al. (May 2005). "Poly(ADP-Ribose) Polymerase and the Therapeutic Effects of its Inhibitors," Nature Rev. Drug Disc. 4:421-440.

Jemal, A. et al. (Jan./Feb. 2003). "Cancer Statistics 2003," CA Cancer J. Clin. 53(1):5-26.

Jenkins, R. B. et al. (Nov. 1993). "Cytogenetic Studies of Epithelial Ovarian Carcinoma," Cancer Genet. Cytogenet. 71(1):76-86.

Jeon, I. S. et al. (Mar. 16, 1995). "A Varian Ewing's Sarcoma Translocation (7;22) Fuses the EWS Gene to the ETS Gene ETV1," Oncogene 10(6):1229-1234.

Jones, C. et al. (Oct. 2008). "PARP Inhibitors and Cancer Therapy—Early Results and Potential Applications," Br. J. Radiol. 81 Spec No. 1:S2-S5.

Kandel, M. J. et al. (2006). "Prevalence of BRCA1 Mutations in Triple Negative Breast Cancer (BC)," 2006 ASCO Annual Meeting, Supplemental to the Journal of Clinical Oncology, Jun. 20, 2006, Part I, vol. 24, No. 18S, abstract No. 508.

Karczewski, J. M. et al. (1999). "Prevention of Oxidant-Induced Cell Death in Caco-2 Colon Carcinoma Cells after Inhibition of Poly(ADP-Ribose) Polymerase and $Ca^{2+}$ Chelation: Involvement of a Common Mechanism," Biochem. Pharmacol. 57:19-26.

Khalid, M. N. et al. (Apr. 2006). "Long Circulating Poly(Ethylene Glycol)-Decorated Lipid Nanocapsules Deliver Docetaxel to Solid Tumors," Pharm. Res. 23(4):752-758.

Kiechle, M. et al. (Feb. 1, 2001). "Comparative Genomic Hybridization Detects Genetic Imbalances in Primary Ovarian Carcinomas as Correlated With Grade of Differentiation," Cancer 91(3):534-540.

Kiechle-Schwarz, M. et al. (Nov. 1994). "Recurrent Cytogenetic Aberrations and Loss of Constitutional Heterozygosity in Ovarian Carcinomas," Gynecol. Oncol. 55(2):198-205.

Kim, M. Y. et al. (Dec. 17, 2004). "$NAD^+$-Dependent Modulation of Chromatin Structure and Transcription by Nucleosome Binding Properties of PARP-1," Cell 119(6):803-814.

Kindler, H. L. (2007). "A Double-Blind, Placebo-Controlled, Randomized Phase III Trial of Gemcitabine (G) Plus Bevacizumab (B) Versus Gemcitabine plus Placebo (P) in Patients (pts) with Advanced Pancreatic Cancer (PC): A Preliminary Analysis of Cancer and Leukemia Group B (CALGB) 80303," Gastrointestintal Cancers Symposium: Mutidisciplinary Approaches to the Prevention, Diagnosis, and Therapy of GI Cancers, Jan. 19-21, 2007, Orlando, Florida, p. 319, abstract 108.

Kirsten, E. et al. (2000). "Cancer Cell Selectivity of 5-lodo-6-Aminobenzopyrone (INH2BP) and Methyl 3-5-Diiodo-4(4'-Methoxyphenol) Benzoate (DIME)," Int'l J. Mol. Med. 5(3):279-281.

Kiyohara, C. et al. (Sep. 2002). "Genetic Polymorphisms and Lung Cancer Susceptibility: A Review," Lung Cancer 37(3):241-256.

Ko, A. H. (Feb. 17, 2003). "Cancer of the Pancreas," published by Cancer Supportive Care Programs, article located at http://www.cancersupportivecare.com/pancreas/html, last visited on Sep. 23, 2009, 5 pages total.

Kosower, E.M. (1976). "Chemical Properties of Glutathione," Chapter 1 in Glutathione Metabolism and Function, Arias, M. et al., eds., Raven Press: New York, NY, Kroc Foundation Series, vol. 6, pp. 1-15.

Kuerer H. M., et al. (Jul./Aug. 1998). "Pathologic Tumour Response in the Breast Following Neoadjuvant Chemotherapy Predicts Axillary Lymph Node Status," Cancer J. Sci. Am. 4(4):230-236.

Kuerer H. M. et al. (Feb. 1999). "Clinical Course of Breast Cancer Patients With Complete Pathologic Primary Tumour and Axillary Lymph Node Response to Doxorubicin-Based Neoadjuvant Chemotherapy," J. Clin. Oncol. 17(2):460-469.

Kun, E. et al. (1983). "Biochemical Basis of the Regulatory Role of Polyadenosine Diiphosphoribose," *Advances in Enzyme Regulation* 21:177-199.

Kun, E. et al. (Mar.-Jun. 2001). "Cell Biological Functions of PARP-1: An Overview," *Ital. J. Biochem.* 50(1-2):15-18.

Kun, E. et al. (2003). "Synergistic Anticancer Action of Reversibly and Irreversibly Acting Ligands of Poly (ADP-Ribose) Polymerase," *Int'l J. Mol. Med.* 11(2):191-193.

Kun, E. et al. (2006). "Quantitative Correlation Between Cellular Proliferation and Nuclear Poly (ADP-Ribose) Polymerase (PARP-1)," *Int'l J. Mol. Med.* 17:293-300.

Lau, A. et al. (Oct. 21-24, 2008). "Pre-Clinical Activity of the PARP Inhibitor Olaparib (AZD2281) in Homologous Recombination Repair Deficient Triple Negative Breast Cancer," Poster at *20th EORTC-NCI-AACR Symposium on "Molecular Targets and Cancer Therapeutics,"* Oct. 21-24, 2008, Geneva, Switzerland, two pages.

Lee-Jones, L. (Aug. 2003). "Ovary: Germ Cell Tumors," *Atlas of Genetics and Cytogenetics in Oncology and Haematology*, pp. 591-605, located at http://atlasgeneticsoncology.org/Tumors/OvarianGermCellID5067.pdf last visited on Sep. 25, 2009, 15 pages total.

Lee-Jones, L. (Nov. 2003). "Ovary: Sex Cord-Stromal Tumors," *Atlas of Genetics and Cytogenetics in Oncology and Haematology*, 8(1):125-131, located at http://AtlasGeneticsOncology.org/Tumors/OvarSexCordStromID5223.html, last visited on Sep. 25, 2009, 15 pages total.

Lee-Jones, L. (Dec. 2003). "Ovary: Epithelial Tumors," *Atlas Genet Cytogenet Oncol Haematol* 8(2):256-302, located at http://atlasgeneticsoncology.org/Tumors/OvaryEpithTumID5230.pdf, 51 pages total.

Leslie, K. K. et al. (2005). "Tyrosine Kinase Inhibitors in Endometrial Cancer," *International Journal of Gynecological Cancer* 15:409-411, abstract No. 0020.

Lev, D. C. et al. (Aug. 2003). "Dacarbazine Causes Transcriptional up-Regulation of Interleukin 8 and Vascular Endothelial Growth Factor in Melanoma Cells; A Possible Escape Mechanism From Chemotherapy," *Mol. Cancer Therap.* 2(8):753-763.

Lever, A. et al. (Sep. 1989). "Identification of a Sequence Required for Efficient Packaging of Human Immunodeficiency Virus Type 1 RNA into Virus," *J. Virol.* 63(9):4085-4087.

Lewis, G. D. et al. (Sep. 1993). "Differential Responses of Human Tumor Cell Lines to Anti-p185HER2 Monoclonal Antibodies," *Cancer Immunol. Immunother.* 37(4):255-263.

Li, J.-H. et al. (2001). "Synthesis of Substituted 5[*H*]phenanthridin-6-ones as Potent Poly(ADP-Ribose)Polymerase-1 (PARP1) Inhibitors," *Bioorg. Med. Chem. Lett.* 11:1687-1690.

Loesch, D. M. (Dec. 8-11, 2005). "Phase II Trial of Gemcitabine Plus Carboplatin (plus Trastuzumab in HER-2 Positive Patients) in Metastatic Breast Cancer Patients," *Breast Cancer Research and Treatment, Special Issue 28th annual San Antonio Breast Cancer Symposium 2005*, San Antonio, Texas, vol. 94, Supplement 1, p. S280, Poster Session VI, Abstract No. 6092.

Marsit, C. J. et al. (Jan. 29, 2004). "Inactivation of the Fanconi Anemia/BRCA Pathway in Lung and Oral Cancers: Implications for Treatment and Survival," *Oncogene* 23(4):1000-1004.

Mayr, D. et al. (Sep. 2002). "Characteristic Pattern of Genetic Aberrations in Ovarian Granulosa Cell Tumors," *Mod. Pathol.* 15(9):951-957.

Mazzon, E. et al. (Mar. 1, 2001). "GPI 6150, a Poly (ADP-Ribose) Polymerase Inhibitor, Exhibits an Anti- Inflammatory Effect in Rat Models of Inflammation," *Eur. J. Pharmacol.* 415(1):85-94.

McCabe, N. et al. (Aug. 15, 2006). "Deficiency in the Repair of DNA Damage by Homologous Recombination and Sensitivity to Poly(ADP-ribose) Polymerase Inhibition," *Cancer Res.* 66(16):8109-8115.

McCluggage, W. G. (May 2002). "Malignant Biphasic Uterine Tumors: Carcinosarcomas or Metaplastic Carcinomas?" *J. Clin. Pathol.* 55(5):321-325.

McLaughlin, P. et al. (Aug. 1998). "Rituximab Chimeric Anti-CD20 Monoclonal Antibody Therapy for Relapsed Indolent Lymphoma: Half of Patients Respond to a Four-Dose Treatment Program,"*J. Clin. Oncol.* 16(8):2825-2833.

Ménissier De Murcia, J. et al. (Jul. 8, 1997). "Requirement of Poly(ADP-Ribose) Polymerase in Recovery From DNA Damage in Mice and in Cells," *Proc. Natl. Acad. Sci. USA* 94(14):7303-7307.

Meric, C. et al. (Apr. 1989). "Characterization of Moloney Murine Leukemia Virus Mutants with Single-Amino-Acid Substitutions in the Cys-His Box of the Nucleocapsid," *J. Virol.* 63(4):1558-1568.

Mitsuuchi, Y. et al. (Oct. 30, 2002). "Cytogenetics and Molecular Genetics of Lung Cancer," *Am. J. Med. Genet.* 115(3):183-188.

Miller, D. S. et al. (Aug. 2005). "Phase II Evaluation of Topotecan in Carcinosarcoma of the Uterus: A Gynecologic Oncology Group Study," *Gynecologic Oncology* 98(2):217-221.

Mrózek, K. et al. (Mar. 1990). "Trisomy of Chromosome 12 in a Case of Thecoma of the Ovary," *Gynecol. Oncol.* 36(3):413-416.

Mugneret, F. et al. (Jun. 1988). "Chromosomes in Ewing's Sarcoma. II. Nonrandom Additional Changes, Trisomy 8 and der(16)t(1:16)," *Cancer Genet. Cytogenet.* 32(2):239-245.

Nahleh, Z. et al. (Nov. 2007). "Trastuzumab not for Ductal Carcinoma in Situ?" *Anticancer Drugs* 18(10):1231-1235.

Nahta, R. et al. (May 2006). "Mechanisms of Disease: Understanding Resistance to HER2-Targeted Therapy in Human Breast Cancer," *Nat. Clin. Pract. Oncol.* 3(5):269-280.

Narod, S. A. et al. (Sep. 2004). "*BRCA1* and *BRCA2*: 1994 and beyond," *Nat. Rev. Cancer* 4(9):665-676.

Nguewa, P. A. et al. (2003). "Pharmacological Modulation of Poly(ADP-Ribose) Polymerase-Mediated Cell Death: Exploitation in Cancer Chemotherapy," *Mol. Pharmacol.* 64(5):1007-1014.

Nitta, K. et al. (Mar. 1987). "Antitumor Activity of New Derivatives of Camptothecin," *Gan to Kagaku Ryoho.* 14(3 Pt 2):850-857. This article is in Japanese with English abstract on p. 857.

Nomura, F. et al. (May 2000). "Enhancement of Poly-Adenosine Diphosphate-Ribosylation in Human Hepatocellular Carcinoma," *J. Gastroenterol. Hepatol.* 15(5):529-535.

Ogston, K. N. et al. (2003). "A New Histological Grading System to Assess Response of Breast Cancers to Primary Chemotherapy: Prognostic Significance and Survival," *Breast* 12:320-327.

Olver, I. N. (Feb. 2008). "Trastuzumab as the Lead Monoclonal Antibody in Advanced Breast Cancer: Choosing Which Patient and When," *Future Oncol.* 4(1):125-131.

Omura, G. A. et al. (Aug. 15, 1983). "A Randomized Study of Adriamycin With and Without Dimethyl Triazenoimidazole Carboxamide in Advanced Uterine Sarcomas," *Cancer* 52(4):626-632.

Oosting-Lenstra, S. F. et al. (Dec. 2007). "Failure of CHOP with Rituximab for Lymphomatoid Granulomatosis," *Neth. J. Med.* 65(11):442-447.

(OSI)™ Pharmaceuticals, (Aug. 9, 2005). "Tarceva® (Erlotinib) Tablets NDA 21-743, S003, Supplemental NDA: Pancreatic Cancer, Briefing Document, ODAC Meeting Sep. 13, 2005," PDF located at http://www.fda.gov/ohrms/dockets/AC/05/briefing/2005-4174B1_03_01-OSI-Tarceva.pdf, 66 pages total, last visited Sep. 25, 2009.

Parker, R. M. C. et al. (1999). "mRNA: Detection by in Situ and Northern Hybridization," *Methods in Molecular Biology*, Chapter 14, 106:247-283.

Pedersen, M. I. et al. (Feb. 1, 1986). "Nonrandom Chromosome Structural Aberrations and Oncogene Loci in Human Malignant Melanoma," *Cancer Genet. Cytogenet.* 20(1-2):11-27.

Pejovic, T. et al. (May 1990). "Trisomy 12 is a Consistent Chromosomal Aberration in Benign Ovarian Tumors," *Genes Chromosomes Cancer* 2(1):48-52.

Pejovic, T. et al. (Jan. 1992). "Chromosome Aberrations in 35 Primary Ovarian Carcinomas," *Genes Chromosomes Cancer* 4(1):58-68.

Pejovic, T. et al. (Feb. 1995). "Genetic Changes in Ovarian Cancer," *Ann. Med.* 27(1):73-78.

Perkins, E. et al. (May 15, 2001). "Novel Inhibitors of Poly(ADP-Ribose) Polymerase/PARP1 and PARP2 Identified Using a Cell-Based Screen in Yeast," *Cancer Res.* 61:4175-4183.

Plummer, R. et al. (2005). "First in Human Phase I Trial of the PARP Inhibitor AG-014699 With Temozolomide (TMZ) in Patients (pts) With Advanced Solid Tumors," *2005 41st Annual Meeting of the American Society of Clinical Oncology*, May 13-17, 2005, Orlando Florida, 2005 Annual Meeting Proceedings Part I, (a supplement to the Journal of Clinical Oncology, vol. 23, No. 16S, Part I of II (Jun. 1 Supplement), p. 208s, abstract No. 3065.

Plummer, R. et al. (2006). "First and Final Report of a Phase II Study of the Poly(ADP-Ribose) Polymerase (PARP) Inhibitor, AG014699, in Combination With Temozolomide (TMZ) in Patients With Metastatic Malignant Melanoma (MM)," *2006 42$^{nd}$ Annual Meeting of the American Society of Clinical Oncology*, Jun. 2-6, 2006, Atlanta, GA, Supplement to the Journal of Clinical Oncology, Part I of II, vol. 24, No. 18S (Jun. 20, 2006) p. 456s, abstract No. 8013.

Powles, T. J. et al. (Mar. 1995). "Randomized Trial of Chemoendocrine Therapy Started Before or After Surgery for Treatment of Primary Breast Cancer," *J. Clin. Oncol.* 13(3):547-552.

Ramonas, K. et al. (2005). "Treatment of Transgenic Murine Retinoblastoma With 4-Iodo-3-Nitrobenzamide ($INO_2BA$), a Novel Chemotherapeutic Agent," *Invest. Ophthalmol. Vis. Sci.* 46(5):E-Abstract 3422-B975, 2 pages total, also located at http://abstracts.iovs.org/cgi/content/abstract/46/5/3422, 2 pages.

Ratnam, K. et al. (Mar. 1, 2007). "Current Development of Clinical Inhibitors of Poly(ADP-Ribose) Polymerase in Oncology," *Clin. Cancer Res.* 13(5):1383-1388.

Rattan, S. I. et al. (Jun. 15, 1994). "Kinetin Delays the Onset of Ageing Characteristics in Human Fibroblasts," *Biochem. Biophys. Res. Comm.* 201(2):665-672.

Razzak, A. R. et al. (2008). "Heterogeneity of Breast Cancer and Implications of Adjuvant Chemotherapy," *Breast Cancer* 15(1):31-34.

Reis-Filho, J. S. et al. (2008). "Triple Negative Tumours: a Critical Review," *Histopathol.* 52:108-118.

Ries, L.A.G., et al. (eds) (2007). SEER Cancer Statistics Review, 1975-2004, National Cancer Institute. Bethesda, MD, based on Nov. 2006 SEER data submission, posted to the SEER web site, 2007, located at http://seer.cancer.gov/csr/1975_2004/.

Richmond, A. et al. (Mar. 1986). "Growth Factor and Cytogenetic Abnormalities in Cultured Nevi and Malignant Melanomas," *J. Invest. Dermatol.* 86(3):295-302.

Roberts, C. G. et al. (Sep. 1990). "Cytogenetic Study of Solid Ovarian Tumors," *Cancer Genet. Cytogenet.* 48(2):243-253.

Rottenberg, S. et al. (Nov. 4, 2008). "High Sensitivity of BRCA1-Deficient Mammary Tumors to the PARP Inhibitor AZD2281 Alone and in Combination With Platinum Drugs," *Proc. Natl. Acad. Sci. USA* 105(44):17079-17084.

Said, S. I. et al. (May 1996). "Excitotoxicity in the Lung: *N*-Methyl-D-Aspartate-Induced, Nitric Oxide-Dependent, Pulmonary Edema is Attenuated by Vasoactive Intestinal Peptide and by Inhibitors of Poly(ADP-Ribose) Polymerase," *Proc. Natl. Acad. Sci. USA* 93:4688-4692.

Sataloff, D. M. et al. (Mar. 1995). "Pathologic Response to Induction Chemotherapy in Locally Advanced Carcinoma of the Breast: a Determinant of Outcome," *J. Am.Coll. Surg.* 180(3):297-306.

Schlicker, A. et al. (Jan. 1, 1999). "4-Amino-1,8-Naphthalimide: a Novel Inhibitor of Poly(ADP-Ribose) Polymerase and Radiation Sensitizer," *Int. J. Radiat. Biol.* 75(1):91-100.

Schreiber, V. et al. (Jul. 2006). "Poly(ADP-ribose): Novel Functions for an Old Molecule," *Nat. Rev. Mol. Cell Biol.*7(7):517-528.

Seracchioli, R. et al. (Jun. 2001). "Conservative Treatment of Recurrent Ovarian Fibromas in a Young Patient Affected by Gorlin Syndrome," *Hum. Reprod.* 16(6):1261-1263.

Serra, V. et al. (Oct. 1, 2008). "NVP-BEZ235, a Dual PI3K/mTOR Inhibitor, Prevents PI3K Signaling and Inhibits the Growth of Cancer Cells with Activating PI3K Mutations," *Cancer Res.* 68(19):8022-8030.

Shall, S. et al. (May 11, 1999). "Preparation of Aminobenzamides and Related Compounds as Inhibitors of Poly(ADP-Ribose)-Metabolizing Enzymes," *Chemical Abstracts* 116(19):193929e.

Silverberg, S. G. et al. (1991). "Carcinomas," in Tumors of the Uterine Corpus and Gestational Trophoblastic Disease, Atlas of Tumor Pathology, in 3$^{rd}$ Series, Fascicule 3, Washington D. C., Armed Forces Institute of Pathology, pp. 166-179.

Simbulan-Rosenthal, C. M. et al. (Oct. 10, 2000). "Misregulation of Gene Expression in Primary Fibroblasts Lacking Poly(ADP-Ribose) Polymerase," *Proc. Natl. Acad. Sci. USA* 97(21):11274-11279.

Simbulan-Rosenthal, C. M. et al. (Nov. 20, 2003). "PARP-1 Binds E2F-1 Independently of its DNA Binding and Catalytic Domains, and Acts as a Novel Coactivator of E2F-1-Mediated Transcription During Re-Entry of Quiescent Cells into S Phase," *Oncogene* 22(52):8460-8471.

Simon, R. (Mar. 1989). "Optimal Two-Stage Designs for Phase II Clinical Trials," *Control Clin. Trials* 10(1):1-10.

Singh, N. (Jun. 14, 1991). "Enhanced Poly ADP-Ribosylation in Human Leukemia Lymphocytes and Ovarian Cancers," *Cancer Lett.* 58(1-2):131-135.

Slayton, R. E. et al. (Jun. 1987). "Phase II Trial of Etoposide in the Management of Advanced or Recurrent Mixed Mesodermal Sarcomas of the Uterus: A Gynecologic Oncology Group Study," *Cancer Treatment Reports* 71(6):661-662.

Sonoda, G. et al. (Dec. 1997). "Comparative Genomic Hybridization Detects Frequent Overrepresentation of Chromosomal Material From 3q26, 8q24, and 20q13 in Human Ovarian Carcinomas," *Genes Chromosomes Cancer* 20(4):320-328.

Soriano, F. G. et al. (Jan. 2001). "Diabetic Endothelial Dysfunction: The Role of Poly(ADP-Ribose) Polymerase Activation," *Nature Medicine* 7(1):108-113.

Sorlie, T. et al. (Jul. 8, 2003). "Repeated Observation of Breast Tumor Subtypes in Independent Gene Expression Data Sets," *Proc. Natl. Acad. Sci. USA* 100(14):8418-8423. Epub Jun. 26, 2003.

Stephenson, C. F. et al. (Nov. 1992). "Cytogenetic and Pathologic Aspects of Ewing's Sarcoma and Neuroectodermal Tumors," *Hum. Pathol.* 23(11):1270-1277.

Stryer, L. (1981). *Biochemistry*, Second Edition, W.H. Freeman and Company: San Francisco, CA, Part II, Chapter 15 entitled "Pentose Phosphate Pathway and Glucogenesis," pp. 343-345.

Sutton, G. P. et al. (Aug. 1989). "Phase II Trial of Ifosfamide and Mesna in Mixed Mesodermal Tumors of the Uterus, (A Gynecologic Oncology Group Study)." *Am. J. Obstet. Gynecol.* 161(2):309-312.

Sutton, G. et al. (Nov. 2000). "A Phase III Trial of Ifosfamide With or Without Cisplatin in Carcinosarcoma of the Uterus, A Gynecologic Oncology Group Study," *Gynecologic Oncology* 79(2):147-153, and comment in *Gynecol. Oncol.* (Nov. 2000) 79(2)145-146.

Suzuki, S. et al. (Oct. 1, 2000). "An Approach to Analysis of Large-Scale Correlations Between Genome Changes and Clinical Endpoints in Ovarian Cancer," *Cancer Research* 60(19):5382-5385.

Szabó, C. et al. (Jun. 1997). "Regulation of Components of the Inflammatory Response by 5-Iodo-6-Amino-1,2Benzopyrone, an Inhibitor of Poly(ADP-Ribose) Synthetase and Pleiotropic Modifier of Cellular Signal Pathways," *International Journal of Oncology* 10(6):1093-1101.

Taetle, R. et al. (Jul. 1999). "Chromosome Abnormalities Adenocarcinoma: I. Nonrandom Chromosome Abnormalities from 244 Cases," *Genes Chromosomes Cancer* 25(3):290-300.

Tanner, M. M. et al. (May 2000). "Frequent Amplification of Chromosomal Region 20q12-q13 in Ovarian Cancer," *Clin. Cancer Research* 6(5):1833-1839.

Taruscio, D. et al. (Jun. 1993). "Detection of Trisomy 12 on Ovarian Sex Cord Stromal Tumors by Fluorescence in Situ Hybridization," *Diagn. Mol. Pathol.* 2(2):94-98.

Thigpen, J. T. et al. (Feb. 1986). "Phase II Trial of Cisplatin in the Treatment of Patients with Advanced or Recurrent Mixed Mesodermal Sarcomas of the Uterus: A Gynecologic Oncology Group Study," *Cancer Treatment Reports* 70(2):271-274.

Thigpen, J. T. et al. (Oct. 1, 2004). "Phase III Trial of Doxorubicin With or Without Cisplatin in Advanced Endometrial Carcinoma: A Gynecologic Oncology Group Study," *J. Clin. Oncol.* 22(19):3902-3908.

Thomas, H. D. et al. (Mar. 2007). "Preclinical Selection of a Novel Poly(ADP-Ribose) Polymerase Inhibitor for Clinical Trial," *Mol. Cancer Ther.* 6(3):945-956.

Thompson, F. H. et al. (Mar. 1994). "Clonal Chromosome Abnormalities in 54 Cases of Ovarian Carcinoma," *Cancer Genet. Cytogenet.* 73(1):33-45.

Turc-Carel, C. et al. (Jun. 1988). "Chromosomes in Ewing's Sarcoma. I. An Evaluation of 85 Cases of Remarkable Consistency of t(11;22)(q24;q12)," *Cancer Genet. Cytogenet.* 32(2):229-238.

Virag, L. et al. (1999). "Inhibition of Poly(ADP-Ribose) Synthetase (PARS) and Protection Against Peroxynitrite-Induced Cytotoxicity by Zinc Chelation," *Br. J. Pharmacol.* 126:769-777.

Virag, L. (1999). "Requirement of Intracellular Calcium Mobilization for Peroxynitrite-Induced Poly(ADP-Ribose) Synthetase Activation and Cytotoxicity," *Mol. Pharmacol.* 56:824-833.

Virag, L. et al. (Jan. 2001). "Purines Inhibit Poly(ADP-Ribose) Polymerase Activation and Modulate Oxidant-Induced Cell Death," *FASEB J.* 15:99-107.

Virag, L. et al. (2002). "The Therapeutic Potential of Poly(ADP-Ribose) Polymerase Inhibitors," *Pharmacol Rev.* 54(3):375-429.

Wang, Z. Q. et al. (1995). "Mice Lacking ADPRT and Poly(ADP-Ribosyl)ation Develop Normally but are Susceptible to Skin Disease," *Genes Dev.* 9:509-520.

Wang, Z.-Q. et al. (Sep. 15, 1997). "PARP is Important for Genomic Stability but Dispensable in Apoptosis," *Genes Dev.* 11(18):2347-2358.

Wasserman, E. J. et al. (2008). "Evolving Strategies for the Treatment of 'Triple-Negative' Breast Cancer," *American Society of Clinical Oncology Educational Book*, pp. 120-126.

Watson, C. Y. et al. (1998). "Synthesis of 3-Substituted Benzamides and 5-Substituted Isoquinolin- 1(2H)-ones and Preliminary Evaluation as Inhibitors of Poly(ADP-Ribose)Polymerase (PARP)," *Bioorg Med Chem.* 6:721-734.

Weisner, R. J. et al. (Aug. 1992). "Detection of Rare mRNAs via Quantitative RT-PCR," *Trends Genet.* 8(8):263-264.

White, A. W. et al. (2000). "Resistance-Modifying Agents. 9. Synthesis and Biological Properties of Benzimidazole Inhibitors of the DNA Repair Enzyme Poly(ADP-Ribose) Polymerase," *J. Med. Chem.* 43:4084-4097.

Winer, E. P. et al. (2007). "Optimizing Treatment of 'Triple-Negative' Breast Cancer," *30th Annual San Antonio Breast Cancer Symposium, selection from SABCS 2007: Improving Outcomes in Advanced and Metastatic Breast Cancer*, 4 pages total.

Yalcintepe, L. et al. (Mar. 2005). "Changes in NAD/ADP-Ribose Metabolism in Rectal Cancer," *Braz. J. Med. Biol. Res.* 38(3):361-365 (article in English).

Yang-Feng, T. L. et al. (Jul. 9, 1991). "Trisomy 12 and K-ras-2-Amplification in Human Ovarian Tumors," *Int. J. Cancer* 48(5):678-681.

Yanochko, G. M. et al. (Apr. 3, 2006). "Type I Insulin-Like Growth Factor Receptor Over-Expression Induces Proliferation and Anti-Apoptotic Signaling in a Three-Dimensional Culture Model of Breast Epithelial Cells," *Breast Cancer Res.* 8(2):R18, pp. 1-13.

Yoshida, S. et al. (Jan. 1991). "Production of 2-Methyl-4[3H]-Quinazolinone, an Inhibitor of Poly(ADP-Ribose) Synthetase, by Bacterium," *The Journal of Antibiotics (Tokyo)*, 44(1):111-112.

Zabarovsky, E. R. et al. (Oct. 7, 2002). "Tumor Suppressor Genes on Chromosome 3p Involved in the Pathogenesis of Lung and Other Cancers," *Oncogene* 21(45):6915-6935.

Zhang, J. et al. (Nov. 30, 2000). "GPI 6150 Prevents $H_2O_2$ Cytotoxicity by Inhibiting Poly(ADP-Ribose) Polymerase," *Biochem. Biophys. Res. Comm.* 278(3):590-598.

International Search Report mailed on Dec. 3, 2007, for PCT Application No. PCT/US07/71053 filed on Jun. 12, 2007, 1 page.

International Search Report mailed on Oct. 16, 2007, for PCT Application No. PCT/US06/27907 filed on Jul. 18, 2006, 1 page.

International Search Report mailed on Jun. 16, 2008, for PCT Application No. PCT/US07/77651 filed on Sep. 5, 2007, 1 page.

International Search Report mailed on Feb. 13, 2009, for PCT Application No. PCT/US08/85756 filed on Dec. 5, 2008, 1 page.

Written Opinion of the International Search Authority mailed on Oct. 16, 2007, for PCT Patent Application No. PCT/US06/27907 filed Jul. 18, 2006.

U.S. Appl. No. 12/496,593, filed Jul. 1, 2009, for Sherman et al.
U.S. Appl. No. 12/502,943, filed Jul. 14, 2009, for Sherman et al.
U.S. Appl. No. 12/510,969, filed Jul. 28, 2009, for Sherman et al.

Andersen, B. et al. (Oct. 15, 2002). "The Effect of Glucose on the Potency of Two Distinct Glycogen Phosphorylase Inhibitors," *Biochem. J.* 367(Pt 2):443-450.

Balakumar, P. et al. (2006). "Effect of 3-Aminobenzamide, an Inhibitor of Poly(ADP-Ribose) Polymerase in Experimental Cardiac Hypertrophy," *Int. J. Pharmacol.* 2(5):543-548.

Boros, L. G. et al. (Mar. 6, 2002). "Metabolic Profiling of Cell Growth and Death in Cancer: Applications in Drug Discovery," *Drug Discovery Today* 7(6):364-372.

Bowman, K. J. et al. (Jan. 5, 2001). "Differential Effects of the Poly(ADP-Ribose) Polymerase (PARP) Inhibitor NU1025 on Topoisomerase I and II Inhibitor Cytotoxicity in L1210 Cells in Vitro," *Br. J. Cancer* 84(1):106-112.

Cancer.org (2005). "What is Ovarian Cancer?" available online as of Feb. 5, 2005 as evidenced by the attached Internet Archive Report located at http://www.cancer.org/docroot/CRI/content/CRI_2_4_1X_What_is_ovarian_cancer_33.asp, 6 pages total.

Comin-Anduix, B. et al. (Aug. 2001). "The Effect of Thiamine Supplementation on Tumour Proliferation. A Metabolic Control Analysis Study," *Eur. J. Biochem.* 268(15):4177-4182.

Delaney, C. A. et al. (Jul. 2000). "Potentiation of Temozolomide and Topotecan Growth Inhibition and Cytotoxicity by Novel Poly(Adenosine Diphosphoribose) Polymerase Inhibitors in a Panel of Human Tumor Cell Lines," *Clin. Cancer Res.* 6(7):2860-2867.

Fedier, A. et al. (May 2003). "The Effect of Loss of BRCA1 on the Sensitivity to Anticancer Agents in p53-Deficient Cells," *Int. J. Oncol.* 22(5):1169-1173, Abstract only located in PubMed.

Herzog, T. J. (2002). "Update on the Role of Topotecan in the Treatment of Recurrent Ovarian Cancer," *Oncologist* 7(suppl. 5):3-10.

Kuhajda, F. P. et al. (Jul. 5, 1994). "Fatty Acid Synthesis: A Potential Selective Target for Antineoplastic Therapy," *Proc. Nat'l. Acad. Sci USA* 91(14):6379-6383.

Kuhajda, F. P. et al. (Mar. 28, 2000). "Synthesis and Antitumor Activity of an Inhibitor of Fatty Acid Synthase," *Proc. Nat'l. Acad. Sci USA* 97(7):3450-3454.

Lee, W.-N. et al. (Mar. 20, 1995). "Isotopomer Study of Lipogenesis in Human Hepatoma Cells in Culture: Contribution of Carbon and Hydrogen Atoms from Glucose," *Anal. Biochem.* 226(1):100-112.

Lee, W.-N. et al. (Sep.-Dec. 1996). "Mass Isotopomer Study of Glutamine Oxidation and Synthesis in Primary Culture of Astrocytes," *Dev. Neurosci.* 18(5-6):469-477.

Lee, W.-N. et al. (May 1998). "Mass Isotopomer Study of the Nonoxidative Pathways of the Pentose Cycle with [$1,2-^{13}C_2$] Glucose," *Am. J. Physiol. Endocrinol. Metab.* 274(5 Pt 1):E843-E851.

Lee, W.-N. et al. (Aug. 14, 1998). "Fatty Acid Cycling in Human Hepatoma Cells and the Effects of Troglitazone," *J. Biol. Chem.* 273(33):20929-20934.

Leimer, K. R. et al. (Aug. 21, 1977). "Complete Mass Spectra of N-Trifluoroacetyl-*n*-Butyl Esters of Amino Acids," *J. Chromatography* 141(2):121-144.

Loftus, T. M. et al. (Jun. 30, 2000). "Reduced Food Intake and Body Weight in Mice Treated with Fatty Acid Synthase Inhibitors," *Science* 288(5475):2379-2381.

Menendez, J. A. et al. (Apr. 1, 2005). "Does Endogenous Fatty Acid Metabolism Allow Cancer Cells to Sense Hypoxia and Mediate Hypoxic Vasodilation? Characterization of a Novel Molecular Connection Between Fatty Acid Synthase (FAS) and Hypoxia-Inducible Factor-1α (HIF-1α)-Related Expression of Vascular Endothelial Growth Factor (VEGF) in Cancer Cells Overexpressing Her-2/*neu* Oncogene," *J. Cell Biochem* 94(5):857-863.

Menendez, J. A. et al. (Jul./Aug. 2005). "Targeting Fatty Acid Synthase: Potential for Therapeutic Intervention in Her-2/*neu*-Overexpressing Breast Cancer," *Drug News & Perspective* 18(6):375-385.

Pizer, E. S. et al. (Jun. 15, 1996). "Inhibition of Fatty Acid Synthesis Induces Programmed Cell Death in Human Breast Cancer Cells," *Cancer Res.* 56(12):2745-2747.

Powell, S. N. et al. (Sep. 1, 2003). "Roles of BRCA1 and BRCA2 in Homologous Recombination, DNA Replication Fidelity and the Cellular Response in Ionizing Radiation," *Oncogene* 22(37):5784-5791.

Ries, L. A. G. et al. (eds). (2007) SEER Cancer Statistics Review, 1975-2004, National Cancer Institute. Bethesda, MD, based on Nov. 2006 SEER data submission, posted to the SEER web site, 2007, located at http://seer.cancer.gov/csr/1975_2004/, 3 pages.

Sabate, L. et al. (Jan. 12, 1995). "A Model of the Pentose Phosphate Pathway in Rat Liver Cells," *Mol. Cell Biochem.* 142(1):9-17.

Written Opinion of the International Search Authority mailed on Jun. 16, 2008, for PCT Application No. PCT/US07/77651 filed on Sep. 5, 2007, 4 pages.

Written Opinion of the International Search Authority mailed on Dec. 3, 2007, for PCT Application No. PCT/US07/71053 filed on Jun. 12, 2007, 5 pages.

Non Final Office Action mailed on Dec. 2, 2009, for U.S. Appl. No. 11/850,626, filed Sep. 5, 2007, 8 pages.
Non Final Office Action mailed on Aug. 11, 2009, for U.S. Appl. No. 12/269,024, filed Nov. 11, 2008, 13 pages.
Non Final Office Action mailed on Mar. 4, 2010, for U.S. Appl. No. 12/269,833, filed Nov. 12, 2008, 25 pages.
U.S. Appl. No. 12/748,209, filed Mar. 26, 2010, for Ossovskaya et al.
Bryant, H.E. et al. (2004). "Poly(ADP-ribose) Polymerase Inhibiotrs as Potential Chemotherapeutic Agents," *Biochemical Society Transactions* 32(6):959-961.
Carey, L.A. (2010). "Directed Therapy of Subtypes of Triple Negative Breast Cancer," *The Oncologist* 15(Supplement 3 Preview):8-15.
O'Shaughnessy, J. (2010). "Triple Negative Breast Cancer: The Emerging Treatment with BSI-201 (Iniparib)," *The Oncologist* 15(Supplement 3 Preview):1-7.
Astrazeneca International. Gefitinib (IRESSA™) Lung Cancer ISEL Trial shows no overall surival advantage in a highly refractory population. Press release, Dec. 17, 2004. Available at: http://www.astrazeneca.com/pressrelease/4245.aspx Last accessed Mar. 4, 2008.
Banker, et al. Ed. Modern Pharmaceutics, Third Edition. Marcel Dekker, New York. 1996:596.
Bigler, et al. Evaluation of tamoxifen in persistent or recurrent nonsquamous cell carcinoma of the cervix: a Gynecologic Oncology Group study. International Journal of Gynecological Cancer 2004;14(5):871-874.
Chen, et al, Potential for selective modulation of glutathione in cancer chemotherapy. Chem Biol Interact 1998; 111-112:263-75.
Chustecka, Z. Adding Bevacizumab Not Beneficial in Pancreatic Cancer, 2007 Gastrointestinal Cancers Symposium. Presented Jan. 20, 2007.
Crowson, et al. A phase II study to evaluate tamoxifen in pancreatic adenocarcinoma. Eur J Surg Oncol, 1986; 12(4).335-6.
Dongiovanni, et al. Gefitinib (ZD1839); Therapy in selected patients with non-small cell lung, cancer (NSCLC)? Lung Cancer. Feb. 1, 2008 [Epub ahead of print] Availabel at: http://www.ncbi.nlm.nih.gov/pubmed/18243402 Last accessed Mar. 5, 2008.
Duell, et al. A population-based study of the Arg399Gln polymorphism in X-ray repair cross-complementing group 1 (XRCC1) and risk of pancreatic adenocarcinoma. Cancer Res 2002; 62;4634-6.
Early Breast Cancer Trialists' Collaborative Group. Tamoxifen for early breast cancer. The Cochrane Database of Systematic Reviews 2008 Issue 1. Available at: http://www.cochrane.org/review/en/ab000486.html. Last accessed Mar. 4, 2008.
Edwards, et al. Resistance to therapy caused by intragenic deletion in BRCA2. Nature, 2008: 451(7182):1111-5.
Erowid, Introduction to the Federal Controlled Substance Analogue Act. 2001. Available at ttp://www.erowid.org/psychoactives/law/analog/analog_info1.shtml. Accessed Oct. 13, 2006, (4 pages).
Fierce Biotech. Avastin encounters rare failure for pancreatic cancer. Fierce Biotech Web site. Jun. 26, 2006. Available at: http://www.fiercebiotech.com/story/avastin-encounters-rare-failure-for-pancreatic-cancer/2006-06-27 Last accessed Mar. 4, 2008.
Fisher, et al. Endometrial cancer in tamoxifen-treated breast cancer patients: findings from the National Surgical Adjuvant Breast and Bowel Project (NSABP) B-14, J Natl Cancer Inst 1994; 86:527-37.
Greenfacts.org. Definition of Solid Cancer. 1 page. Feb. 1, 2002. Accessed at: http://www.greenfacts.org/glossary/pqrs/solid-cancer.htm.
Gurpide, E. Endometrial Cancer: Biochemical and Clinical Correlates. J Natl Cancer Inst 1991; 83(6): 405-416.
Hegi, et al. MGMT gene silencing and benefit from temozolomide in ghoblastoma. N Engl J Med. 2005 10:352(10):997-1003.
Ishii, et al. Efficacy of temozolomide is correlated with 1p loss and methylation of the deoxyribonucleic acid repair gene MGMT in malignant gliomas. Neurol Med Chir (Tokyo). 2007; 47(8):341-9.
Kume, et al. Mutations in the serine protease inhibitor Kazal type 1 (SPINK1) gene in Japanese patients with pancreatitis. Pancreatology 2005; 5:354-60.
Kurman, R.J. Blaustein's Pathology of the Female Genital Tract. 4th ed. Springer-Verlag. New-York 1994.
Li, et al. Pancreatic cancer, Lancet 2004; 363:1049-57.

Marchesi, et al. Triazene compounds: mechanism of action and related DNA repair systems. Pharmacol Res. 2007; 56(4):275-87.
Mendeleyev, et al. Potential chemotherapeutic activity of 4-iodo-3-nitroberizamide. Metabolic reduction to the 3-nitroso derivative and induction of cell death in tumor cells in culture. Biochem Pharmacol. 1995; 50(5):705-14.
National Cancer Institute. Bevacizumab Combined with Chemotherapy Improves Progression-Free Survival for Patients with Advanced Breast Cancer. U.S. National Institutes of Health. 2005, Available at: http://www.cancer.gov/newscenter/pressreleases/AvastinBreast. Last Accessed Mar. 4, 2008.
Paez, et al. EGFR mutations in lung cancer: correlation with clinical response to gefitinib therapy. Science, 2004 4:304(5676):1497-500.
Palmer, et al. Hypoxia-selective antitumor agents. 9. Structure-activity relationships for hypoxia-selective cytotoxicity among analogues of 5-[N,N-bis(2-chloroethyl)amino]-2,4-dinitrobenzamide. J Med Chem. 1994; 37(14):2175-84. (p. 2175 only).
Pao, et al. EGF receptor gene mutations are common in lung cancers from "never smokers" and are associated with sensitivity of tumors to gefitinib and erlotinib. Proc Natl Acad Sci U S A. Sep. 7, 2004;101(36):13306-11.
Porta, et al. Serum concentrations of organochlorine compounds and K-ras mutations in exocrine pancreatic cancer. PANKRAS II Study Group, Lancet, 1999; 354:2125-9.
Rice, et al. Induction of Endonuclease-Mediated Apoptosis in Tumor Cells by C-Nitroso- Substituted Ligands of Poly (ADP-Ribose) Polymerase. Proceedings of the National Academy of Sciences, 1992; 89:7703-7707.
Roche—Media News. US Phase III study of Avastin in advanced pancreatic cancer does not meet primary endpoint. Basel, Jun. 27, 2006. Roche Web site. Available at: htt://www.roche.com/home/media/med-cor/med-cor-2006/med-cor-2006-06-27.htm?printout=1 Last accessed Mar. 4, 2008.
Sakai, et al. Secondary mutations as a mechanism of cisplatin resistance in BRCA2-mutated cancers. Nature. Feb. 10, 2008;451:1116-21.
Shah, et al. Selenium disrupts estrogen receptor (alpha) signaling and potentiates tamoxifen antagonism in endometrial cancer cells and tamoxifen-resistant breast cancer cells. Mol Cancer Ther. 2005; 4(8):1239-49.
Shaw, et al. Practice parameters in adults with suspected or known supratentorial nonoptic pathway low-grade glioma. Neurosurg. Focus. 4(6), Article 10, 1998.
Tuma, et al. Targeting DNA Repair in BRCA Mutation Carriers. Oncology Times. Sep. 25, 2007; 29(18):52-53.
Wiewrodt, et al. MGMT in primary and recurrent human glioblastomas after radiation and chemotherapy and comparison with p53 status and clinical outcome. Int J Cancer. Mar. 15, 2008; 122(6);1391-9.
Williams, et al. Tamoxifen for relapse of ovarian cancer. Cochrane Database of Systematic Reviews 1998, Issue 2. Available at: http://www.cochrane.org/reviews/en/ab001034.html Last accessed Mar. 4, 2008.
Wolff, M. E. Ed. Burger's Medicinal Chemistry and Drug Discovery, Fifth Edition, vol. 1: Principles and Practice. John Wiley & Sons, 1995:975-977.
Bangham, A.D., et al. Diffusion of univalent ions across the lamellae of swollen phospholipids. J. Mol. Biol. 1965; 13: 238-252.
De Murcia, et al. Poly(ADP-ribose) polymerase: a molecular nick-sensor. Trends Biochem Sci. 1994; 19:172-176.
Desmarais, et al. Enzymological properties of poly(ADP-ribose)polymerase: characterization of automodification sites and NADase activity. Biochim. Biophys. Acta. 1991, 1078: 197-186.
El-Khamisy, et al. A requirement for PARP-1 for the assembly or stability of XRCCI nuclear foci at sites of oxidative DNA damage, Nucleic Acid Res. 2003; 31(19): 5526-5533.
Fojo, et al. Amplification of DNA sequences in human multidrug-resistant KB carcinoma cells. Proc Natl Acad Sci U S A. 1985; 82(22):7661-5.
Goodman, et al. Eds. The Pharmacological Basic of Therapeutics. 11th ed. Brunton, et al. eds. McGraw-Hall. New York. 2006.

Gradwohl, et al. The second zinc-finger domain of poly(ADP-ribose) polymerase determines specificity for single-stranded breaks in DNA. Proc. Natl. Acad. Sci. USA 1990; 87:2990-2994.

Jaboin, et al. MS-27-275, an inhibitor of histone deacetylase, has marked in vitro and in vivo antitumor activity against pediatric solid tumors, Cancer Research. 2002; 62:6108-6115.

Kerley-Hamilton, et al. A p53-dominant transcriptional response to cisplatin in testicular germ cell tumor-derived human embyronal carcinoma, Oncogene 2005; 24:6090-6100.

Masson, et al. XRCC1 is specifically associated with poly(ADP-ribose) polymerase and negatively regulates its activity following DNA damage. Mol Cell Biol. 1998; 18(6):3563-3571.

Masutani, et al. Poly(ADP-ribose) and carcinogenesis, Genes, Chromosomes, and Cancer. 2003; 6:339-348.

O'Brien, et al. Investigation of the Alamar Blue (resazurin) fluorescent dye for the assessment of mammalian cell cytotoxicity. Eur J Biochem. 2000; 267(17):5421-6.

Okano, et al. Spatial and temporal cellular responses to single-strand breaks in human cells. Mol Cell Biol. 2003; 23(11): 3974-3981.

Park, et al. Induction of apoptosis and inhibition of cyclooxygenase-2 expression by N-methyl-N'-nitro-N-nitrosoguanidine in human leukemia cells, Anti-Cancer Drugs. 2005; 16(5):507-13.

Remington's Pharmaceutical Sciences. Latest edition. Mack Publishing Co. Easton, P.

Ruscetti, et al. Stimulation of the DNA-dependent protein kinase by poly(ADP-ribose) polymerase. J. Biol. Chem. 1998; 273; 14461-14467.

Saito, et al. A synthetic inhibitor of histone deacetylase, MS-27-275, with marked in vivo antitumor activity against human tumors, Proc. National Acad. Sci. 1999; 96:4592-4597.

Shall, et al. Poly(ADP-ribose) polymerase-1: what have we learned from the deficient mouse model? Mutat Res. 2000; 460(1):1-15.

Shen, et al. Multiple drug-resistant human KB carcinoma cells independently selected for high-level resistance to colchicine, adriamycin, or vinblastine show chanses in expression of specific proteins. J Biol Chem. Jun. 15, 1986; 261(17):7762-70.

Simonin, et al. The carboxyl-terminal domain of human poly(ADP-ribose) polymerase. Overproduction in *Escherichia coli*, large scale purification, and characterization, J. Biol. Chem. 1993; 268: 13454-13461.

Szoka, et al. Procedure for preparation of liposomes with large internal aqueous space and high capture by reverse-phase evaporation. Proc. Nat'l Acad. Sci. 1978; 75(9): 4194-4198.

Anders, C. at al. (Oct. 2008). "Understanding and Treating Triple-Negative Breast Cancer," *Oncology* 22(11):1233-1243.

Behrens, P. et al. (2001). "Invasive Properties of Serous Human Epithelial Ovarian Tumors are Related to Ets-1, MMP-1 and MMP-9 Expression," *Int. J. Mol. Med.* 8:149-154.

Behrens, P. et al. (2001). "The Ets-1 Transcription Factor is Up-Regulated Together with MMP 1 and MMP 9 in the Stroma of Pre-Invasive Breast Cancer," *J. Pathol.* 194:43-50.

Bischoff, J. R. et al. (Nov. 1999). "The Aurora/1p12p Kinase Family: Regulators of Chromosome Segregation and Cytokinesis," *Trends Cell Biol.* 9:454-459.

Blakeley, J. O. et al. (Jun. 5, 2010). "Poly (ADP-ribose) Polymerase-1 (PARP1) Inhibitor BSI-201 in Combination with Temozolomide (TMZ) in Malignant Gilmoa," *J. Clin. Oncol.* 28(15)(May 20 Supplement):2012, also located at *ASCO Annual Meeting Proceedings* (*Post-Meeting Edition*) located at http://meeting.ascopubs.org/cgi/content/abstract/28/15_suppl/2012, 2 pages.

Bohula, E. A. et al. (Oct. 2003). "Targeting the Type 1 Insulin-like Growth Factor Receptor as Anti-Cancer Treatment," *Anti-Cancer Drugs* 14(9):669-682.

Bold, R. J. et al. (Sep. 2001). "Chemosensitization of Pancreatic Cancer by Inhibition of the 26S Proteasome," *J. Surg. Res.* 100(1):11-17.

Castro, M. et al. (2010). "Pharmacokinetics of BSI-201, a Poly (ADP-ribose) Polymerase-1 (PARP1) Inhibitor, in Cerebrospinal Fluid (CSF) of a Patient with Breast Cancer with Carcinomatous Meningitits," *J. Clin. Oncol.* 28-Supplemental, Abstract No. e13559, 2 pages.

Chang, W. et al. (Dec. 14, 2001). "The Sequence-specific DNA Binding of NF-κB is Reversibly Regulated by the Automodification Reaction of Poly (ADP-ribose) Polymerase 1," *J. Biol. Chem.* 276(50):47664-47670.

Clinical Trial Registry NCT 00298675 (Mar. 2006). "Phase 1/1b Dose Escalation Study Evaluating BSI-201 as a Single Agent and in Combination With Irinotecan in Subjects With Advanced Solid Tumors," located at http://clinicaltrials.gov/ct2/show/NCT00298675, last visited on Oct. 27, 2010, first received on Mar. 1, 2006; last updated on Jun. 14, 2010, 5 pages.

Clinical Trial Registry NCT 00422682 (Jan. 2007). "A Study Evaluating BSI-201 in Combination With Chemotherapeutic Regimens in Subjects With Advanced Solid Tumors," located at http://clinicaltrials.gov/ct2/show/NCT00422682, last visited on Oct. 27, 2010, first received on Jan. 12, 2007, last updated on Jun. 14, 2010, 6 pages.

Clinical Trial Registry NCT 00540358 (Oct. 2007). "A Phase 2 Trial of Standard Chemotherapy, With or Without BSI-201, in Patients With Triple Negative Metastatic Breast Cancer," located at http://clinicaltrials.gov/ct2/show/NCT00540358, last visited on Oct. 27, 2010, first received on Oct. 4, 2007, last updated on Jun. 14, 2010, 7 pages.

Clinical Trial Registry NCT 00687765 (May 2008). "Study of the Poly (ADP-ribose) Polymerase-1 (PARP-1) Inhibitor BSI-201 in Patients With Newly Diagnosed Malignant Glioma," located at http://clinicaltrials.gov/ct2/show/NCT00687765, last visited on Oct. 27, 2010, first received on May 28, 2008, last updated on Jun. 14, 2010, 6 pages.

Clinical Trial Registry NCT 00687687 (May 2008). "Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma," located at http://clinicaltrials.gov/ct2/show/NCT00687687, last visited on Oct. 27, 2010, first received on May 28, 2008, last updated on Jun. 14, 2010, 5 pages.

Clinical Trial Registry NCT 00677079 (May 2008). "Single Arm Study of BSI-201 in Patients With BRCA-1 or BRCA-2 Associated Advanced Epithelial Ovarian, Fallopian Tube, or Primary Peritoneal Cancer," located at http://clinicaltrials.gov/ct2/show/NCT00677079, last visited on Oct. 27, 2010, first received on May 9, 2008, last updated on Jun. 14, 2010, 5 pages.

Clinical Trial Registry NCT 00813956 (Dec. 2008). "A Phase 2 Study of Standard Chemotherapy Plus BSI-201 (a PARP Inhibitor) in the Neoadjuvant Treatment of Triple Negative Breast Cancer," located at http://clinicaltrials.gov/ct2/show/NCT00813956, last visited on Oct. 27, 2010, first received on Dec. 19, 2008, last updated on Jun. 14, 2010, 5 pages.

Clinical Trial Registry NCT 00938652 (Jul. 10, 2009). "A Phase 3, Multi-Center Study of Gemcitabine/Carboplatin, With or Without BSI-201, in Patients With ER-, PR-, and Her2-Negative Metastatic Breast Cancer," located at http://clinicaltrials.gov/ct2/show/NCT00938652, last visited on Oct. 27, 2010, first received on Jul. 10, 2009, last updated on Jun. 14, 2010, 7 pages.

Clinical Trial Registry NCT 01033292 (Dec. 2009). "A Single-Arm Study Evaluating Carboplatin/Gemcitabine in Combination With BSI-201 in Patients With Platinum-Resistant Recurrent Ovarian Cancer," located at http://clinicaltrials.gov/ct2/show/NCT01033292, last visited on Oct. 27, 2010, first received on Dec. 14, 2009, last updated on Jun. 14, 2010, 6 pages.

Clinical Trial Registry NCT 01033123 (Dec. 2009). "A Single-Arm Study Evaluating Carboplatin/Gemcitabine in Combination With BSI-201 in Patients With Platinum-Sensitive Recurrent Ovarian Cancer," located at http://clinicaltrials.gov/ct2/show/NCT01033123, last visited on Oct. 27, 2010, first received on Dec. 14, 2009, last updated on Jun. 14, 2010, 6 pages.

Clinical Trial Registry NCT 01045304 (Jan. 2010). "Study of SAR240550 (BSI-201) in Combination With Gemcitabine/Carboplatin, in Patients With Metastatic Triple Negative Breast Cancer," located at http://www.clinicaltrials.gov/ct2/show/NCT01045304, last visited on Oct. 27, 2010, first received on Jan. 7, 2010, last updated on Sep. 2, 2010, 7 pages.

Clinical Trial Registry NCT 01082549 (Mar. 2010). "Trial of Gemcitabine/Carboplatin With or Without BSI-201 (a PARP1 Inhibitor) in Patients With Previously Untreated Advanced Squamous Cell Lung Cancer," located at http://clinicaltrials.gov/ct2/show/NCT01082549, last visited on Oct. 27, 2010, first received on Mar. 5, 2010, last updated on Aug. 30, 2010, 7 pages.

Clinical Trial Registry NCT 01130259 (May 2010). "An Open-Label, Expanded Access Protocol of Iniparib Breast Cancer," located at http://clinicaltrials.gov/ct2/show/NCT01130259, last visited on Oct. 27, 2010, first received on May 24, 2010, with no changes posted, 3 pages.

Clinical Trial Registry NCT 01173497 (Jul. 2010). "A Study Evaluating INIPARIB in Combination With Chemotherapy to Treat Triple Negative Breast Cancer Brain Metastasis," http://clinicaltrials.gov/ct2/show/NCT01173497, last visited on Oct. 27, 2010, first received on Jul. 28, 2010, last updated on Jul. 29, 2010; 5 pages.

Clinical Trial Registry NCT 01161836 (Aug. 2010). An Open-label Study Investigating the Disposition and QT/QTc Interval Effects of 400 mg [14C]-Iniparib(3.7 MBq, 100 µCi), located at http://clinicaltrials.gov/ct2/show/NCT01161836, last visited on Oct. 27, 2010, first received on Jul. 12, 2010, last updated on Aug. 20, 2010, 5 pages.

Clinical Trial Registry NCT 01086254 (Oct. 2010). "SAR240550 in Combination With Gemcitabine/Cisplatin in Non-small Cell Lung Cancer," located at http://clinicaltrials.gov/ct2/show/NCT01086254, last visited on Oct. 27, 2010, first received on Mar. 11, 2010, last updated on Aug. 17, 2010, 7 pages.

Cohen-Armon, M. (2007). "PARP-1 Activation in the ERK Signaling Pathway," *Trends Pharmacol. Sci.* 28(11):556-560.

Cory, S. et al. (2003). "The Bcl-2 Family: Roles in Cell Survival and Oncogenesis," *Oncogene* 22:8590-8607.

Curtin, N.J. (Mar. 15, 2005). "PARP Inhibitors for Cancer Therapy," *Expert. Rev. Mol. Med.* 7(4):1-20.

Cusack, J. C. et al. (May 1, 2001). "Enhanced Chemosensitivity to CPT-11 with Proteasome Inhibitor PS-341: Implications for Systemic Nuclear Factor-κB Inhibition," *Cancer Res.* 61:3535-3540.

Dittmer, J. (Aug. 20, 2003). "The Biology of the Ets1 Proto-Oncogene," *Mol. Cancer*, available at http://www.molecular-cancer.com/content/2/1/29, 2(29):1-21.

Dwyer, J. et al. (2007). "Transcriptional Regulation of Telomerase Activity: Roles of the the Ets Transcription Factor Family," *Ann. New York Acad. Sci.* 1114:36-47.

Fischer, F. et al. (Dec. 2007). "5-Fluorouracil is Efficiently Removed from DNA by the Base Excision and Mismatch Repair Systems," *Gastroenterology* 133(6):1858-1868.

Gonzalez, R. J. et al. (2001). "Evaluation of Hepatic Subcellular Fractions for Alamar Blue and MTT Reductase Activity," *Toxicol. In Vitro* 15:257-259.

Gotlieb, W. H. et al. (2006). "Insulin-like Growth Factor Receptor I Targeting in Epithelial Ovarian Cancer," *Gynecol. Oncol.* 100:389-396.

Hagan, M. P. et al. (2007). "Radiation-Induced PARP Activation is Enhanced Through EGFR-ERK Signaling," *J. Cell Biochem.* 101:1384-1393.

Hatake, K. et al. (Apr. 2007). "Next Generation Molecular Targeted Agents for Breast Cancer: Focus on EGFR and VEGFR Pathways," *Breast Cancer* 14(2):132-149.

Hideshima, T. et al. (May 10, 2002). "NF-κB as a Therapeutic Target in Multiple Myeloma," *J. Biol. Chem.*, available at http://www.jbc.org (last visited on Aug. 31, 2010), 277(19):16639-16647.

Hirai, K. et al. (Jul. 1983). "Aberration of Poly(Adenosine Diphosphate-Ribose) Metabolism in Human Colon Adenomatous Polyps and Cancers," *Cancer Research* 43:3441-3446.

Hutcheson, I. R. et al. (2006). "Inductive Mechanisms Limiting Response to Anti-Epidermal Growth Factor Receptor Therapy," *Endocrine-Rel. Cancer* 13:S89-S97.

Jiang, Y. et al. (Sep. 7, 2001). "Invasiveness of Hepatocellular Carcinoma Cell Lines: Contribution of Hepatocyte Growth Factor, c-met, and Transcription Factor Ets-1," *Biochem. Biophys. Res. Commun.* 286(5):1123-1130.

Jones, H. E. et al. (2006). "Growth Factor Receptor Interplay and Resistance in Cancer," *Endocrine-Rel. Cancer* 13:S45-S51.

Kang, S. P. et al. (Feb. 2008). "Triple Negative Breast Cancer: Current Understanding of Biology and Treatment Options," *Curr. Opin. Obstet. Gynecol.* 20(1):40-46.

Karamouzis, M. V. et al. (Jul. 4, 2007). "Therapies Directed Against Epidermal Growth Factor Receptor in Aerodigestive Carcinomas," *JAMA* 298(1):70-82.

Kari, C. et al. (Jan. 1, 2003). "Targeting the Epidermal Growth Factor Receptor in Cancer: Apoptosis Takes Center Stage," *Cancer Res.* 63:1-5.

Kelly, E. A. B. et al. (2000). "Increased Matrix Metalloproteinase-9 in the Airway After Allergen Challenge," *Am. J. Resp. Crit. Care Med.* 162:1157-1161.

Khan, Z. A. et al. (2006). "Therapeutic Targeting of Endothelial Dysfunction in Chromic Diabetic Complications," *Recent Patents in Cardiovascular Drug Discovery* 1:167-175.

Khandwala, H. M. et al. (2000). "The Effects of Insulin-Like Growth Factors on Tumorigenesis and Neoplastic Growth," *Endo. Rev.* 21(3):215-244.

Kimura, M. et al. (May 23, 1997). "Cell Cycle-dependent Expression and Spindle Pole Localization of a Novel Human Protein Kinase, Aik, Related to Aurora of *Drosophila* and Yeast Ipl1," *J. Biol. Chem.*, available at http://www.jbc.org (last visited on Sep. 7, 2010), 272(21):13766-13771.

Kitange, G. et al. (Apr. 1999). "Ets-1 Transcription Factor-Mediated Urokinase-Type Plasminogen Activator Expression and Invasion in Glioma Cells Stimulated by Serum and Basic Fibroblast Growth Factors," *Lab. Invest.* 79(4):407-416.

Kopetz, S. et al. (May 20, 2008). "First Human Phase I Study of BSI-201, a Small Molecule Inhibitor of Poly ADP-Ribose Polymerase (PARP) in Subjects with Advanced Solid Tumors," *J. Clin. Oncol.* 26(Supplemental), Abstract No. 3577, 3 pages.

Li, Z. et al. (Jan. 1, 2005). "BCL-6 Negatively Regulates Expression of the NF-κB1 p105/p50 Subunit," *J. Immunol.* 174:205-214.

Linardopoulos, S. (Sep. 2007). Aurora-A Kinase Regulates NF-κB Activity: Lessons from Combination Studies, *J. Buon.* 12(Suppl. 1):S67-S70.

Mabuchi, S. et al. (May 28, 2004). "Inhibition of NFκB Increases the Efficacy of Cisplatin in in Vitro and in Vivo Ovarian Cancer Models," *J. Biol. Chem.*, available at http://www.jbc.org (last visited on Sep. 1, 2010), 279(22):23477-23485.

Mahaney, J. J. et al. (May 20, 2008). "A Phase IB Study Evaluating BSI-201 in Combination with Chemotherapy in Subjects with Advanced Solid Tumours," *J. Clin. Oncol.* 26(Supplemental), Abstract No. 3579, 3 pages.

Martin, S. A. et al. (Feb. 2008, e-pub. Mar. 14, 2008). "DNA Repair Deficiency as a Therapeutic Target in Cancer," *Curr. Opin. Genet. Dev.* 18(1):80-86.

Melisi, D. et al. (Oct. 2007). "The Novel Poly(ADP-ribose) Polymerase (PARP)-1 Inhibitor, BSI-401, has Antitumor Activity and Potentiates Oxaliplatin Cytotoxic Activity in Human Pancreatic Cancer," *AACR-NCI-EORTC International Conference: Molecular Targets and Cancer Therapeutics*, San Francisco, CA, Oct. 22-26, 2007, Abstract B282, located at <http://www.aacrmeetingabstracts.org/cgi/content/meeting_abstract/2007/3_Molecular_Targets_Meeting/B282?maxtoshow=&HITS=10&hits=10&RESULTFORMAT=&author1=melisi&andorexactfulltext=and&searchid=1&FIRSTINDEX=0&sortspec=relevance&resourcetype=HWCIT>, last visited on Jul. 15, 2010, 2 pages.

Melisi, D. et al. (Jan. 2009). "Antitumour Efficacy of the Novel Poly(ADP-Ribose) Polymerase (PARP-1) Inhibitor BSI-401 and Synergism with Oxaliplatin (OX) in an Orthotopic Murine Model of Pancreatic Cancer (PC)," *2009 Gastrointestinal Cancers Symposium*, located at <http://www.asco.org/ASCOv2/Meetings/Abstracts?&vmview=abst_detail_view&confID=63&abstractID=10481>, last visited on Jul. 12, 2010, Abstract No. 164, 4 pages.

Mori, N. et al. (Apr. 1, 1999). "Constitutive Activation of NF-κB in Primary Adult T-Cell Leukemia Cells," *Blood* 93(7):2360-2368.

Mori, N. et al. (Sep. 1, 2002). "Bay 11-7082 Inhibits Transcription Factor NF-κB and Induces Apoptosis of HTLV-I-Infected T-cell Lines and Primary Adult T-cell Leukemia Cells," *Blood* 100(5):1828-1834.

Moschos, S. J. et al. (2002). "The Role of the IGF System in Cancer: From Basic to Clinical Studies and Clinical Applications," *Oncology* 63:317-332.

Naito, S. et al. (2000). "Overexpression of Ets-1 Transcription Factor in Angiosarcoma of the Skin," *Pathol. Res. Pract.* 196:103-109.

Nakada, M. et al. (Apr. 1999). "Ets-1 Positively Regulates Expression of Urokinase-type Plasminogen Activator (uPA) and Invasiveness of Astrocytic Tumors," *J. Neuropathol. Exp. Neurol* 58(4):329-334.

O'Shaughnessy, J. et al. (Dec. 12, 2008). "Triple Negative Breast Cancer: A Phase 2, Multi-center, Open-label, Randomized Trial of Gemcitabine/Carboplatin (G/C), with or without BSI-201, a PARP Inhibitor," *San Antonio Breast Cancer Symposium Annual Meeting 2008*, San Antonio, TX, located at <http://www.abstracts2view.com/sabcs/view.php?nu=SABCSO8L_612&terms=>, last visited on Jul. 12, 2010, 1 page.

O'Shaughnessy, J. et al. (2009). "Efficacy of BSI-201, A Poly (ADP-ribose) Polymerase-1 (PARP1) Inhibitor, in Combination with Gemcitabine/Carboplatin (G/C) in Patients with Metastatic Triple-Negative Breast Cancer (TNBC): Results of a Randomized Phase II Trial," *J. Clinl. Oncol.* 27:182, Abstract No. 3, 4 pages.

O'Shaughnessy, J. et al. (Dec. 11, 2009). "Updated Results of a Randomized Phase II Study Demonstrating Efficacy and Safety of BSI-201, A PARP Inhibitor, in Combination with Gemcitabine/Carboplatin in Metastatic Triple-Negative Breast Cancer," *San Antonio Breast Cancer Symposium*, San Antonio, Texas, Dec. 9-13, 2009, located at <http://www.posters2view.com/sabcs09/viewp.php?nu=3122>, last visited on Jul. 12, 2010, 1 page.

Oda, N. et al. (1999). "ETS-1 Converts Endothelial Cells to the Angiogenic Phenotype by Inducing the Expression of Matrix Metalloproteinases and Integrin $\beta_3$," *J. Cell. Physiol.* 178:121-132.

Oda, K. et al. (2005). "A Comprehensive Pathway Map of Epidermal Growth Factor Receptor Signaling," *Mol. Sys. Biol.* 2005.0010:1-17.

Ossvskaya, V. et al. (Oct. 2007). "PARP1 Gene Over-expression in Primary Human Cancers: A Potential Marker for PARP Inhibition," *AACR-NCI-EORTC International Conference: Molecular Targets and Cancer Therapeutics*, San Francisco, CA, Oct. 22-26, 2007, located at <http://www.aacrmeetingabstracts.org/cgi/content/meeting_abstract/2007/3_Molecular_Targets_Meeting/C125?maxtoshow=&HITS=10&hits=10&RESULTFORMAT=&fulltext=bsi-201&andorexactfulltext=and&searchid=1&FIRSTINDEX=0&sortspec=relevance&resourcetype=HWCIT>, last visited on Jul. 15, 2010, Abstract C125, 2 pages.

Ossovskaya, V. et al. (Nov. 2007). "The PARP1 Gene is Over-expressed in Triple Negative Breast Cancer," *European Journal of Cancer Supplements* 5(8):31, Abstract No. P57.

Ossovskaya, V. et al. (Apr. 2008). "Activity of BSI-201, a Potent Poly(ADP-ribose) Polymerase (PARP1) Inhibitor, Alone and in Combination with Topotecan in Human Ovarian Xenografts," $99^{th}$ *AACR Annual Meeting*, San Diego, CA, Apr. 12-16, 2008, Abstract No. 2311 located at http://www.aacrmeetingabstracts.org/cgi/content/meeting_abstract/2008/1_Annual_Meeting/2311?maxtoshow=&HITS=10&hits=10&RESULTFORMAT=&fulltext=bsi-201&andorexactfulltext=and&searchid=1&FIRSTINDEX=0&sortspec=relevance&resourcetype=HWCIT, last visited on Jul. 15, 2010, 2 pages.

Ossovskaya, V. et al. (Apr. 22, 2009). "BSI-201 Enhances the Activity of Multiple Classes of Cytotoxic Agents and Irradiation in Triple Negative Breast Cancer," *2009 AACR Annual Meeting*, Denver, CO, Apr. 18-22, 2009, located at http://www.abstractsonline.com/viewer/viewAbstract.asp?CKey=%7BA98A01B0-1623-4F71-99C7-FCE19F299C1F%7D&MKey=%7BD007B270-E8F6-492D-803B-7582CE7A0988%7D&AKey=%7B728BCE9C-121B-46B9-A8EE-DC51FDFC6C15%7D&SKey=%7BCCA05FCE-642E-4E26-AD12-29C831335BE1%7D, last visited on Jul. 12, 2010, 2 pages.

Parker, J. S. et al. (Mar. 10, 2009). "Supervised Risk Predictor of Breast Cancer Based on Intrinsic Subtypes," *J. Clin. Oncol.* 27(8):1160-1167.

Pollak, M. N. et al. (Jul. 2004). "Insulin-like Growth Factors and Neoplasia," *Nature Rev. Cancer* 4(7):505-518.

Prat, A. et al. (2010). "Deconstructing the Molecular Portraits of Breast Cancer," *Molecular Oncology* XXX:1-18 (doi:10/1016/j.molonc.2010.04.003).

Riedemann, J. et al. (2006). "IGF1R Signalling and Its Inhibition," *Endocr. Relat. Cancer* 13:S33-S43.

Roberts, R. B. et al. (Feb. 5, 2002). "Importance of Epidermal Growth Factor Receptor Signaling in Establishment of Adenomas and Maintenance of Carcinomas During Intestinal Tumorigenesis," *PNAS* 99(3):1521-1526.

Rocha-Lima, C. M. et al. (Jul. 2007). "EGFR Targeting of Solid Tumors," *Cancer Control* 14(3):295-304.

Rodon, J. et al. (Jan. 2009). "Development of PARP Inhibitors in Oncology," *Expert Opin. Investig. Drugs* 18(1):31-43.

Sato, Y. et al. (2000). "Signal Transduction and Transcriptional Regulation of Angiogenesis," in *Angiogenesis From the Molecular to Integrative Pharmacology*, Maragoudakis, M.E. ed., Kluwer Academic/Plenum Publishers, New York, NY, 476:109-115.

Sementchenko, V. I. et al. (2000). "Ets Target Genes: Past, Present and Future," *Oncogene* 19:6533-6548.

Sequist, L. V. (2007). "Second-Generation Epidermal Growth Factor Receptor Tyrosine Kinase Inhibitors in Non-Small Cell Lunch Cancer," *Oncologist*, available at http://www.TheOncologist.com (last visited on Sep. 1, 2010), 12:325-330.

Sestili, P. et al. (1990). "Structural Requirements for Inhibitors of Poly(ADP-ribose) Polymerase," *J. Cancer. Res. Clin. Oncol.* 116:615-622.

Shah, S. A. et al. (2001). "26S Proteasome Inhibition Induces Apoptosis and Limits Growth of Human Pancreatic Cancer," *J. Cell Biochem.* 82:110-122.

Sharrocks, A. D. et al. (1997). "The ETS-domain Transcription Factor Family," *Int. J. Biochem. Cell. Biol.* 29(12):1371-1387.

Shiu, K.K. et al. (Sep. 2008). "Development of Therapeutic Approaches to 'Triple Negative' Phenotype Breast Cancer," *Expert Opin. Ther. Targets* 12(9):1123-1137.

Sørlie, T. et al. (Sep. 11, 2001). "Gene Expression Patterns of Breast Carcinomas Distinguish Tumor Subclasses with Clinical Implications," *Proc. Natl. Acad. Sci. USA* 98(19):10869-10874.

St-Pierre, Y. et al. (2004). "Regulation of MMP-9 Gene Expression for the Development of Novel Molecular Targets Against Cancer and Inflammatory Diseases," *Expert Opin. Therp. Targets* 8(5):473-489.

Takanami, I. et al. (2001). "Expression of Ets-1 is Correlated with Urokinase-Type Plasminogen Activator and Poor Prognosis in Pulmonary Adenocarcinoma," *Tumor Biol.* 22:205-210.

Tong, Q. et al. (Mar. 2, 2006). "VEGF is Upregulated by Hypoxia-induced Mitogenic Factor via the PI-3K/Akt-NF-κB Signaling Pathway," *Respir. Res.* 7(37):1-14.

Toshi, L. et al. (2007). "Understanding the New Genetics of Responsiveness to Epidermal Growth Factor Receptor Tyrosine Kinase Inhibitors," *Oncologist* 12:211-220.

Wang, T-L. et al. (Mar. 2, 2004). "Digital Karyotyping Identifies Thymidylate Synthase Amplification as a Mechanism of Resistance to 5-Fluorouracil in Metastatic Colorectal Cancer Patients," *Proc. Natl. Acad. Sci. USA* 101(9):3089-3094.

Werner, H. et al. (2003). "The *IGF1* Receptor Gene: A Molecular Target for Disrupted Transcription Factors," *Genes, Chromo. Cancer* 36:113-120.

Woodhouse, B.C. et al. (Jul. 1, 2008, e-pub. May 12, 2008). "Poly ADP-ribose Polymerase-1: An International Molecule of Mystery," *DNA Repair (Amst.)* 7(7):1077-1076.

Xie, Z. et al. (Jun. 7, 2007). "A Multiplex RT-PCR for Simultaneous Differentiation of Three Viral Pathogens of Penaeid Shrimp," *Dis. Aquat. Organ.* 76:77-80.

Yang, J. et al. (Feb. 1, 2006). "BMS-345541 Targets Inhibitor of κB Kinase and Induces Apoptosis in Melanoma: Involvement of Nuclear Factor κB and Mitochondria Pathways," *Clin. Cancer Res.* 12(3):950-960.

Zingarelli, B. et al. (1997). "Protection Against Myocardial lschemia and Reperfusion Injury by 3-Aminobenzamide, an Inhibitor of Poly (ADP-ribose) Synthetase," *Cardiovascular Research* 36:205-215.

International Search Report mailed on Jun. 18, 2008, for PCT Patent Application No. PCT/US07/77662 filed on Sep. 5, 2007, published on Mar. 13, 2008, for PCT Publication No. WO 2008/30891, 2 pages.

Written Opinion mailed on Jun. 18, 2008, for PCT Patent Application No. PCT/US07/77662 filed on Sep. 5, 2007, published on Mar. 13, 2008, for PCT Publication No. WO 2008/30891, 3 pages.

Written Opinion mailed on Feb. 13, 2009, for PCT Application No. PCT/US08/85756 filed on Dec. 5, 2008, published on Jun. 11, 2009, as PCT Publication No. WO 2009/073869, 4 pages.

International Preliminary Report on Patentability mailed on Jun. 17, 2010, for PCT Application No. PCT/US08/85756 filed on Dec. 5, 2008, 6 pages.

International Search Report mailed on Sep. 10, 2009, for PCT Patent Application No. PCT/US09/033117, filed on Feb. 4, 2009, published on Aug. 13, 2009, as PCT Publication No. WO 2009/100159, 5 pages.

Written Opinion mailed on Sep. 10, 2009, for PCT Patent Application No. PCT/US09/033117, filed on Feb. 4, 2009, published on Aug. 13, 2009, as PCT Publication No. WO 2009/100159, 4 pages.

International Search Report mailed on Mar. 23, 2010, for PCT Patent Application No. PCT/US2010/023137 filed on Feb. 4, 2010, published on Aug. 12, 2010, as PCT Publication No. WO 2010/091140, 4 pages.

Written Opinion mailed on Mar. 23, 2010, for PCT Patent Application No. PCT/US2010/023137 filed on Feb. 4, 2010, published on Aug. 12, 2010, as PCT Publication No. WO 2010/091140, 5 pages.

Supplementary European Search Report mailed on Jul. 6, 2010, for EP Patent Application No. 07841902.5, filed on Sep. 5, 2007, 9 pages.

Supplementary European Search Report mailed on Jul. 8, 2010, for EP Patent Application No. 07875034.6, filed on Jun. 12, 2007, 14 pages.

Non Final Office Action mailed on Oct. 8, 2010, for U.S. Appl. No. 12/269,833, filed Nov. 12, 2008, 19 pages.

Licht, S. et al. (Oct. 28, 2011). "Mechanism of Action of Iniparib: In Vitro Studies in a Breast Cancer Cell Line," poster presented by Sanofi-Oncology, at the AACR-NCI-EORTC meeting, held in San Francisco, CA, USA, on Nov. 12-16, 2011, 17 pages, A226 (Poster).

Liu, X. et al. (Jan. 15, 2012, e-pub. : Nov. 29, 2011). "Iniparib Non-Selectively Modifies Cysteine-Containing Proteins in Tumor Cells and Is Not a *Bona Fide* PARP Inhibitor," *Clin. Cancer Res.* 18(2) :510-523, online publication contains 44 pages.

Bakke, J. E. et al. (Jan. 1, 1988). "Metabolism of 2,6-Dichlorobenzamide in Rats and Mice," *Xenobiotica* 18(7):817-829.

Balendiran, G. K. et al. (Jan. 1, 2004). "The Role of Glutathione in Cancer," *Cell Biochemistry and Function* 22:343-352.

Canova-Davis, E. et al. (Feb. 1976). "Chemical Modification of the Tryptophan Residue in Adrenocorticotropin," *Biochem.* 15(4):921-927.

Carey, L. A. et al. (Jan. 5, 2011). "PARP and Cancer—If it's Broke, Don't Fix It," *New England J. Med.* Located at http://www.nejm.org/doi/full/10.1056/NEJMe1012546, last visited on Jan. 6, 2011, 3 pages.

Clinical Trial Registry NCT 01204125, (Sep. 13, 2010). Two Regimens of SAR240550/Weekly Paclitaxel and Paclitaxel Alone as Neoadjuvant Therapy in Triple Negative Breast Cancer Patients (SOLTI NEOPARP), located at http://clinicaltrials.gov/ct2/show/NCT01204125, last visited on Jan. 26, 2011, first received on Sep. 13, 2010, last updated on Nov. 17, 2010, 13 pages.

Clinical Trial Registry NCT 01213381, (Sep. 30, 2010). "Safety and Pharmacokinetics of SAR240550 (BSI-201) Twice Weekly in Patients With Advanced Solid Tumors," located at http://clinicaltrials.gov/ct2/show/NCT01213381, last visited on Jan. 26, 2011, first received on Sep. 30, 2010, last updated on Oct. 1, 2010, 10 pages.

Donleavy, J. J. et al. (Jul. 1, 1947). "Alkamine Esters and Amides of Some Amino-Alkylmercaptobenzoic Acids," *J. Amer. Chem. Soc.* 69(7):1781-1784.

Geissler, T. et al. (2010). "PARP Inhibitors as Agrochemically Active Substances," *PARP 2010, 18th International Conference on ADP-Ribose Metabolism*, Aug. 18-21, 2010, University of Zurich-Irchel, Zurich, Switzerland, Poster Presentation, Abstract No. P71, 3 pages.

Kopetz, S. et al. (May 20, 2008). "First in Human Phase I Study of BSI-201, a Small Molecule Inhibitor of Poly ADP-Ribose Polymerase (PARP) in Subjects with Advanced Solid Tumors," *Poster Session presented for J. Clin. Oncol.* 26(Supplemental), Abstract No. 3577, 1 page (Poster).

Maegley, K. A. et al. (2010). "An in Vitro Mechanistic Comparison of Clinical PARP Inhibitors," *PARP 2010, 18th International Conference on ADP-Ribose Metabolism*, Aug. 18-21, 2010, University of Zurich-Irchel, Zurich, Switzerland, Poster Presentation, Abstract No. P72, 3 pages.

Makarov, V. et al. (2006). "Synthesis and Antileprosy Activity of Some Dialkyldithiocarbamates," *J. Antimicrob. Chemotherapy* 57:1134-1138.

Moulder, S. et al. (Dec. 12, 2010). "[P6-15-01] A Phase 1b Study to Assess the Safety and Tolerability of the PARP Inhibitor Iniparib (BSI-201) in Combination With Irinotecan for the Treatment of Patients With Metastatic Breast Cancer (MBC)," *Abstract related to Poster Session No. 6: Treatment—Therapeutic Strategies: Novel Targets and Targeted Agents, presented at the 33rd Annual San Antonio Breast Cancer Symposium*, held on Dec. 8-12, 2010, San Antonio, Texas, , Abstract located at http://www.abstracts2view.com/sabcs10/view.php?nu=SABCS10L_1107&terms=, last visited on Dec. 22, 2010, 1 page (Abstract).

Moulder, S. et al. (Dec. 12, 2010). "[P6-15-01] A Phase 1b Study to Assess the Safety and Tolerability of the PARP Inhibitor Iniparib (BSI-201) in Combination With Irinotecan for the Treatment of Patients With Metastatic Breast Cancer (MBC)," *Poster Session No. 6: Treatment—Therapeutic Strategies: Novel Targets and Targeted Agents, presented at the 33rd Annual San Antonio Breast Cancer Symposium*, held on Dec. 8-12, 2010, San Antonio, Texas, 1 page (Poster).

Mrózek, K. et al. (Mar. 1990). "Trisomy of Chromosone 12 in a Case of Thecoma of the Ovary," *Gynecol. Oncol.* 36(3):413-416.

Mugneret, F. et al. (Jun. 1988). "Chromosones in Ewing's Sarcoma. II. Nonrandom Additional Changes, Trisomy 8 and der(16)t(1;16)," *Cancer Genet. Cytogenet.* 32(2):239-245.

Neumeister, V. et al. (Dec. 12, 2010). [P6-04-04] Hypoxia is Associated With Somatic Loss of BRCA1 Protein and Pathway Activity in Triple Negative Breast Cancer, *Abstract related to Poster Session 6: Tumor Cell and Molecular Biology: Molecular Profiles, presented at the 33rd Annual San Antonio Breast Cancer Symposium*, held on Dec. 8-12, 2010, San Antonio, Texas, 1 page (Abstract).

O'Shaughnessy, J. et al. (Oct. 2010). Final Efficacy and Safety Results of a Randomized Phase II Study of the PARP Inhibitor Iniparib (BSI-201) in Combination With Gemcitabine/Carboplatin (G/C) in Metastatic Triple Negative Breast Cancer (TNBC), *Annals of Oncology, ESMO 2010 Late-Breaking Abstracts, Presidential Symposium*, 21(8): Abstract No. LAB11, p. viii5.

O'Shaughnessy, J. et al. (Oct. 2010). "LAB11—Iniparib With Gem/Carbo, A PARP Inhibitor Strategy, in Metastatic Triple Negative Breast Cancer," & A. Awada et al. "Cationic Liposomal Paclitaxel, A Vascular Disruption Strategy in Advanced Triple Negative Breast Cancer," *Final Oral presentation presentation presented by J. O'shaughnessy et al., and A. Awada et al., at the ESMO 2010 Congress, Milan* 2010, 17 pages total.

O'Shaughnessy, J. et al. (2011). "Iniparib Plus Chemotherapy in Metastatic Triple-Negative Breast Cancer," *The New England Journal of Medicine*, 10.1056/NEJMoa1011418, and Supplementary Appendix, for a total of 14 pages.

Ossovskaya, V. et al. (2010). "Pathway Analysis of Primary Human Triple-Negative Breast Cancers," Poster Session No. 6: Tumor Cell and Molecular Biology: Molecular Profiles, presented at the 33rd Annual San Antonio Breast Cancer Symposium, San Antonio, Texas, USA, Dec. 8-12, 2010, one page (Poster).

Ossovskaya, V. et al. (2010). "[P06-04-12] Pathway Analysis of Primary Human Triple-Negative Breast Cancers," Abstract presented at the 33rd Annual San Antonio Breast Cancer Symposium, San Antonio, Texas, USA, Dec. 12, 2010, abstract located at http://www.abstracts2view.com/sabcs10/view.php?nu=SABCS1OL_423&terms=, last visited on Jan. 6, 2011, one page (Abstract).

Ossovskaya, V. et al. (2010). "Cell Cycle Effects of Iniparib, A PARP Inhibitor, in Combination With Gemcitabine and Carboplatin in the MDA-MB-468(-) Triple-Negative Breast Cancer (TNBC) Cell Line," Oral Presentation No. P05-06-09, presented at the 33rd Annual San Antonio Breast Cancer Symposium, San Antonio, Texas, USA, Dec. 8-12, 2010, one page.

Pal, S. K. et al. (2010). "Triple Negative Breast Cancer: Unmet Medical Needs," *Breast Cancer Research and Treatment* 125(3):627-636.

Phend, C. (Jan. 5, 2011). "PARP Inhibitor Shines in Triple-Negative Breast Cancer," *News Release from Medpage Today*, article located at http://www.medpagetoday.com/HematologyOncology/BreastCancer/24195, last visited on Jan. 6, 2011, 4 pages.

Sano, K. et al. (Jan. 1, 2001). "Metabolism of Sulphobromophtalein I: Positional Isomers of Sulphobromphthalein Monoglutathione Conjugate," *J. Pharmacy & Pharmacology* 53:1015-1020.

Santomauro, A. T. M. G. et al. (Sep. 1999). "Overnight Lowering of Free Fatty Acids With Acipimox Improves Insulin Resistance and Glucose Tolerance in Obese Diabetic and Nondiabetic Subjects," *Diabetes* 48:1836-1841.

Tummino, P. J. et al. (Feb. 1, 1997). "The Human Immunodeficiency Virus Type 1 (HIV-1) Nucleocapsid Protein Zinc Ejection Activity of Disulfide Benzamides and Benzisothiazolones: Correlation With Anti-HIV and Virucidal Activities," *Antimicrobial Agents and Chemotherapy* 41(2):394-400.

Wikipedia (2011). "Fatty Acid Synthesis," located at http://en.wikipedia.org/wiki/Fatty_acid_synthesis, last visited on Jan. 18, 2011, this page was created on Feb. 18, 2007, and last modified on Jan. 7, 2011 at 02:23, 2 pages.

Supplementary European Search Report mailed Dec. 13, 2010, for EP Patent Application No. 07814695.8, filed on Sep. 5, 2007, 8 pages.

European Search Opinion mailed Dec. 13, 2010, for EP Patent Application No. 07814695.8, filed on Sep. 5, 2007, 8 pages.

European Search Opinion mailed on Jul. 6, 2010, for EP Patent Application No. 07841902.5, filed on Sep. 5, 2007, 6 pages.

European Search Opinion mailed on Jul. 8, 2010, for EP Patent Application No. 07875034.6, filed on Jun. 12, 2007, 8 pages.

AAOS (Oct. 2007). "Metastatic Bone Disease," by The American Academy of Orthopaedic Surgeons, located at http://orthoinfo.aaos.org/topic.cfm?topic=A00093, last visited on Mar. 24, 2011, Grana, W. A. (ed.), 16 pages.

Baker, L. H. (2008). "Bone Tumors: Primary and Metastatic Bone Lesions," in Chapter 212 of *Cecil Medicine*, 23$^{rd}$ ed., Goldman, L. editor, published by Saunders Elsevier, pp. 1520-1522.

Dugdale, D. C. et al. (Mar. 2, 2010). "Bone Tumors," in PudMed Health, located at http://www.ncbi.nlm.nih.gov/pubmedhealth/PMH0002210/, last visited on Mar. 24, 2011, 7 pages.

Mayo Clinic (Sep. 12, 2009). "Definition of Bone Cancer," by Mayo Clinic, located at http://www.mayoclinic.com/health/bone-cancer/DS00520, last visited on Mar. 24, 2011, 2 pages.

Licht, S. et al. (Nov. 2011). "Mechanism of Action of Iniparib: Stimulation of Reactive Oxygen Species (ROS) Production in an Iniparib-Sensitive Breast Cancer Cell Line," American Association for Cancer Research, AACR-NCI-EORTC International Conference: Molecular Targets and Cancer Therapeutics, held on Nov. 12-16, 2011, in San Francisco, California, *Mol. Cancer Ther.* 10(11)(Suppl.:1):A226, abstract located at http://mct.aacrjournals.org/cgi/content/short/10/11_MeetingAbstracts/A226?rss=1, last visited on Jan. 18, 2012, one page.

Adriaenssens, E. et al. (Jan. 15, 2008). "Nerve Growth Factor Is a Potential Therapeutic Target in Breast Cancer," *Cancer Res.* 68(2):346-351.

Anders, C. K. et al. (2011). "TBCRC 018: Phase II Study of Iniparib Plus Chemotherapy in Patients With Triple Negative Breast Cancer Brain Metastases," Poster presented at the 2011 ASCO Annual Meeting, held on Jun. 3-7, 2011, in Chicago, Illinois, USA, Poster No. TPS127, 11 pages (Poster).

Anders, C. K. et al. (2011). "TBCRC 018: Phase II Study of Iniparib Plus Chemotherapy to Treat Triple-Negative Breast Cancer (TNBC) Brain Metastases (BM)," Abstract located at http://www.asco.org/portal/site/ASCOv2/template.RAW/menuitem.a1c60e38cd6d5b9f01ae0094ef37a01d/;jsessionid=n Z2GTTTVqCfvHrK9n1RTzy5JJNnXTwtkWVS4DQyxdYQBm PkTIZQ0!60961989!-1458070824?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=74495, last visited on Jul. 19, 2011, Abstract No. TPS127, 3 pages.

Anonymous, (Dec. 12, 2006). "Report of a Pancreatic Cancer Susceptibility Gene in a Unique Pancreatic Cancer Family," *Pancreatic Cancer New*, Article located at http://pathology.jhu.edu/pc/news2006.php, last visited on Jul. 19, 2011, p. 3 (out of 10 pages).

Anonymous, (Oct. 10, 2010). "Press Briefing—Day 2," Article located at http://www.esmo.org/events/milan-2010-congress/press/sunday-10-october-2010-815-900.html, last visited on Jan. 7, 2011, one page.

Anonymous, (Oct. 13, 2010). "How is Ovarian Cancer Staged?" Article located at http://www.cancer.org/cancer/ovariancancer/detailedguide/ovarian-cancer-staging, last visited on May 30, 2011, 6 pages.

Besse, B. et al. (e-pub. Jun. 7, 2011). "Results of a Randomized Phase 2 Trial of Gemcitabine/Cisplatin/Iniparib (GCI) vs Gemcitabine/Cisplatin (GC) in Patients With Stage IV NSCLC," Abstract available at http://abstracts.webges.com/myitinerary/day.html, last visited on Jun. 9, 2011, available at World Conference on Lung Cancer Abstract, Oral Session [043], Medical Oncology IV, 2 pages.

Birrer, M. J. et al. (2011). "A Phase II Trial of Iniparib (BSI-201) in Combination With Gemcitabine/Carboplatin (GC) in Patients With Platinum-Resistant Recurrent Ovarian Cancer," *Abstract presented at the 2011 ASCO Annual Meeting*, held on Jun. 3-7, 2011, Chicago, Illinois, abstract located at http://www.asco.org/portal/site/ASCOv2/template.RAW/menuitem.a1c60e38cd6d5b9f01ae0094ef37a01d/?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=82175, last visited on Aug. 2, 2011, Abstract No. 5005, 3 pages (Abstract).

Birrer, M. et al. (2011). "Preliminary Results of a Phase 2 Trial of Iniparib (BSI-201) in Combination With Gemcitabine/Carboplatin (GC) in Patients With Platinum Resistant Recurrent Ovarian Cancer," *Poster presented at the 2011 ASCO Annual Meeting*, held on Jun. 3-7, 2011, Chicago, Illinois, USA, 21 pages (Poster).

Blakeley, J. O. et al. (Jun. 5, 2010). "Poly (ADP-ribose) Polymerase-1 (PARP1) Inhibitor Iniparib (BSI-201) in Combination with Temozolomide (TMZ) in Malignant Glioma," *Poster presented at the 2010 ASCO Annual Meeting*, held on Jun. 4-8, 2010, in Chicago, Illinois, USA, 10 pages (Poster).

Bunn, P. A. et al. (2008). "Introduction," *The Oncologist* 13(Suppl. 1):1-4.

Cappuzzo, F. et al. (May 4, 2005). "Epidermal Growth Factor Receptor Gene and Protein and Gefitinib Sensitivity in Non-Small-Cell Lung Cancer," *J. Natl. Cancer Inst.* 97(9):643-655.

Chang, B.-D. et al. (Apr. 11, 2000). "Effects of $p21^{Waf1/Cip1/Sdi1}$ on Cellular Gene Epression: Implications for Carcinogenesis, Senescence, and Age-Related Diseases," *Proc. Natl. Acad. Sci. USA* 97(8):4291-4296.

Chang, B.-D. et al. (Apr. 20, 2000). "$p21^{Waf1/Cip1/Sdi1}$-Induced Growth Arrest is Associated With Depletion of Mitosis-Control Proteins and Leads to Abnormal Mitosis and Endoreduplication in Recovering Cells," *Oncogene* 19(17):2165-2170.

Chen, Y. et al. (Jul. 15, 2001). "CV706, A Prostate Cancer-Specific Adenovirus Variant, in Combination With Radiotherapy Produces Synergistic Antitumor Efficacy Without Increasing Toxicity," *Cancer Res.* 61(14):5453-5460.

Daraselia, N. et al. (2011). "Pathway Analysis of Primary Human Non-Small Cell Lung Cancer (NSCLC)," *Poster presented at the 2011 ASCO Annual Meeting*, held on Jun. 3-7, 2011, Chicago, IL, USA, Poster No. 10573, 18 pages (Poster).

Daraselia, N. et al. (2011). "Pathway Analysis of Primary Human Non-Small Cell Lung Cancer (NSCLC)," *Abstract presented at the 2011 ASCO Annual Meeting*, held on Jun. 3-7, 2011, Chicago, IL, USA, located at http://www.asco.org/portal/site/ASCOv2/template.RAW/menuitem.a1c60e38cd6d5b9f01ae0094ef37a01d/?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=81277, last visited on Aug. 2, 2011, Abstract No. 10573, 2 pages (Abstract).

Dieras, V. et al. (Dec. 8, 2011). "A Phase 2, Randomized Open-Label Study of Iniparib, Administered Either Weekly or Twice-Weekly in Combination With Gemcitabine Plus Carboplatin in Patients With Metastatic Triple-Negative Breast Cancer (mTNBC)," Poster P3-16-08 presented at the 34$^{th}$ Annual San Antonio Breast Cancer Symposium, San Antonio, Texas, USA, Dec. 6-10, 2011, 20 pages.

Enomoto, H. et al. (Dec. 2002). "Hepatoma-Derived Growth Factor is Highly Expressed in Developing Liver and Promotes Fetal Hepatocyte Proliferation," *Hepatology* 36(6):1519-1527.

Eschmann, S. M. et al. (Mar. 2006, e-pub. Nov. 4, 2005). "Is Standardised $^{18}$F-FDG Uptake Value an Outcome Predictor in Patients With Stage III Non-Small Cell Lung Cancer," *Eur. J. Nucl. Med. Mol. Imaging* 33(3):263-269.

Everett, A. D. et al. (Mar. 2000). "Hepatoma-Derived Growth Factor Stimulates Smooth Muscle Cell Growth and is Expressed in Vascular Development," *J Clin Invest.* 105(5):567-575.

Floros, K. V. et al. (Dec. 2006). "Topotecan and Methotrexate Alter Expression of the Apoptosis-Related Genes *BCL2, FAS*, and *BCL2L12* in Leukemic HL-60 Cells," *Biol. Chem.* 387:1629-1633.

Fraker, P. J. et al. (1995). "Quantification of Apoptotic Events in Pure and Heterogeneous Populations of Cells Using the Flow Cytometer," in Chapter 4 of *Methods in Cell Biol.* vol. 46, L. M. Schwartz et al. (eds.), Academic Press, San Diego, California, pp. 46:57-76.

Fürstenberger, G. et al. (May 2002). "Insulin-Like Growth Factors and Cancer," *Lancet* 3:298-302.

Giaccone, G. et al. (Nov. 2005). "EGFR Inhibitors: What We Have Learned From the Treatment of Lung Cancer," *Nat. Clin. Pract. Oncol.* 2(11):554-561.

Gorczyca, W. et al. (Apr. 15, 1993). "Detection of DNA Strand Breaks in Individual Apoptotic Cells by The in Situ Terminal Deoxynucleotidyl Transferase and Nick Translation Assays," *Cancer Res.* 53(8):1945-1951.

Han, S. W. (Apr. 10, 2005). "Predictive and Prognostic Impact of Epidermal Growth Factor Receptor Mutation in Non-Small-Cell Lung Cancer Patients Treated With Gefitinib," *J. Clin. Oncol.* 23(11):2493-2501.

Herbst, R. S. et al. (Sep. 1, 2005). "Tribute: A Phase III Trial of Erlotinib Hydrochloride (OSI-774) Combined with Carboplatin and Paclitaxel Chemotherapy in Advanced Non-Small-Cell Lung Cancer," *J. Clin. Oncol.* 23(25):5892-5899.

Hirsch, F. R. et al. (Oct. 1, 2005). "Increased Epidermal Growth Factor Receptor Gene Copy Number Detected by Fluorescence in Situ Hybridization Associates With Increased Sensitivity to Gefitinib in Patients With Bronchioloalveolar Carcinoma Subtypes: A Southwest Oncology Group Study," *J. Clin. Oncol.* 23(28):6838-6845.

Huang, S. F. et al. (Dec. 15, 2004). "High Frequency of Epidermal Growth Factor Receptor Mutations With Complex Patterns in Non-Small Cell Lung Cancers Related to Gefitinib Responsiveness in Taiwan," *Clin. Cancer Res.* 10(24):8195-8203.

Kimura, H. et al. (2006, e-pub. Oct. 24, 2006). "EGFR Mutation Status in Tumour-Derived DNA From Pleural Effusion Fluid is a Practical Basis for Predicting the Response to Gefitinib," *Br. J. Cancer* 95(10):1390-1395.

Kosaka, T. et al. (Dec. 15, 2004, e-pub. Dec. 16, 2004). "Mutations of the Epidermal Growth Factor Receptor Gene in Lung Cancer: Biological and Clinical Implications," *Cancer Res.* 64:8919-8923.

Lepourcelet, M. et al. (Jan. 2005, e-pub. Dec. 16, 2004). "Insights into Developmental Mechanisms and Cancers in the Mammalian Intestine Derived from Serial Analysis of Gene Expression and Study of the Hepatoma-Derived Growth Factor (HDGF)," *Development* 132(2):415-427.

Lin, N. U. et al. (Feb. 15, 2009, e-pub. Feb. 19, 2009). "Multicenter Phase II Study of Lapatinib in Patients With Brain Metastases from HER2-Positive Breast Cancer," *Clin. Cancer Res.* 15(4):1452-1459, electronic version is 9 pages total.

Linn, S. C. et al. (Sep. 2009). "Clinical Relevance of the Triple-Negative Breast Cancer Concept: Genetic Basis and Clinical Utility of the Concept," *Eur. J. Cancer* 45(Suppl. 1):11-26.

Lynch, T. J. et al. (May 20, 2004). "Activating Mutations in the Epidermal Growth Factor Receptor Underlying Responsiveness of Non-Small-Cell Lung Cancer to Gefitinib," *N. Engl. J. Med.* 350(21):2129-2139.

Mahany, J. J. et al. (May 20, 2008). "A Phase IB Study Evaluating BSI-201 in Combination with Chemotherapy in Subjects with Advanced Solid Tumours," Poster published by BiPar, Sciences, Abstract No. 3579, 1 page (Poster).

Melisko, M. E. et al. (2009). "Phase II Study of Irinotecan (IN) and Temozolomide (TMZ) in Breast Cancer Patients (pts) With Brain Metastases (BM) or Leptomeningeal Disease (LMD) That Has Progressed After Stereotactic Radiosurgery (SRS) or Whole Brain Radiation (WBRT)," *Abstract presented at the 2009 Breast Cancer Symposium*, General Poster Session C, Abstract located at http:// www.asco.org/portal/site/ASCOv2/template.RAW/menuitem. a1c60e38cd6d5b9f01ae0094ef37a01d/?javax.portlet. tpst=b2e033002b246c2828a46427ef37a01d_ws_RW&javax. portlet.prp_b2e033002b246c2828a46427ef37a01d_ viewID=abst_detail_rawview&javax.portlet.begCacheTok=com. vignette.cachetoken&javax.portlet.endCacheTok=com.vignette. cachetoken&index=n&confID=70&abstractID=40353, last visited May 10, 2011, Abstract No. 237, 3 pages (Abstract).

Miknyoczki, S. J. et al. (Apr. 2003). "Chemopotentiation of Temozolomide, Irinotecan, and Cisplatin Activity by CEP-6800, A Poly(ADP-Ribose) Polymerase Inhibitor," *Molecular Cancer Therapeutics* 2:371-382.

Missale, C. et al. (Apr. 1998). "Nerve Growth Factor Abrogates the Tumorigenicity of Human Small Cell Lung Cancer Cell Lines," *Proc. Natl. Acad. Sci. USA*, 95(9):5366-5371.

Mita, A. C. et al. (Jun. 3, 2011). "A Phase IB Trial of Iniparib (BSI-201) in Combination With Carboplatin and Paclitaxel in Patients With Non-Small Cell Lung Cancer (NSCLC)," Poster presented at the 2011 ASCO Annual Meeting held on Jun. 3-7, 2011, in Chicago, Illinois, Poster No. 7570, 12 pages (Poster).

Mita, A. C. et al. (2011). "A Phase IB Trial of Iniparib (BSI-201) in Combination With Carboplatin (C)/Paclitaxel (P) in Patients With Non-Small Cell Lung Cancer (NSCLC)," *Abstract presented at the 2011 ASCO Annual Meeting held on* Jun. 3-7, 2011, in Chicago, Illinois, abstract located http://www.asco.org/portal/site/ASCOv2/ template.RAW/menuitem.a1c60e38cd6d5b9f01ae0094ef37a01d/ ?javax.portlet.tpst=b2e033002b246c2828a46427ef37a01d_ws_ RW&javax.portlet.prp_b2e033002b246c2828a46427ef37a01d_ viewID=abst_detail_rawview&javax.portlet.begCacheTok=com. vignette.cachetoken&javax.portlet.endCacheTok=com.vignette. cachetoken&index=n&confID=102&abstractID=82193, last visited on Aug. 2, 2011, Abstract No. 7570, 3 pages (Abstract).

Mitsudomi, T. et al. (Apr. 10, 2005). "Mutations of the Epidermal Growth Factor Receptor Gene Predict Prolonged Survival After Gefitinib Treatment in Patients With Non-Small-Cell Lung Cancer With Postoperative Recurrence," *J. Clin. Oncol.* 23(11):2513-2520.

Mori, M. et al. (2004). "Hepatoma-Derived Growth Factor is Involved in Lung Remodeling by Stimulating Epithelial Growth," *Am. J. Respir. Cell Mol. Biol.* 30:459-469.

Nakamura, H. et al. (1989). "Partial Purification and Characterization of Human Hepatoma-Derived Growth Factor," *Clinica Chimica Acta* 183:273-284.

Nakamura, H. et al. (1994). "Molecular Cloning of Complementary DNA for a Novel Human Hepatoma-Derived Growth Factor," *J. Biol. Chem.* 269(40):25143-25149.

Nasr, F. L. et al. (Jun. 2004). "Gemcitabine Plus Caroboplatin Combination Therapy as Second-Line Treatment in Patients With Relapsed Breast Cancers," *Clin. Breast Cancer* 5(2):1 17-122.

Oliver, J. A. et al. (Sep. 15, 1998). "An Endothelial Growth Factor Involved in Rat Renal Development," *J. Clin. Invest.* 102(6):1208-1219.

O'Shaughnessy, J. et al. (2011). "Test: Tissue Confirmation of Disease Recurrence in Patients With Breast Cancer: Pooled Analysis of Two Large Prospective Studies," Abstract presented at the 2011 ASCO Annual Meeting in Jan. 1, 2011, Abstract located at <http:// abstract.asco.org/AbstView_102_78038.html>, last visited on May 10, 2011, Abstract No. 1007, 3 pages (Abstract).

O'Shaughnessy, J. et al. (2011). "A Randomized Phase III Study of Iniparib (BSI-201) in Combination With Gemcitabine/Carboplatin (G/C) in Metastatic Triple-Negative Breast Cancer (TNBC)," *Abstract presented at 2011 ASCO Annual Meeting, held on* Jun. 3-7, 2011, in Chicago, Illinois, Abstract located at http://www.asco.org/ portal/site/ASCOv2/template.RAW/menuitem. a1c60e38cd6d5b9f01ae0094ef37a01d/?javax.portlet. tpst=b2e033002b246c2828a46427ef37a01d_ws_RW&javax. portlet.prp_b2e033002b246c2828a46427ef37a01d_ viewID=abst_detail_rawview&javax.portlet.begCacheTok=com. vignette.cachetoken&javax.portlet.endCacheTok=com.vignette. cachetoken&index =n&confID=102&abstractID=78038, last visited on Aug. 2, 2011, Abstract 1007, 3 pages (Abstract).

O'Shaughnessy, J. et al. (2011). "A Randomized Phase III Study of Iniparib (BSI-201) in Combination With Gemcitabine and Carboplatin in Metastatic Triple-Negative Breast Cancer (mTNBC),"

Poster Presentation presented at 2011 ASCO Annual Meeting, held on Jun. 3-7, 2011, in Chicago, Illinois, 18 pages (Poster).

Ossovskaya, V. S. et al. (Mar. 15, 2009, e-pub. Nov. 6, 2008). "Loss of Function Genetic Screens Reveal MTGR1 As an Intracellular Repressor of Beta 1 Integrin-Dependent Neurite Outgrowth," *J. Neurosci. Methods* 177(2):322-333.

Ossovskaya, V. et al. (2011). "Targeting of Induced Cancer Stem Cells With Iniparib in Combination With Carboplatin and Gemcitabine," *Abstract presented at the 102$^{nd}$ Annual Meeting of the American Association for Cancer Research*, on Apr. 2-6, 2011, Orange County, Orlando, Florida, abstract located at http://www.abstractsonline.com/Plan/ViewAbstract.aspx?sKey=89ac2f8b-2fde-4afc-b88c-2ab594d43ad4&cKey=55bd070e-7af7-4053-a71c-5e1fa31cac87&mKey=%7b507D311A-B6EC-436A-BD67-6D14ED39622C%7d, last visited on Jun. 7, 2011, Abstract No. LB-386, Poster Section 39, 2 pages (Abstract).

Ossovskaya, V. et al. (2011). "The Chemosensitizing Properties of Iniparib in Combination With DNA-Damaging Agents in the MDA-MB-468(-) Triple-Negative Breast Cancer (TNBC) Cell Line," *Abstract presented at the 102$^{nd}$ Annual Meeting of the American Association for Cancer Research on* Apr. 2-6, 2011, in Orange County, Orlando, Florida, abstract located at http://www.asco.org/portal/site/ASCOv2/template.RAW/menuitem.a1c60e38cd6d5b9f01ae0094ef37a01d/?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=81367, last visited on Jun. 7, 2011, Abstract No. LB-401, Poster Section 39, 3 pages (Abstract).

Ossovskaya, V. et al. (2011). "The Chemosensitizing Properties of Iniparib in Combination With Gemcitabine (G) and Carboplatin (C) in OVCAR-3 Ovarian Adenocarcinoma," Abstract published in conjunction to the 2011 ASCO Annual Meeting held on Jun. 3-7, 2011, in Chicago, Illinois, but not presented at the Meeting, can be found on line only, Abstract located at http://www.asco.org/portal/site/ASCOv2/template.RAW/menuitem.a1c60e38cd6d5b9f01ae0094ef37a01d/?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=81367, last visited on Aug. 2, 2011, Abstract No. e15532, 3 pages (Abstract).

Penson, R. T. et al. (2011). "A Phase II Trial of Iniparib (BSI-201) in Combination With Gemcitabine/Carboplatin (GC) in Patients With Platinum-Sensitive Recurrent Ovarian Cancer," *Abstract presented at the 2011 ASCO Annual Meeting, held on* Jun. 3-7, 2011, in Chicago, Illinois, abstract located at http://www.asco.org/portal/site/ASCOv2/template.RAW/menuitem.a1c60e38cd6d5b9f01ae0094ef37a01d/?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=82124, last visited on Aug. 2, 2011, Abstract No. 5004, 3 pages (Abstract).

Penson, R. T. et al. (2011). "A Phase 2 Trial of Iniparib (BSI-201) in Combination With Gemcitabine/Carboplatin (GC) in Patients With Platinum-Sensitive Recurrent Ovarian Cancer," Poster presented at the 2011 ASCO Annual Meeting, held on Jun. 3-7, 2011, in Chicago, Illinois, 21 pages (Poster).

Perez, E. A. (Mar. 2009, e-pub. Apr. 29, 2008). "Impact, Mechanisms, and Novel Chemotherapy Strategies for Overcoming Resistance to Anthracyclines and Taxanes in Metastatic Breast Cancer," *Breast Cancer Res. Treat.* 114(2):195-201.

Rasola, A. et al. (Feb. 15, 2007, e-pub. Sep. 4, 2006). "A Positive Feedback Loop Between Hepatocyte Growth Factor Receptor and β-Catenin Sustains Colorectal Cancer Cell Invasive Growth," *Oncogene* 26(7):1078-1087.

Roche—Instruction Manual (Aug. 2003). Cell Proliferation ELISA BrdU (Chemiluminescence), Cat. No. 1 669 915, version 4, 24 pages.

Rosell, R. et al. (Nov. 2007). "BRCA1: A Novel Prognostic Factor in Resected Non-Small-Cell Lung Cancer," *PLoS One*, 2(11):e1129, 7 pages.

Salomon, D. S. (1995). "Epidermal Growth Factor-Related Peptides and Their Receptors in Human Malignancies," *Crit. Rev. Oncol. Hematol.* 19:183-232.

Sandler, A. et al. (Dec. 14, 2006). "Paclitaxel-Carboplatin Alone or With Bevacizumab for Non-Small-Cell Lung Cancer," *New Engl. J. Med.* 355(24):2542-2550.

Sanofi-Aventis, (Jan. 27, 2011). "Sanofi-Aventis Reports Top-Line Results From Phase III Study With Iniparib (BSI-201) in Metastatic Triple-Negative Breast Cancer," Article located at <http://seekingalpha.com/news-article/484782-sanofi-aventis-reports-top-line-results-from-phase-iii-study-with-iniparib-bsi-201-in-meta-static-triple-negative-breast-cancer>, last visited May 25, 2011, published in PR Newswire Article, 2 pages.

Sasaki, K. et al. (Jul. 1986). "Flow Cytometrix Estimation of Cell Cycle Parameters Using a Monoclonal Antibody to Bromoedexyuridine," *Cytometry* 7(4):391-395.

Sasaki, H. et al. (Dec. 2007, e-pub. Aug. 7, 2007). "*EGFR* Exon 20 Insertion Mutation in Japanese Lung Cancer," *Lung Cancer* 58(3)324-328.

Shi, Y. et al. (Jul.-Aug. 2005). "Quantitative Analysis of Membrane Proteins From Breast Cancer Cell Lines BT474 and MCF7 Using Multistep Solid Phase Mass Tagging and 2D LC/MS," *J. Proteome Res.* 4(4):1427-1433.

Shigematsu, H. et al. (Mar. 2, 2005). "Clinical and Biological Features Associated With Epidermal Growth Factor Receptor Gene Mutations in Lung Cancers," *J. Natl. Cancer Inst.* 97(5):339-346.

Sordella, R. et al. (Aug. 20, 2004, e-pub. Jul. 29, 2004). "Gefitinib-Sensitizing *EGFR* Mutations in Lung Cancer Activate Anti-Apoptotic Pathways," *Science* 305(5687):1163-1167.

Spigel, D. R. et al. (2011). "Randomized Phase III Trial of Gemcitabine/Carboplatin With or Without Iniparib (BSI-201) in Patients with Previously Untreated Stage IV Squamous Non-Small Cell Lung Cancer (NSCLC)," *Abstract presented at the 2011 ASCO Annual Meeting held on* Jun. 3-7, 2011, in Chicago, IL, USA, abstract located at http://www.asco.org/portal/site/ASCOv2/template.RAW/menuitem.a1c60e38cd6d5b9f01ae0094ef37a01d/?javax.portlet.tpst=b2e033002b246c2828a46427ef37a01d_ws_RW&javax.portlet.prp_b2e033002b246c2828a46427ef37a01d_viewID=abst_detail_rawview&javax.portlet.begCacheTok=com.vignette.cachetoken&javax.portlet.endCacheTok=com.vignette.cachetoken&index=n&confID=102&abstractID=84545, last visited on Aug. 2, 2011, Abstract No. TPS220, 3 pages (Abstract).

Spigel, D. R. et al. (2011). "Randomized Phase III Trial of Gemcitabine/Carboplatin With or Without Iniparib (BSI-201) in Patients with Previously Untreated Stage IV Squamous Non-Small Cell Lung Cancer (NSCLC)," Poster presented at the 2011 ASCO Annual Meeting, held on Jun. 3-7, 2011, in Chicago, IL, USA, Poster No. TPS220, 11 pages (Poster).

Su, H. et al. (Oct. 1, 2006, e-pub. Oct. 4, 2006). "Monitoring Tumor Glucose Utilization by Positron Emission Tomography Growth Factor Receptor Kinase Inhibitors," *Clin. Cancer Res.* 12(19):5659-5667.

Telli, M. L. et al. (Dec. 8, 2011). "A Phase II Study of Gemcitabine and Carboplatin (GC) Plus Iniparib (BSI-201) as Neoadjuvant Therapy for Triple-Negative and BRCA1/2 Mutation-Associated Breast Cancer," Poster P3-14-08 presented at the 34$^{th}$ Annual San Antonio Breast Cancer Symposium, San Antonio, Texas, USA, Dec. 6-10, 2011, 13 pages.

Tracy, S. et al. (2004, e-pub. Oct. 15, 2004). "Gefitinib Induces Apoptosis in the EGFR$^{L858R}$ Non-Small-Cell Lung Cancer Cell Line H3255," *Cancer Res.* 64:7241-7244.

Vaporciyan, A. A. et al. (2000). "Cancer of the Lung," in *Cancer Medicine*, 5$^{th}$ ed., Bast R. C. et al. (eds), Ontario, B. C. Becker Inc., pp. 1227-1292.

Vippagunta, S. R. et al. (2001). "Crystalline Solids," *Adv. Drug. Delivery Reviews* 48(18):3-26, Section 3.4.

Von Eyben, F. E. (2006). "Epidermal Growth Factor Receptor Inhibition and Non-Small Cell Lung Cancer," *Crit. Rev. Clin. Lab. Sci.* 43(4):291-323.

White, A. W. et al. (2004). "Potentiation of Cytotoxic Drug Activity in Human Tumour Cell Lines, by Amine-Substituted 2-Arylbenzimidazole-4-Carboxamide PARP-1 Inhibitors," *Bioorganic & Medicinal Chemistry Letters* 14:2433-2437.

Wikipedia (2011), "Lung Cancer," article located at en.wikipedia.org/wiki/Lung_cancer, last visited on Oct. 28, 2011, 24 pages total.

Wynder, E. L. (Nov. 1972). "Etiology of Lung Cancer—Reflections of Two Decades of Research," *Cancer* 30(5):1332-1339.

European Search Report mailed on Jul. 28, 2011, for European Patent Application No. 08848605.5, filed on May 27, 2010, 5 pages.

European Search Report and European Search Opinion mailed on May 2, 2011, for European Patent Application No. 08857430.6, filed on Dec. 5, 2008, 5 pages.

European Search Report and European Search Opinion mailed on Apr. 18, 2011, for European Patent Application No. 09708089.9, filed on Feb. 4, 2009, 8 pages.

European Search Report mailed on May 6, 2011, for European Patent Application No. 08849309.3, filed Nov. 11, 2008, 6 pages.

European Office Action mailed on Dec. 2, 2011, for European Patent Application No. 06 787 758.9, filed on Jul. 18, 2006, 5 pages.

Non Final Office Action mailed on Sep. 27, 2011, for U.S. Appl. No. 12/496,593, filed Jul. 1, 2009, 19 pages.

Non Final Office Action mailed on Jun. 28, 2011, for U.S. Appl. No. 12/329,503, filed Dec. 5, 2008, 30 pages.

Non Final Office Action mailed on Jun. 28, 2011, for U.S. Appl. No. 12/322,551, filed Feb. 4, 2009, 17 pages.

Brambilla, E. et al. (Dec. 2001). "The New World Organization Classification of Lung Tumours," *Eur. Resp. J.* 18(6):1059-1068.

U.S. Appl. No. 13/146,865, internationally filed Feb. 4, 2010, for Sherman et al.

U.S. Appl. No. 13/169,785, filed Jun. 27, 2011, for Ossovskaya et al.

U.S. Appl. No. 13/316,970, filed Dec. 12, 2011, for Ossovskaya et al.

U.S. Appl. No. 13/323,630, filed Dec. 12, 2011, for Moore et al.

U.S. Appl. No. 13/323,649, filed Dec. 12, 2011, for Ossovskaya et al.

\* cited by examiner

BT474 - Breast cancer cell line

BP: 6-amino-5-iodo-benzopyrone
BA: 4-iodo-3-nitrobenzamide

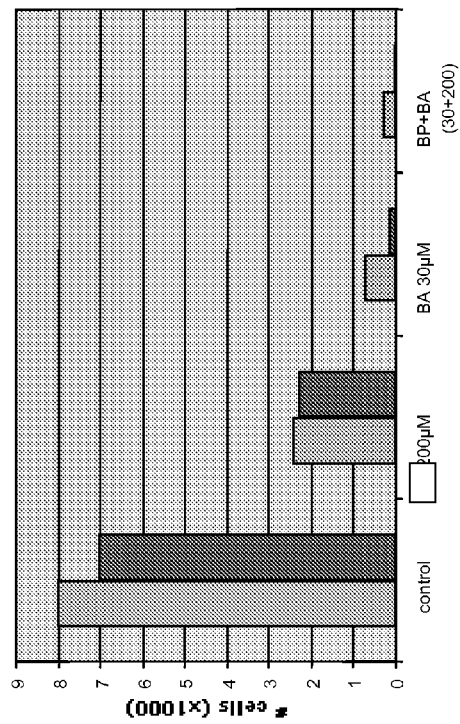
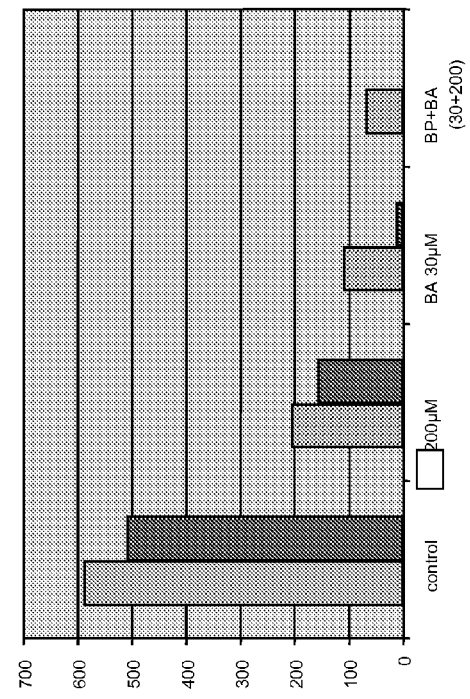
FIG. 2
Ovarian cancer cell lines
BP: 6-amino-5-iodo-benzopyrone
BA: 4-iodo-3-nitrobenzamide
BSO: Buthionine sulfoximine Lung cancer - NIH-292 cell line Lung cancer – NIH-292 cell line BP: 6-amino-5-iodo-benzopyrone
BA: 4-iodo-3-nitrobenzamide
BSO: Buthionine sulfoximine Lung cancer NCA549 cells Prostate cancer: PC-3 Cells Prostate cancer DUPRO Cells Pancreatic cancer PANC1 cells Pancreatic cancer CFPAC1 cells Pancreatic cancer NOR-P1 cells BP (28.5mg/kg), BA (5mg/kg), and BSO (660mg/kg)
In vivo in subcutaneous breast cancer model BP: 6-amino-5-iodo-benzopyrone
BA: 4-iodo-3-nitrobenzamide
BSO: Buthionine sulfoximine 4-Iodo-3-nitrobenzamide demonstrates anti-tumor efficacy in OVCAR3 (human ovarian adenocarcinoma) xenograft model in nude mice BA: 4-iodo-3-nitrobenzamide

Body Weight

Body Weight

BA + BP in Vivo

In vivo: BP reduces tumor volume
(mammary xenograft)

BP: 6-amino-5-iodo-benzopyrone

TREATMENT OF CANCER

CROSS-REFERENCE

This application is a continuation of U.S. patent application Ser. No. 11/458,379 (now U.S. Pat. No. 7,405,227), filed on Jul. 18, 2006 which claims priority to U.S. Provisional Application No. 60/700,446, filed Jul. 18, 2005, which are incorporated herein by reference in their entirety.

BACKGROUND OF THE INVENTION

Cancer is a serious threat to modern society. Malignant cancerous growths, due to their unique characteristics, pose serious challenges for modern medicine. Their characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

There are many types of cancer, including, breast, lung, ovarian, bladder, prostate, pancreatic, cervical, and leukemia. Currently, some of the main treatments available are surgery, radiation therapy, and chemotherapy. Surgery is often a drastic measure and can have serious consequences. For example, all treatments for ovarian cancer may result in infertility. Some treatments for cervical cancer and bladder cancer may cause infertility and/or sexual dysfunction. Surgical procedures to treat pancreatic cancer may result in partial or total removal of the pancreas and can carry significant risks to the patient. Breast cancer surgery invariably involves removal of part of or the entire breast. Some surgical procedures for prostate cancer carry the risk of urinary incontinence and impotence. The procedures for lung cancer patients often have significant post-operative pain as the ribs must be cut through to access and remove the cancerous lung tissue. In addition, patients who have both lung cancer and another lung disease, such as emphysema or chronic bronchitis, typically experience an increase in their shortness of breath following the surgery.

Radiation therapy has the advantage of killing cancer cells but it also damages non-cancerous tissue at the same time. Chemotherapy involves the administration of various anti-cancer drugs to a patient but often is accompanied by adverse side effects.

Worldwide, more than 10 million people are diagnosed with cancer every year and it is estimated that this number will grow to 15 million new cases every year by 2020. Cancer causes six million deaths every year or 12% of the deaths worldwide. There remains a need for methods that can treat cancer. These methods can provide the basis for pharmaceutical compositions useful in the prevention and treatment of cancer in humans and other mammals.

A series of anti-tumor drugs have been identified. These drugs include nitro and nitroso compounds and their metabolites, which are the subject of U.S. Pat. No. 5,464,871 issued on Nov. 7, 1995 entitled "Aromatic Nitro and Nitroso Compounds and their Metabolites Useful as Anti-viral and Anti-tumor Agents," U.S. Pat. No. 5,670,518 issued on Sep. 23, 1997 entitled "Aromatic Nitro and Nitroso Compounds and their Metabolites Useful as Anti-viral and Anti-tumor Agents," U.S. Pat. No. 6,004,978 issued on Dec. 21, 1999 entitled "Methods of Treating Cancer with Aromatic Nitro and Nitroso Compounds and their Metabolites" the disclosures of which are incorporated herein by reference.

SUMMARY OF THE INVENTION

The present invention relates generally to methods of treatment of tumorigenic diseases using aromatic nitrobenzamide compounds and their metabolites. More specifically, it relates to the use of the nitro compound 4-iodo-3-nitrobenzamide or a salt, solvate, isomer, tautomer, metabolite, analog, or prodrug thereof in suppressing and inhibiting tumor growth in a mammal.

In one aspect of the invention, a method for treatment of cancer and disorders associated with cancer is provided comprising administering of pharmaceutical compositions comprising a compound of formula (Ia) with one or more additional pharmacologically active agents. In another aspect, a method for treatment of cancer and disorders associated with cancer is provided comprising administering a combination of a compound of formula (Ia) and buthionine sulfoximine (BSO). The compound of formula (Ia) can also be administered in combination with a benzopyrone compound of formula (II), with or without BSO.

In some preferred embodiments, the cancers are ovarian cancer, endometrium cancer, cervical cancer, pancreatic cancer, bladder cancer, eye cancer, central nervous system cancer, kidney cancer, thyroid cancer, and a lung cancer. In some preferred embodiments, the cancers are mammary gland ductal carcinoma, breast infiltrating carcinoma of lobular type, breast intraductal carcinoma, breast mucinous carcinoma, promyleocytic leukemia in the peripheral blood, an ovarian adenocarcinoma, an ovarian adenocarcinoma that has migrated into the abdominal cavity, a prostate adenocarcinoma, a transitional cell carcinoma of the bladder, an epitheliod carcinoma in a pancreatic duct, an adenocarcinoma in a pancreatic duct, an adenocarcinoma in the cervical epithelium, and a lung cancer. In some preferred embodiments, the cancers are breast infiltrating carcinoma of lobular type, breast intraductal carcinoma and breast mucinous carcinoma. In some preferred embodiments, the cancers are colon cancer, prostate cancer, liver cancer, leukemia, glioma, and melanoma.

In some preferred embodiments of the abovementioned aspect of the present invention, the treatment further comprises surgery, radiation therapy, chemotherapy, gene therapy, immunotherapy, or a combination thereof. In some preferred embodiments, the administration of the compound is intravenous. In some preferred embodiments, a poly-ADP-ribose polymerase (PARP) molecule is inhibited by the compound of the present invention. In some preferred embodiments, a tumor cell undergoes apoptosis, cell cycle arrest, and/or necrosis in the subject after the administration of the compound of the present invention.

This invention relates to compositions of matter and pharmaceutical compositions, and to methods for their use in the treatment of cancer. For example, a composition of the invention can be a combination of two or more compounds described herein and/or a combination of two or more forms of a compound described herein. A pharmaceutical composition of the invention may be a composition suitable for administration to a subject.

BRIEF DESCRIPTION OF THE FIGURES

FIG. 2 depicts the effect of nitrobenzamide and benzopyrone compounds on the Ovcar3 and Skov3 ovarian cancer cell lines, with and without the co-treatment of BSO.

DETAILED DESCRIPTION OF THE INVENTION

Definitions

Figure 1:
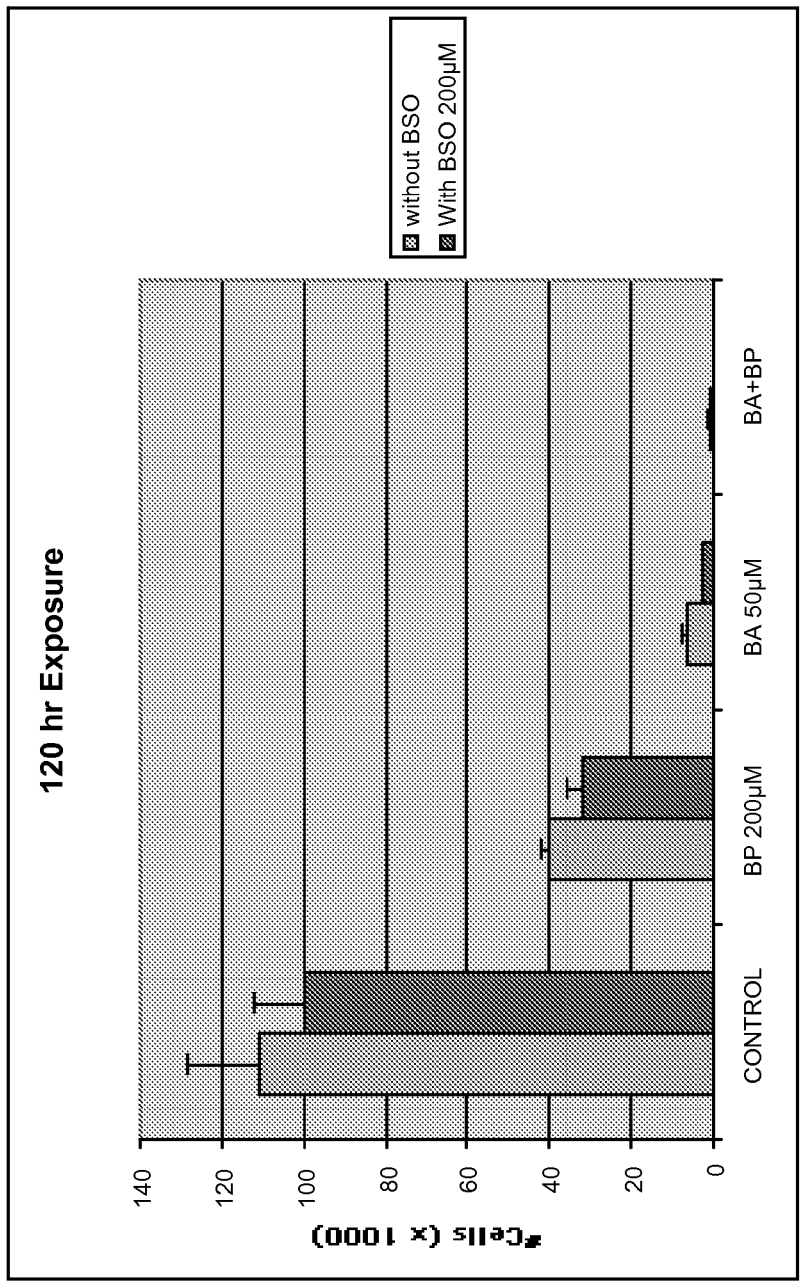
FIG. 1 depicts the effect of a nitrobenzamide compound on the BT474 breast cancer cell line, with and without the co-treatment of buthionine sulfoximine (BSO).
Figure 3A:
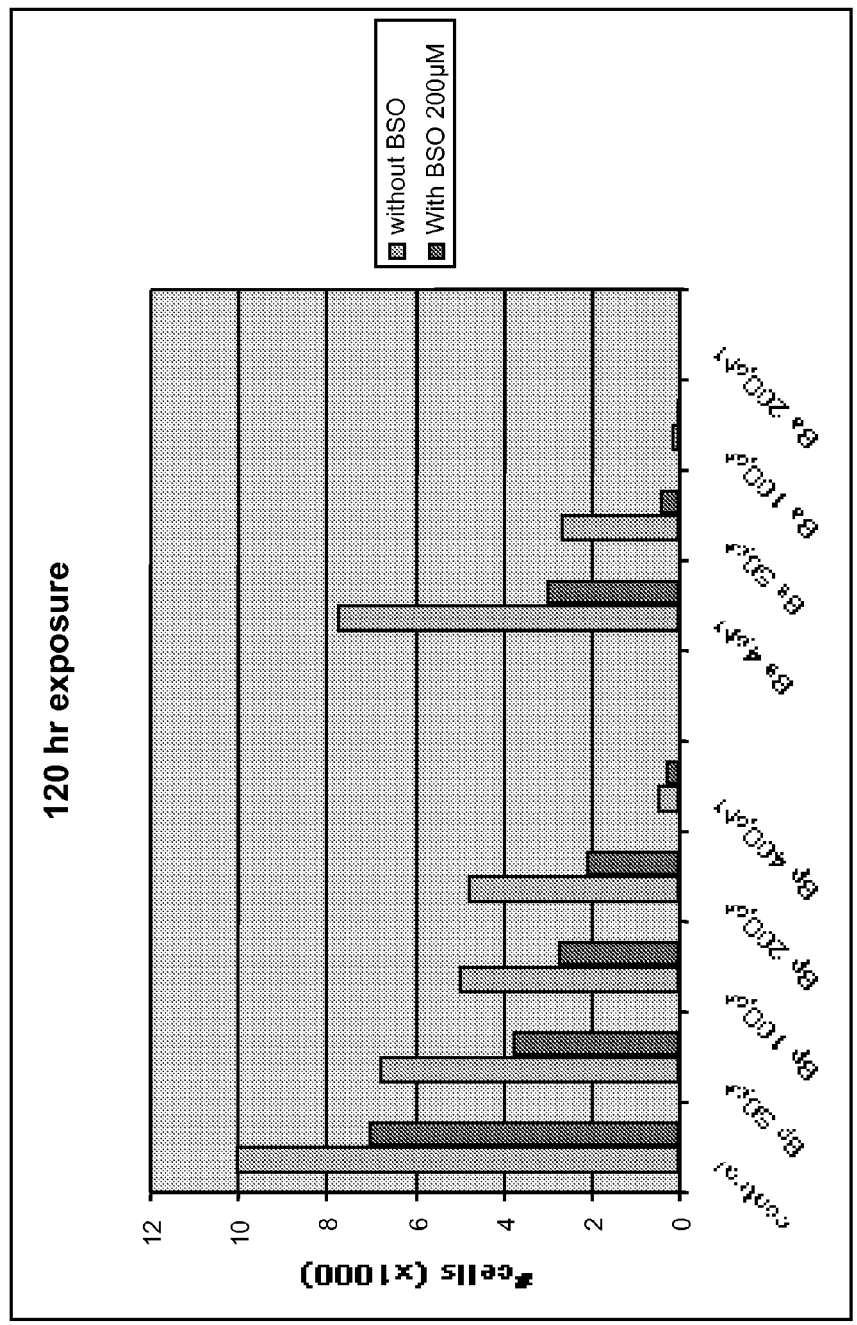
FIGS. 3A and 3B depicts the effect of nitrobenzamide and benzopyrone compounds on a lung cancer cell line, with and without the co-treatment of BSO.
Figure 3B:
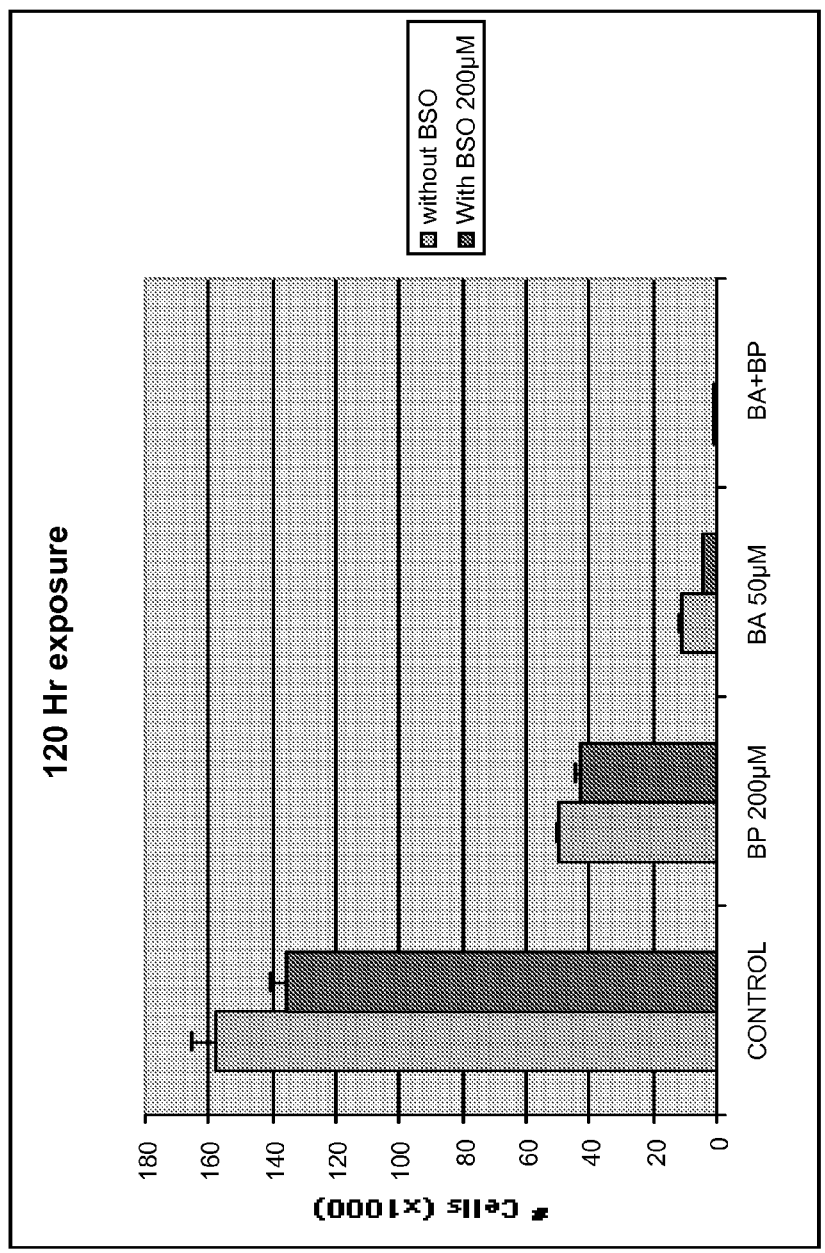
Figure 4:
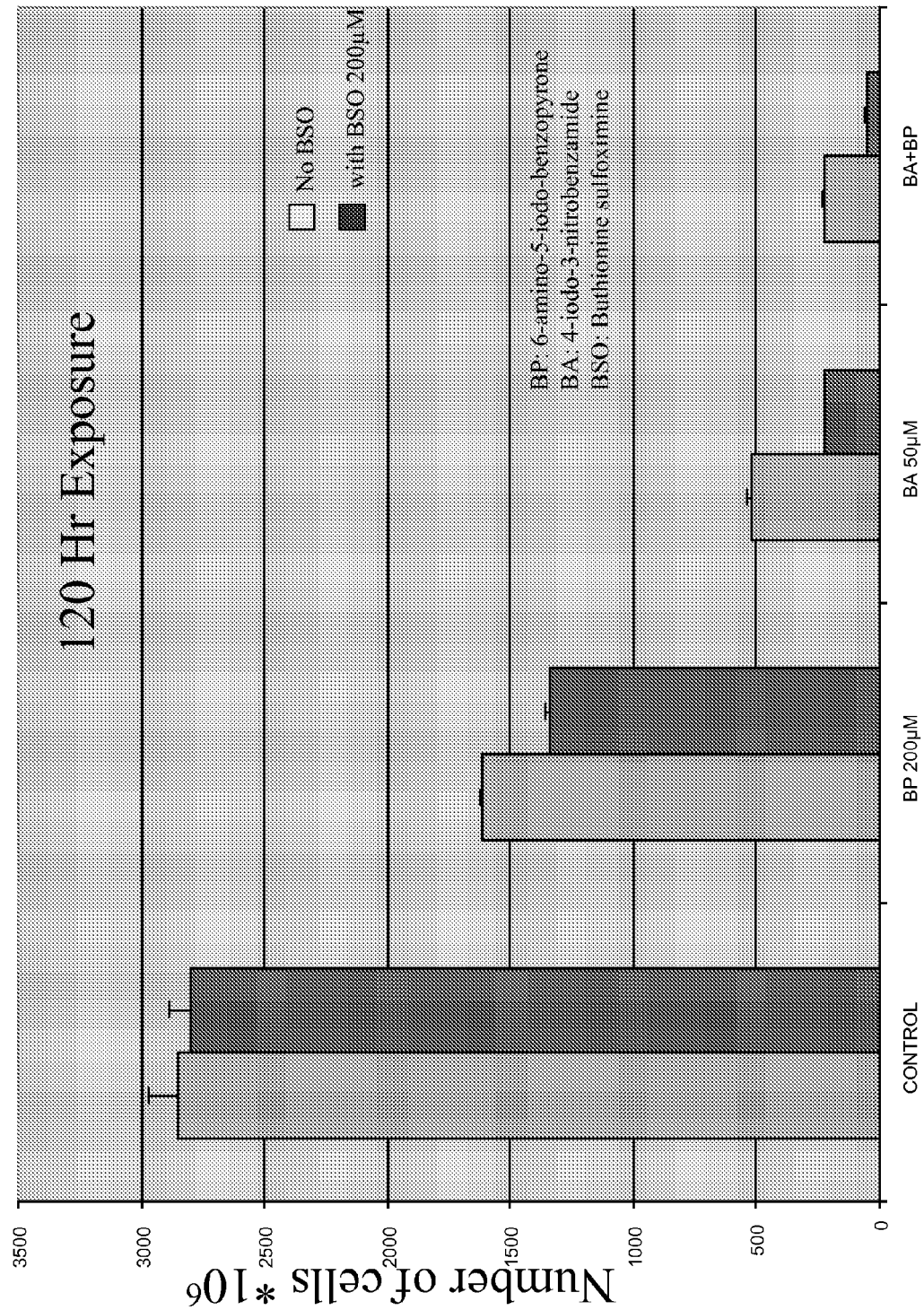
FIG. 4 depicts the effect of nitrobenzamide and benzopyrone compounds on a lung cancer cell line, with and without the co-treatment of BSO.
Figure 5:
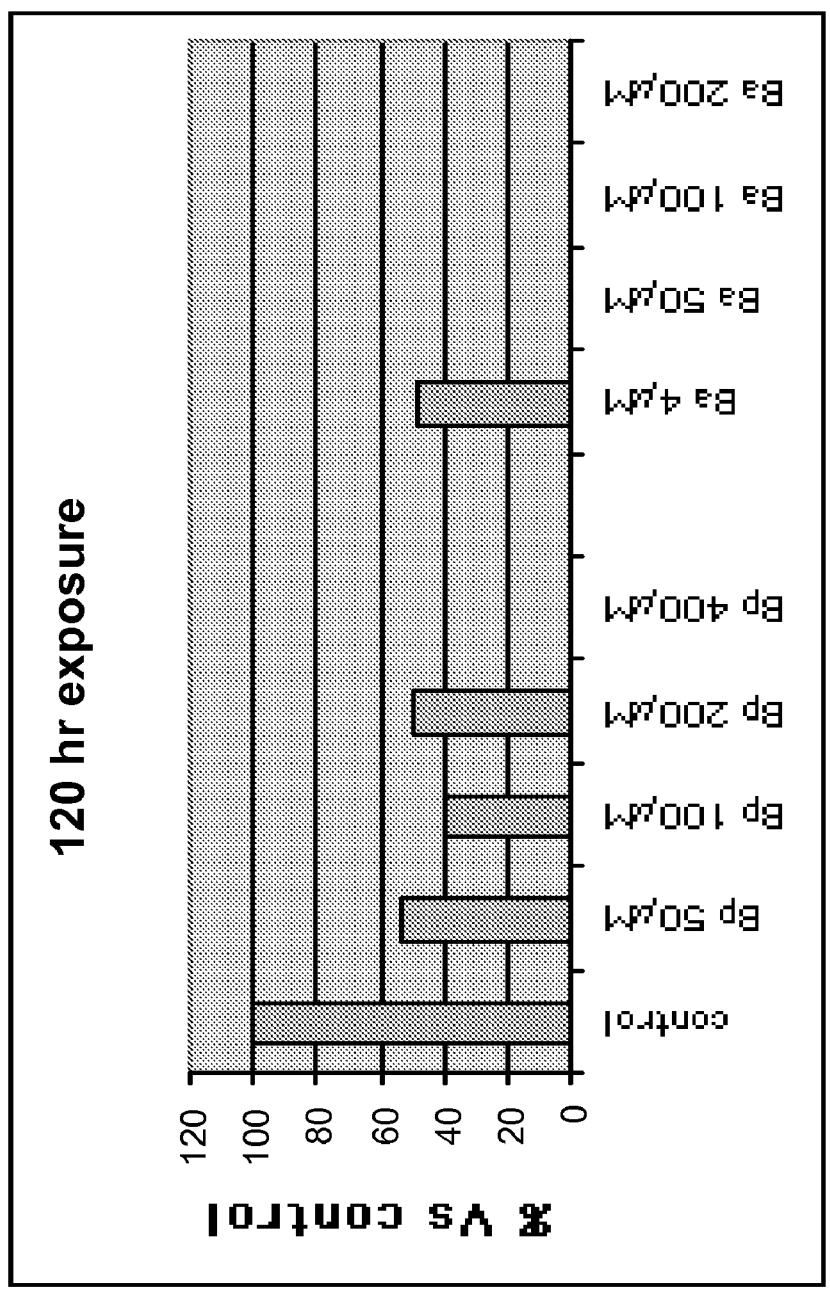
FIG. 5 depicts the effect of a nitrobenzamide compound on the TUCCSUP bladder cancer cell line.
Figure 6:
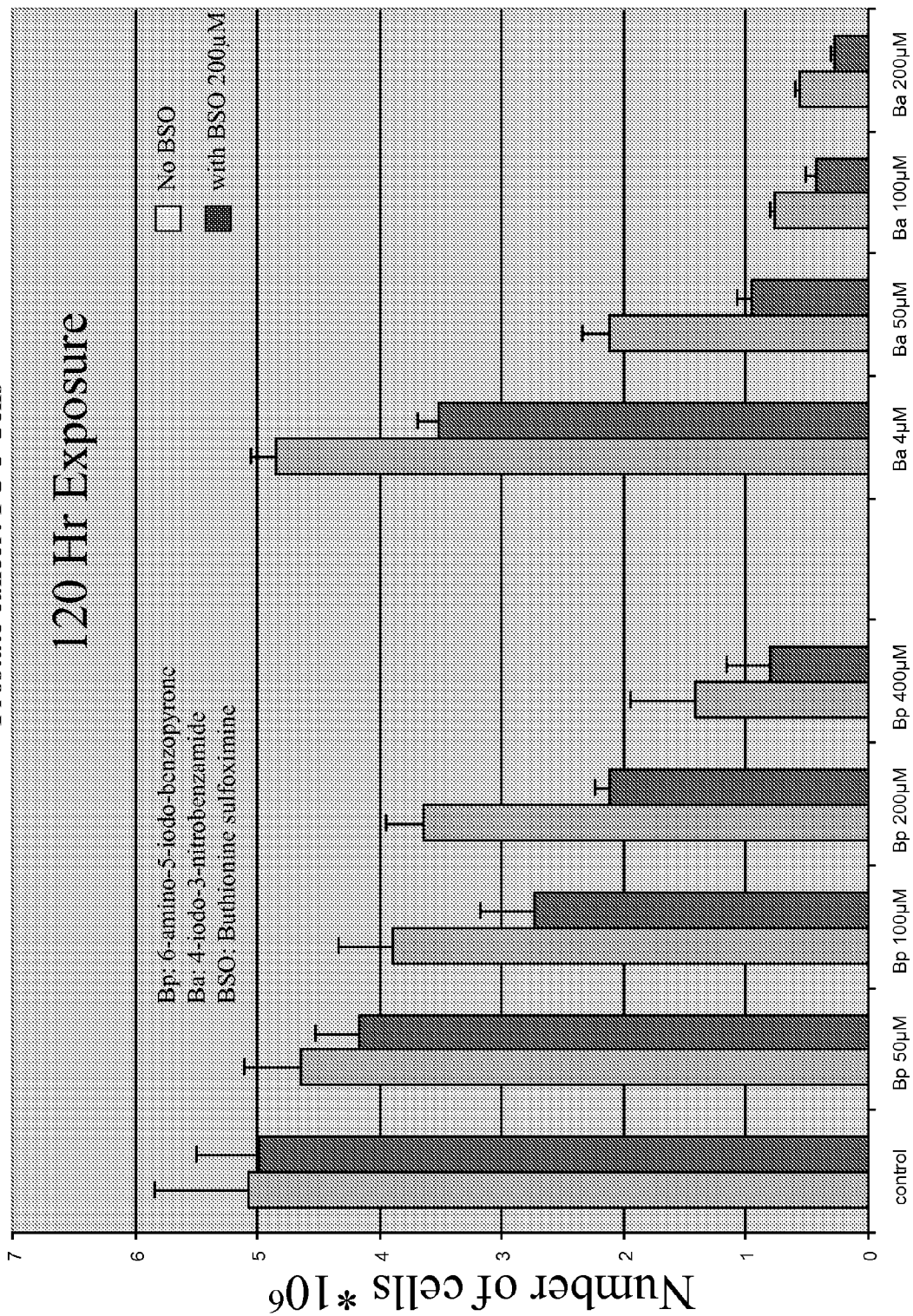
FIG. 6 depicts the effect of nitrobenzamide and benzopyrone compounds on a prostate cancer cell line, with and without the co-treatment of BSO.
Figure 7:
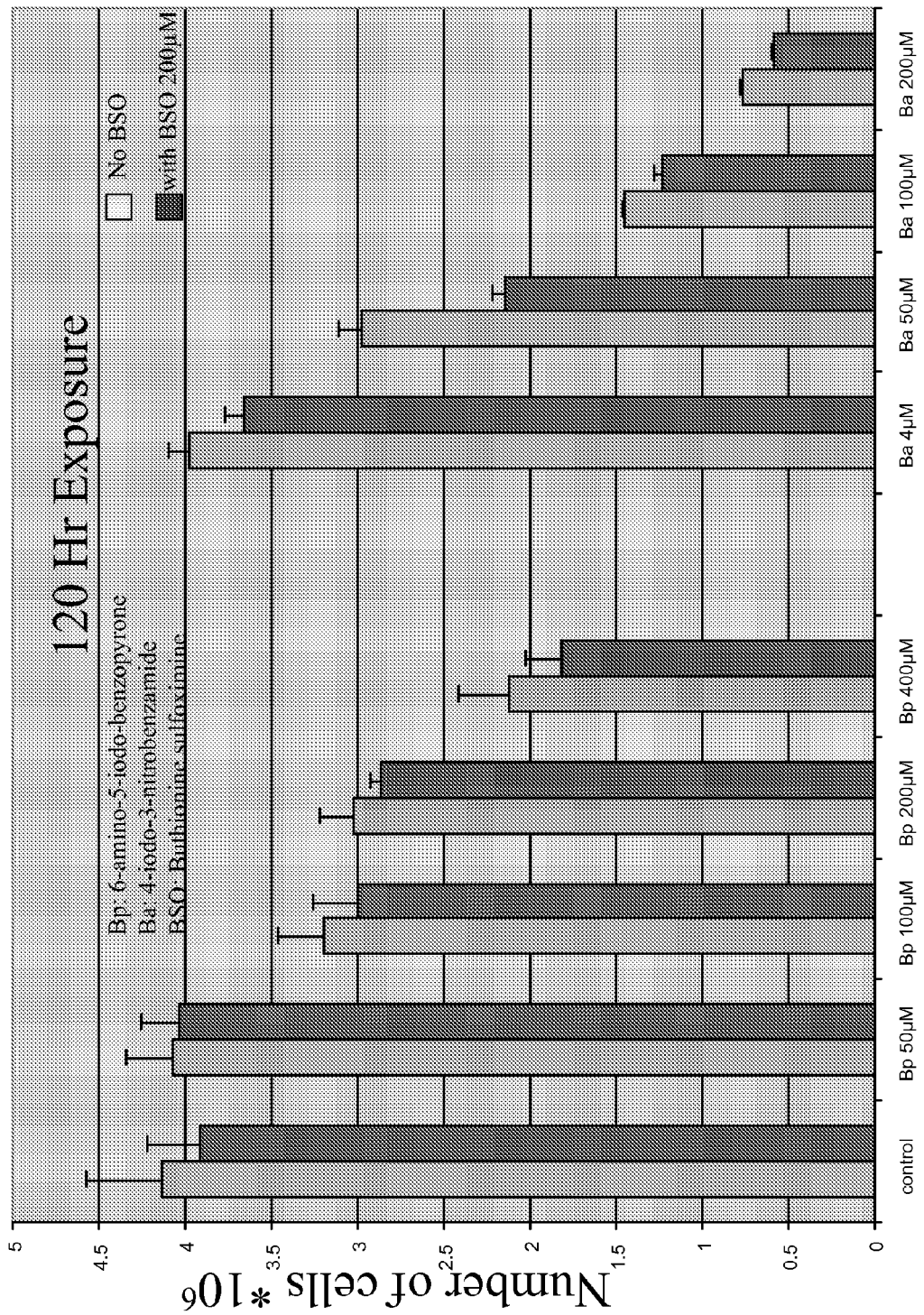
FIG. 7 depicts the effect of nitrobenzamide and benzopyrone compounds on a prostate cancer cell line, with and without the co-treatment of BSO.
Figure 8:
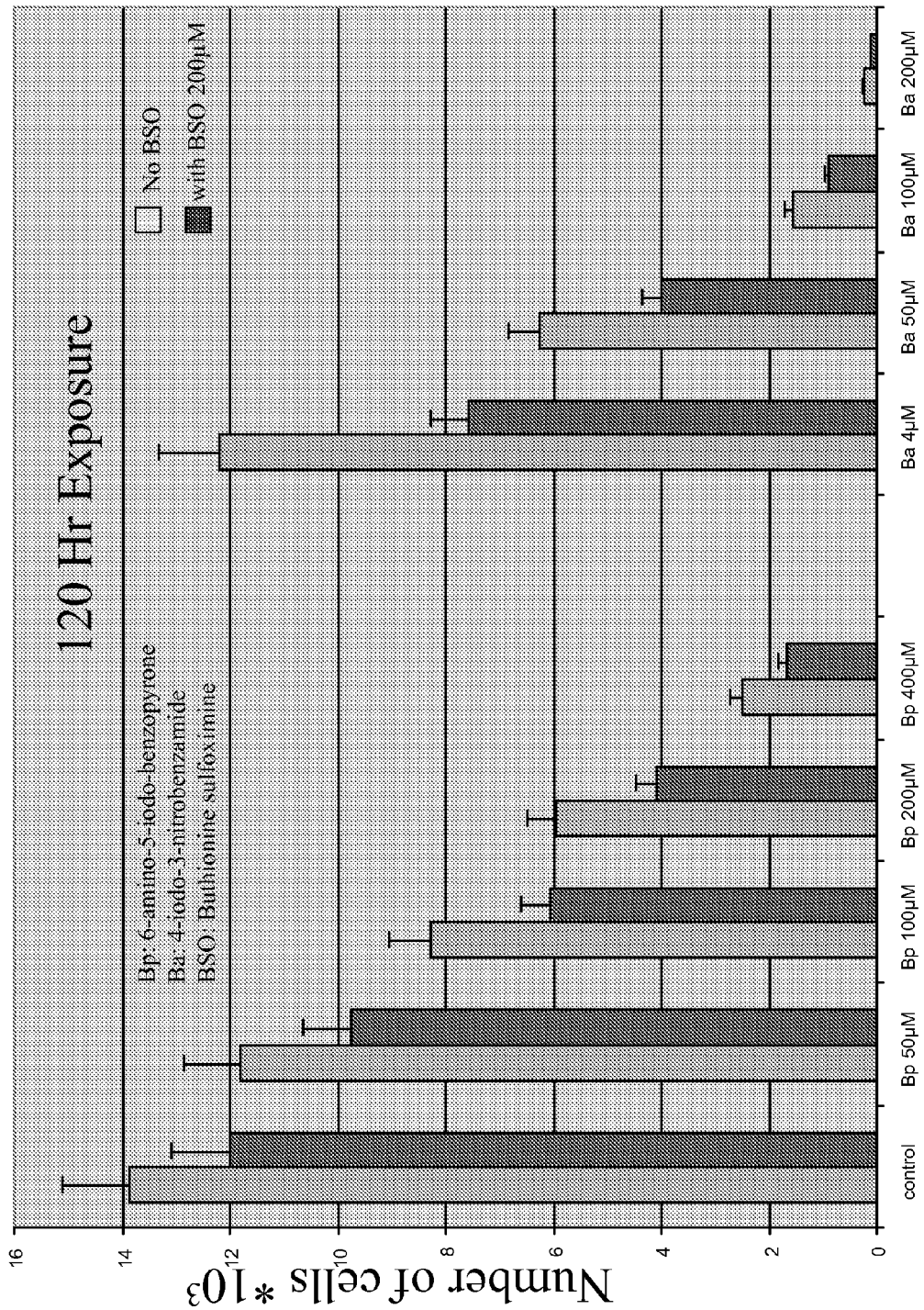
FIG. 8 depicts the effect of nitrobenzamide and benzopyrone compounds on a pancreatic cancer cell line, with and without the co-treatment of BSO.
Figure 9:
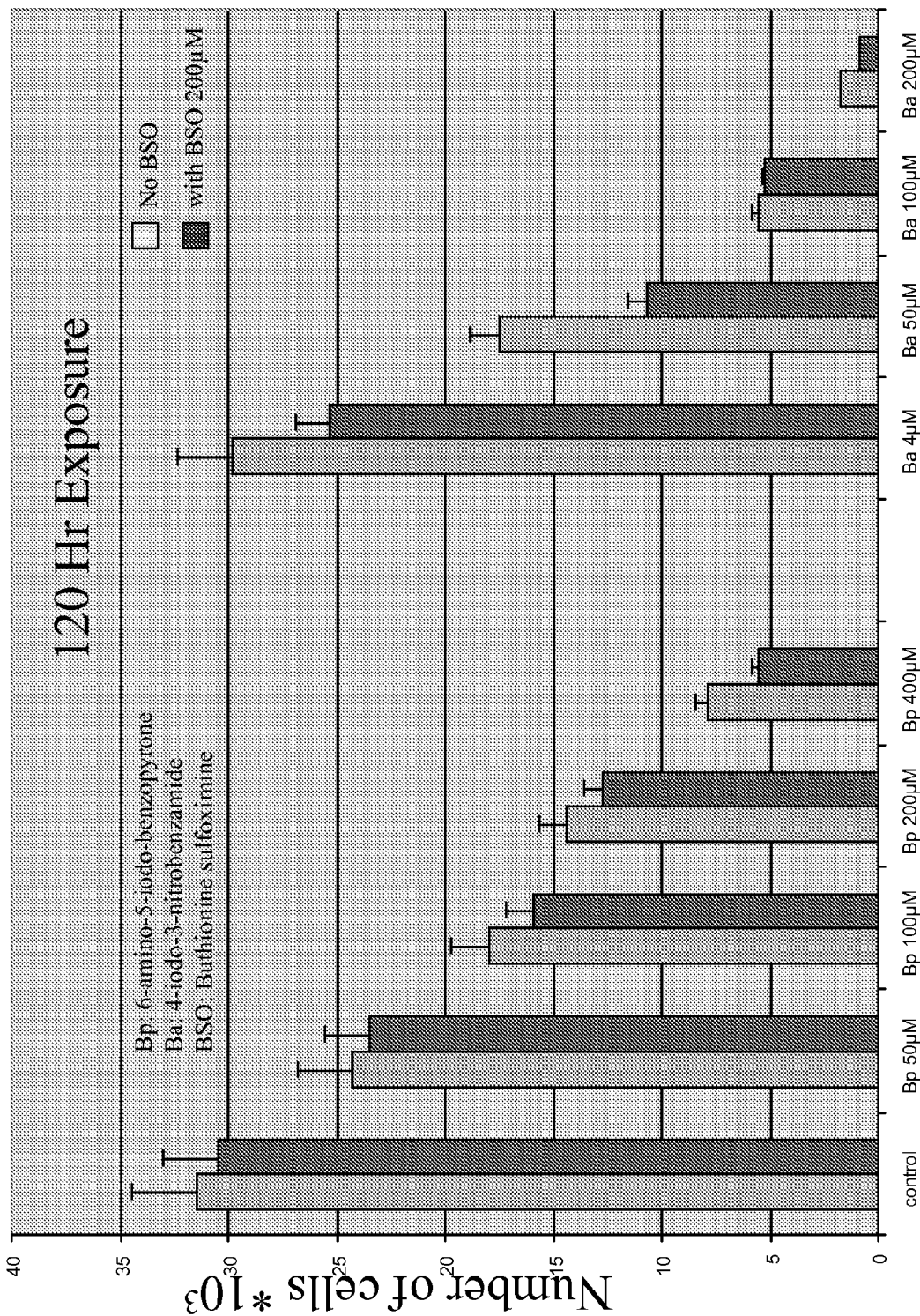
FIG. 9 depicts the effect of nitrobenzamide and benzopyrone compounds on a pancreatic cancer cell line, with and without the co-treatment of BSO.
Figure 10:
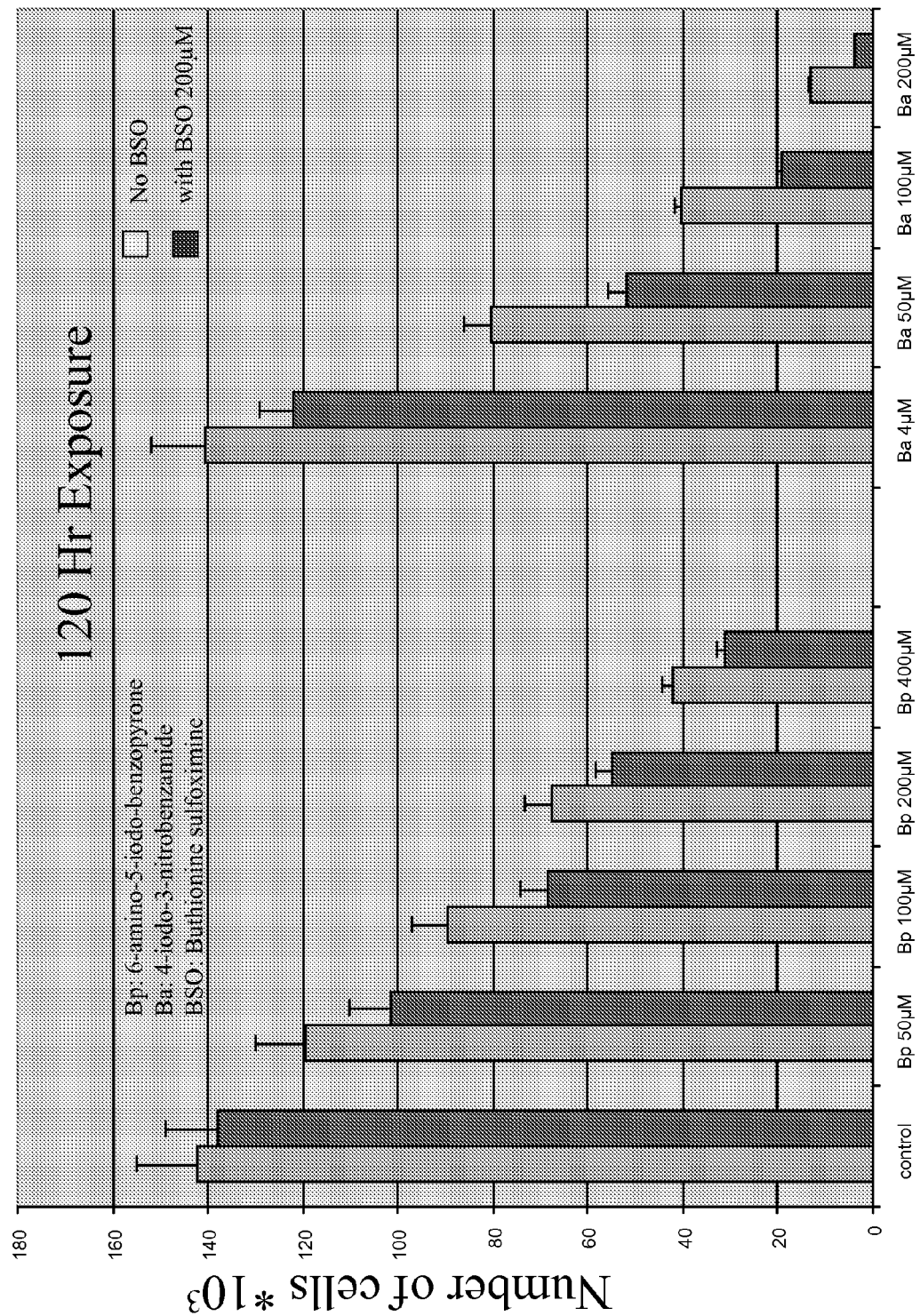
FIG. 10 depicts the effect of nitrobenzamide and benzopyrone compounds on a pancreatic cancer cell line, with and without the co-treatment of BSO.

"Nitrobenzamide compound(s)" means a compound of the formula (Ia)

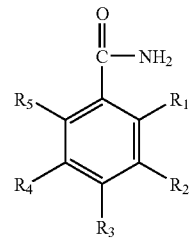

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

"Chemotherapy" means the administration of one or more anti-cancer drugs such as, antineoplastic chemotherapeutic agents, chemopreventative agents, and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to shrink a large tumor prior to a surgical procedure to remove it, after surgery or radiation therapy to prevent the growth of any remaining cancer cells in the body.

The terms "effective amount" or "pharmaceutically effective amount" refer to a nontoxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of a nitrobenzamide compound as disclosed herein per se or a composition comprising the nitrobenzamide compound herein required to provide a clinically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method of the invention may be performed on, or a composition of the invention administered to a patient at risk of developing cancer, or to a patient reporting one or more of the physiological symptoms of such conditions, even though a diagnosis of the condition may not have been made.

Nitrobenzamide Compounds

Compounds useful in the present invention are of Formula (Ia)

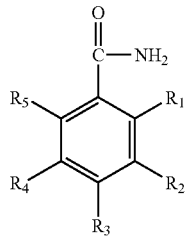

(Ia)

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo.

A preferred compound of formula Ia is

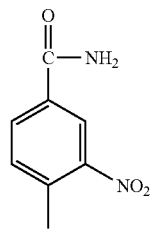

(BA)

4-iodo-3-nitrobenzamide

The present invention provides for the use of the aforesaid nitrobenzamide compounds for the treatment of breast cancers including a ductal carcinoma in a mammary gland, other forms of leukemia including acute promyleocytic leukemia in peripheral blood, ovarian cancer, lung cancer, bladder cancer, prostate cancer, pancreatic cancer, and cervical cancer, as well as other cancer types described herein (U.S. Pat. No. 5,464,871, U.S. Pat. No. 5,670,518, and U.S. Pat. No. 6,004,978 are incorporated herein by reference in their entirety). The present invention also provides the use of the aforesaid nitrobenzamide compounds for the treatment of Gleevac (Imanitib Mesylate) resistant patient population. Gleevec is a tyrosine kinase inhibitor.

In some preferred embodiments, the nitrobenzamide compounds of the present invention are used for the treatment of breast cancer, particularly, mammary gland ductal carcinoma, breast infiltrating carcinoma of lobular type, breast intraductal carcinoma and breast mucinous carcinoma. In some preferred embodiments, the nitrobenzamide compounds of the present invention are used for the treatment of ovarian and endometrial cancer. In still further preferred embodiments, the nitrobenzamide compounds of the present invention are used for the treatment of lung and colon cancer.

In some preferred embodiments, the nitrobenzamide compounds of the present invention are used for the treatment of bladder and prostate cancer. In some preferred embodiments, the nitrobenzamide compounds of the present invention are used for the treatment of liver and pancreatic cancer. In some preferred embodiments, the nitrobenzamide compounds of the present invention are used for the treatment of leukemia, cervical, glioma, and melanoma.

In still further preferred embodiments, the nitrobenzamide compounds of the present invention are used for the treatment of cancers derived from stem cells. In breast cancer and other malignancies, a proportion of tumour cells—'cancer stem cells'—have the capacity for extensive proliferation and transferral of the tumour. An alteration in stem cell fate and growth may play a role in tumorigenesis. Epithelial stem cells have a life-span at least as long as that of the organism, and thus they are thought to be susceptible to multiple genetic hits which cumulatively may result in tumor formation. Many cancers, such as those of the skin and colon, arise in tissues that are constantly replenished with cells throughout life. But the crucial mutations that lead to the disease are likely to have occurred during the tissues' formative period, when cells are dividing exponentially.

The stem cell compartment, now identified virtually in every tissue, can be defined as a subset of rare cells, endowed with the exclusive prerogative of self-renewal and persistence throughout the organism's life, in contrast with differentiated cells, which form the tissue bulk, but usually feature a postmitotic behavior and a short lifespan. The fact that several mutations are necessary for a cell to become cancerous may suggest that in many tissues the mutations may accumulate in stem cells. As cancer stem cells self-renew, it follows that they may be derived either from self-renewing normal stem cells, or from more differentiated cells that acquire peculiar properties of stem cells. Consistently, a tumor can be conceived as a tissue, including both "differentiated" cells, and a subset of "cancer stem cells", which maintain the tumor mass, and are likely responsible for formation of secondary tumors (metastasis). Hence, nitrobenzamides of the present invention can be used to target cancers derived from stem cells.

The present invention discloses a nonclinical pharmacology of 4-iodo-3-nitrobenzamide (BA) in human tumor and normal primary cells and also in mice, rats, and dogs. In vitro BA inhibited the proliferation of a variety of human tumor cells including breast, colon, prostate, cervix, lung, ovarian, melanoma, lymphoma, and leukemia. In vivo BA was evaluated in several animal models of carcinogenesis. Once-daily or twice-weekly administration of BA inhibits tumor growth in the human ovarian adenocarcinoma xenograft model in both nude and SCID mice, and positively affects the survival rate of animals exposed to the drug given daily or twice weekly.

The twice weekly dosing of BA for 3 weeks followed by a one week washout period is based on the results of the preclinical evaluation of the efficacy and safety of BA.

It has been reported that nitrobenzamide compounds have selective cytotoxicity upon malignant cancer cells but not upon nonmalignant cancer cells. See Rice et al., *Proc. Natl. Acad. Sci. USA* 89:7703-7707 (1992). In one embodiment, the nitrobenzamide compounds utilized in the methods of the present invention may exhibit more selective toxicity towards tumor cells than non-tumor cells.

It has been reported that the anti-tumorigenicity of nitrobenzamide and nitrososbenzamide compounds is enhanced when BSO is co-administered to cancer cells. See Mendeleyev et al., *Biochemical Pharmacol.* 50(5):705-714 (1995). Buthionine sulfoximine (BSO) inhibits gamma-glutamylcysteine synthetase, a key enzyme in the biosynthesis of glutathione, which is responsible in part for cellular resistance to chemotherapy. See Chen et al., *Chem Biol Interact.* Apr 24; 111-112:263-75 (1998). The invention also provides a method for treating cancer comprising the administration of a nitrobenzamide and/or benzopyrone compound in combination with BSO.

In addition to BSO, other inhibitors of gamma-glutamyl-cysteine synthetase can be used in combination with nitrobenzamide and/or benzopyrone compounds. Other suitable analogs of BSO include, but are not limited to, proprothionine sulfoximine, methionine sulfoximine, ethionine sulfoximine, methyl buthionine sulfoximine, γ-glutamyl-α-aminobutyrate and γ-glutamylcysteine.

Benzopyrone Compounds

In some embodiments, the benzamide compounds are administered in combination with benzopyrone compounds of formula II. The benzopyrone compounds of formula II are,

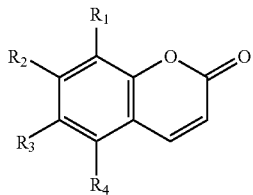

Formula II wherein $R_1$, $R_2$, $R_3$ and $R_4$ are independently selected from the group consisting of H, halogen, optionally substituted hydroxy, optionally substituted amine, optionally substituted lower alkyl, optionally substituted phenyl, optionally substituted $C_4$-$C_{10}$ heteroaryl and optionally substituted $C_3$-$C_8$ cycloalkyl or a salt, solvate, isomer, tautomers, metabolite, or prodrug thereof (U.S. Pat. No. 5,484,951 is incorporated herein by reference in its entirety).

In a preferred embodiment, the invention relates to the following benzopyrone compound of formula II

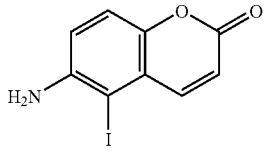

(BP)

6-amino-5-iodo-benzopyrone

Mechanism of Nitrobenzamide Compounds

Not intending to be limited by one mechanism of action, the compounds described herein are believed to have anti-cancer properties via the modulation of a poly (ADP-ribose) polymerase enzyme. The drugs' mechanism of action is related to their ability to act as a ligand for the nuclear enzyme poly (ADP-ribose) polymerase (PARP-1). See Mendeleyev et al., *supra*, (1995). PARP-1 is expressed in the nucleus and catalyzes the conversion of β-nicotinamide adenine dinucleotide ($NAD^+$) into nicotinamide and poly-ADP-ribose (PAR). PARP-1's role in homeostatic conditions seems to be limited to DNA transcription and repair. However, when cellular stress causes DNA damage, PARP-1 activity increases dramatically, which appears to be necessary for genomic integrity. Shall et at., *Mutat Res.* June 30; 460(1):1-15 (2000).

One of PARP-1's functions is to synthesize the biopolymer, poly (ADP-ribose). Both poly (ADP-ribose) and PARP-1 have been linked to the repair of DNA repair, apoptosis, the maintenance of genomic stability, and carcinogenesis. See Masutani et al., *Genes, Chromosomes, and Cancer* 38:339-348 (2003). PARP-1 plays a role in DNA repair, specifically base excision repair (BER). BER is a protection mechanism in mammalian cells for single-base DNA breakage. PARP-1 binds to the ends of DNA fragments through its zinc finger domains with great affinity and thereby acts as a DNA damage sensor. Gradwohl et al., *Proc. Natl. Acad. Sci. USA* 87:2990-2994 (1990); Murcia et al., *Trends Biochem Sci* 19: 172-176 (1994). A breakage in the DNA triggers a binding response by PARP-1 to the site of the break. PARP-1 then increases its catalytic activity several hundred fold (See Simonin et al., *J Biol Chem* 278: 13454-13461 (1993)) and begins to convert poly ADP-ribosylation of itself (Desmarais et al., *Biochim Biophys Acta* 1078: 179-186 (1991)) and BER proteins, such as DNA-PKcs and the molecular scaffold protein XRCC-1. See Ruscetti et al., *J. Biol. Chem.* June 5; 273(23):14461-14467 (1998) and Masson et al., *Mol Cell Biol.* June; 18(6):3563-71 (1998). BER proteins are rapidly recruited to the site of DNA damage. El-Kaminsy et al., *Nucleic Acid Res.* 31(19):5526-5533 (2003); Okano et al., *Mol Cell Biol.* 23(11):3974-3981 (2003). PARP-1's dissociates from the DNA breakage site but it remains in the vicinity of the DNA repair event.

Inhibiting the activity of a PARP molecule includes reducing the activity of these molecules. The term "inhibits" and its grammatical conjugations, such as "inhibitory," is not intended to require complete reduction in PARP activity. Such reduction is preferably by at least about 50%, at least about 75%, at least about 90%, and more preferably by at least about 95% of the activity of the molecule in the absence of the inhibitory effect, e.g., in the absence of an inhibitor, such as a nitrobenzamide compound of the invention. Most preferably, the term refers to an observable or measurable reduction in activity. In treatment scenarios, preferably the inhibition is sufficient to produce a therapeutic and/or prophylactic benefit in the condition being treated. The phrase "does not inhibit" and its grammatical conjugations does not require a complete lack of effect on the activity. For example, it refers to situations where there is less than about 20%, less than about 10%, and preferably less than about 5% of reduction in PARP activity in the presence of an inhibitor such as a nitrobenzamide compound of the invention.

Uses of the Benzamide Compounds

Cancer Types

The invention provides methods to treat several specific cancers or tumors. For example, cancer types include adrenal cortical cancer, anal cancer, aplastic anemia, bile duct cancer, bladder cancer, bone cancer, bone metastasis, Adult CNS brain tumors, Children CNS brain tumors, breast cancer, Castleman Disease, cervical cancer, Childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, Hodgkin's disease, Kaposi' sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sacrcoma, vaginal cancer, vulvar cancer, and Waldenstrom's macroglobulinemia.

Carcinoma of the thyroid gland is the most common malignancy of the endocrine system. Carcinoma of the thyroid gland include differentiated tumors (papillary or follicular) and poorly differentiated tumors (medullary or anaplastic). Carcinomas of the vagina include squamous cell carcinoma, adenocarcinoma, melanoma and sarcoma. Testicular cancer is broadly divided into seminoma and nonseminoma types.

Thymomas are epithelial tumors of the thymus, which may or may not be extensively infiltrated by normeoplastic lymphocytes. The term thymoma is customarily used to describe neoplasms that show no overt atypia of the epithelial component. A thymic epithelial tumor that exhibits clear-cut cytologic atypia and histologic features no longer specific to the thymus is known as a thymic carcinoma (also known as type C thymoma).

The methods provided by the invention may comprise the administration of the benzamide compounds in combination with other therapies. The choice of therapy that can be co-administered with the compositions of the invention will depend, in part, on the condition being treated. For example, for treating acute myeloid leukemia, a benzamide compound of some embodiments of the invention can be used in combination with radiation therapy, monoclonal antibody therapy, chemotherapy, bone marrow transplantation, gene therapy, immunotherapy, or a combination thereof.

Breast Cancer

In one aspect, the invention provides a method of treating breast cancer, preferably a ductal carcinoma in duct tissue in a mammary gland.

Several types of breast cancer exist that may be treated by the methods provided by the invention. A lobular carcinoma in situ and a ductal carcinoma in situ are breast cancers that have developed in the lobules and ducts, respectively, but have not spread to the fatty tissue surrounding the breast or to other areas of the body. An infiltrating (or invasive) lobular and a ductal carcinoma are cancers that have developed in the lobules and ducts, respectively, and have spread to either the breast's fatty tissue and/or other parts of the body. Other cancers of the breast that would benefit from treatment by the methods provided by the invention are medullary carcinomas, colloid carcinomas, tubular carcinomas, and inflammatory breast cancer.

Treatments available for breast cancer patients are surgery, immunotherapy, radiation therapy, chemotherapy, endocrine therapy, or a combination thereof. A lumpectomy and a mastectomy are two possible surgical procedures available for breast cancer patients.

Chemotherapy utilizes anti-tumor agents to prevent cancer cells from multiplying, invading, metastasizing and killing a patient. Several drugs are available to treat breast cancer, including cytotoxic drugs such as doxorubicin, cyclophosphamide, methotrexate, paclitaxel, thiotepa, mitoxantrone, vincristine, or combinations thereof. Endocrine therapy may be an effective treatment where the remaining breast tissue retains endocrine sensitivity. Agents administered for this therapy include tamoxifen, megestrol acetate, aminoglutethimide, fluoxymesterone, leuprolide, goserelin, and prednisone.

The methods provided by the invention can provide a beneficial effect for breast cancer patients, by administration of a nitrobenzamide compound or a combination of administration of a nitrobenzamide compound and surgery, radiation therapy, chemotherapy, or endocrine therapy.

Ovarian Cancer

In another aspect, the invention provides a method of treating ovarian cancer, including epithelial ovarian tumors. Preferably, the invention provides a method of treating an ovarian cancer selected from the following: an adenocarcinoma in the ovary and an adenocarcinoma that has migrated from the ovary into the abdominal cavity. Surgery, immunotherapy, chemotherapy, hormone therapy, radiation therapy, or a combination thereof are some possible treatments available for ovarian cancer. Some possible surgical procedures include debulking, and a unilateral or bilateral oophorectomy and/or a unilateral or bilateral salpigectomy.

Anti-cancer drugs that may be used include cyclophosphamide, etoposide, altretamine, and ifosfamide. Hormone therapy with the drug tamoxifen may be used to shrink ovarian tumors. Radiation therapy may be external beam radiation therapy and/or brachytherapy.

The methods provided by the invention can provide a beneficial effect for ovarian cancer patients, by administration of a nitrobenzamide compound or a combination of administration of a nitrobenzamide compound and surgery, radiation therapy, chemotherapy endocrine therapy, or a combination thereof.

Cervical Cancer

In another aspect, the invention provides a method of treating cervical cancer, preferably an adenocarcinoma in the cervix epithelial. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

The chief treatments available for cervical cancer are surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy. Anti-cancer drugs that may be administered as part of chemotherapy to treat cervical cancer include cisplatin, carboplatin, hydroxyurea, irinotecan, bleomycin, vincristine, mitomycin, ifosfamide, fluorouracil, etoposide, methotrexate, and combinations thereof.

The methods provided by the invention can provide a beneficial effect for cervical cancer patients, by administration of a nitrobenzamide compound or a combination of administration of a nitrobenzamide compound and surgery, radiation therapy, chemotherapy, or a combination thereof.

Prostate Cancer

In one other aspect, the invention provides methods to treat prostate cancer, preferably a prostate cancer selected from the following: an adenocarcinoma or an adenocarcinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

Surgery, immunotherapy, radiation therapy, cryosurgery, hormone therapy, and chemotherapy are some treatments available for prostate cancer patients. Possible surgical procedures to treat prostate cancer include radical retropubic prostatectomy, a radical perineal prostatectomy, and a laparscopic radical prostatectomy. Some radiation therapy options are external beam radiation, including three dimensional conformal radiation therapy, intensity modulated radiation therapy, and conformal proton beam radiation therapy. Brachytherapy (seed implantation or interstitial radiation therapy) is also an available method of treatment for prostate cancer. Cryosurgery is another possible method used to treat localized prostate cancer cells.

Hormone therapy, also called androgen deprivation therapy or androgen suppression therapy, may be used to treat prostate cancer. Several methods of this therapy are available including an orchiectomy in which the testicles, where 90% of androgens are produced, are removed. Another method is the administration of luteinizing hormone-releaseing hormone (LHRH) analogs to lower androgen levels. The LHRH analogs available include leuprolide, goserelin, triptorelin, and histrelin. An LHRH antagonist may also be administered, such as abarelix.

Treatment with an antiandrogen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB).

Chemotherapy may be appropriate where a prostate tumor has spread outside the prostate gland and hormone treatment is not effective. Anti-cancer drugs such as doxorubicin, estramustine, etoposide, mitoxantrone, vinblastine, paclitaxel, docetaxel, carboplatin, and prednisone may be administered to slow the growth of prostate cancer, reduce symptoms and improve the quality of life.

The methods provided by the invention can provide a beneficial effect for prostate cancer patients, by administration of a nitrobenzamide compound or a combination of administration of a nitrobenzamide compound and surgery, radiation therapy, chemotherapy, hormone therapy, or a combination thereof.

Pancreatic Cancer

In another aspect, the invention provides methods of treating pancreatic cancer, preferably a pancreatic cancer selected from the following: an epitheliod carcinoma in the pancreatic duct tissue and an adenocarcinoma in a pancreatic duct.

The most common type of pancreatic cancer is an adenocarcinoma, which occurs in the lining of the pancreatic duct. The possible treatments available for pancreatic cancer are surgery, immunotherapy, radiation therapy, and chemotherapy. Possible surgical treatment options include a distal or total pancreatectomy and a pancreaticoduodenectomy (Whipple procedure).

Radiation therapy may be an option for pancreatic cancer patients, specifically external beam radiation where radiation is focused on the tumor by a machine outside the body. Another option is intraoperative electron beam radiation administered during an operation.

Chemotherapy may be used to treat pancreatic cancer patients. Appropriate anti-cancer drugs include 5-fluorouracil (5-FU), mitomycin, ifosfamide, doxorubicin, streptozocin, chlorozotocin, and combinations thereof.

The methods provided by the invention can provide a beneficial effect for pancreatic cancer patients, by administration of a nitrobenzamide compound or a combination of administration of a nitrobenzamide compound and surgery, radiation therapy, or chemotherapy.

Bladder Cancer

In another aspect, the invention provides methods of treating bladder cancer, preferably a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

To treat bladder cancer, surgery, radiation therapy, immunotherapy, chemotherapy, or a combination thereof may be applied. Some possible surgical options are a transurethral resection, a cystectomy, or a radical cystectomy. Radiation therapy for bladder cancer may include external beam radiation and brachytherapy.

Immunotherapy is another method that may be used to treat a bladder cancer patient. Typically this is accomplished intravesically, which is the administration of a treatment agent directly into the bladder by way of a catheter. One method is Bacillus Calmete-Guerin (BCG) where a bacterium sometimes used in tuberculosis vaccination is given directly to the bladder through a catheter. The body mounts an immune response to the bacterium, thereby attacking and killing the cancer cells.

Another method of immunotherapy is the administration of interferons, glycoproteins that modulate the immune response. Interferon alpha is often used to treat bladder cancer.

Anti-cancer drugs that may be used in chemotherapy to treat bladder cancer include thitepa, methotrexate, vinblastine, doxorubicin, cyclophosphamide, paclitaxel, carboplatin, cisplatin, ifosfamide, gemcitabine, or combinations thereof.

The methods provided by the invention can provide a beneficial effect for bladder cancer patients, by administration of a nitrobenzamide compound or a combination of administration of a nitrobenzamide compound and surgery, radiation therapy, immunotherapy, chemotherapy, or a combination thereof.

Acute Myeloid Leukemia

In another aspect, the invention provides methods of treating acute myeloid leukemia (AML), preferably acute promyleocytic leukemia in peripheral blood. AML begins in the bone marrow but can spread to other parts of the body including the lymph nodes, liver, spleen, central nervous system, and testes. It is acute meaning it develops quickly and may be fatal if not treated within a few months. AML is characterized by immature bone marrow cells usually granulocytes or monocytes, which continue to reproduce and accumulate.

AML may be treated by immunotherapy, radiation therapy, chemotherapy, bone marrow or peripheral blood stem cell transplantation, or a combination thereof. Radiation therapy includes external beam radiation and may have side effects. Anti-cancer drugs that may be used in chemotherapy to treat AML include cytarabine, anthracycline, anthracenedione, idarubicin, daunorubicin, idarubicin, mitoxantrone, thioguanine, vincristine, prednisone, etoposide, or a combination thereof.

Monoclonal antibody therapy may be used to treat AML patients. Small molecules or radioactive chemicals may be attached to these antibodies before administration to a patient in order to provide a means of killing leukemia cells in the body. The monoclonal antibody, gemtuzumab ozogamicin, which binds CD33 on AML cells, may be used to treat AML patients unable to tolerate prior chemotherapy regimens.

Bone marrow or peripheral blood stem cell transplantation may be used to treat AML patients. Some possible transplantation procedures are an allogenic or an autologous transplant.

The methods provided by the invention can provide a beneficial effect for leukemia patients, by administration of a nitrobenzamide compound or a combination of administration of a nitrobenzamide compound and surgery, radiation therapy, chemotherapy, or transplantation therapy.

There are other types of leukemia's that can also be treated by the methods provided by the invention including but not limited to, Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders.

Lung Cancer

In another aspect, the invention provides methods to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers. Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy.

Some anti-cancer drugs that may be used in chemotherapy to treat lung cancer include cisplatin, carboplatin, paclitaxel, docetaxel, gemcitabine, vinorelbine, irinotecan, etoposde, vinblastine, gefitinib, ifosfamide, methotrexate, or a combination thereof. Photodynamic therapy (PDT) may be used to treat lung cancer patients.

The methods provided by the invention can provide a beneficial effect for lung cancer patients, by administration of a nitrobenzamide compound or a combination of administration of a nitrobenzamide compound and surgery, radiation therapy, chemotherapy, photodynamic therapy, or a combination thereof.

Skin Cancer

In another aspect, the invention provides methods to treat skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body. Different types of treatment are available for patients with non-melanoma and melanoma skin cancer and actinic keratosis including surgery, radiation therapy, chemotherapy and photodynamic therapy. Some possible surgical options for treatment of skin cancer are mohs micrographic surgery, simple excision, electrodesiccation and curettage, cryosurgery, laser surgery. Radiation therapy may be external beam radiation therapy or brachytherapy. Other types of treatments that are being tested in clinical trials are biologic therapy or immunotherapy, chemoimmunotherapy, topical chemotherapy with fluorouracil and photodynamic therapy.

The methods provided by the invention can provide a beneficial effect for skin cancer patients, by administration of a nitrobenzamide compound or a combination of administration of a nitrobenzamide compound and surgery, radiation therapy, chemotherapy, photodynamic therapy, or a combination thereof.

Eye Cancer, Retinoblastoma

In another aspect, the invention provides methods to treat eye retinoblastoma. Retinoblastoma is a malignant tumor of the retina. Although retinoblastoma may occur at any age, it most often occurs in younger children, usually before the age of 5 years. The tumor may be in one eye only or in both eyes. Retinoblastoma is usually confined to the eye and does not spread to nearby tissue or other parts of the body. Treatment options that attempt to cure the patient and preserve vision include enucleation (surgery to remove the eye), radiation therapy, cryotherapy, photocoagulation, immunotherapy, thermotherapy and chemotherapy. Radiation therapy may be external beam radiation therapy or brachytherapy.

The methods provided by the invention can provide a beneficial effect for eye retinoblastoma patients, by administration of a nitrobenzamide compound or a combination of administration of a nitrobenzamide compound and surgery, radiation therapy, cryotherapy, photocoagulation, thermotherapy and chemotherapy, or a combination thereof.

Eye Cancer, Intraocular Melanoma

In another aspect, the invention provides methods to treat intraocular (eye) melanoma. Intraocular melanoma, a rare cancer, is a disease in which cancer cells are found in the part of the eye called the uvea. The uvea includes the iris, the ciliary body, and the choroid. Intraocular melanoma occurs most often in people who are middle aged. Treatments for intraocular melanoma include surgery, immunotherapy, radiation therapy and laser therapy. Surgery is the most common treatment of intraocular melanoma. Some possible surgical options are iridectomy, iridotrabeculectomy, iridocyclectomy, choroidectomy, enucleation and orbital exenteration. Radiation therapy may be external beam radiation therapy or brachytherapy. Laser therapy may be an intensely powerful beam of light to destroy the tumor, thermotherapy or photocoagulation.

The methods provided by the invention can provide a beneficial effect for intraocular melanoma patients, by administration of a nitrobenzamide compound or a combination of administration of a nitrobenzamide compound and surgery, radiation therapy and laser therapy, or a combination thereof.

Endometrium Cancer

In another aspect, the invention provides methods to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

The methods provided by the invention can provide a beneficial effect for endometrium cancer patients, by administration of a nitrobenzamide compound or a combination of administration of a nitrobenzamide compound and surgery, radiation therapy, chemotherapy, gene therapy, photodynamic therapy, antiangiogenesis therapy, and immunotherapy, or a combination thereof.

Liver Cancer

In another aspect, the invention provides methods to treat primary liver cancer (cancer that begins in the liver). Primary liver cancer can occur in both adults and children. Different types of treatments are available for patients with primary liver cancer. These include surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

The methods provided by the invention can provide a beneficial effect for liver cancer patients, by administration of a nitrobenzamide compound or a combination of administration of a nitrobenzamide compound and surgery, radiation therapy, chemotherapy, percutaneous ethanol injection, hyperthemia therapy and immunotherapy, or a combination thereof.

Kidney Cancer

In another aspect, the invention provides methods to treat kidney cancer. Kidney cancer (also called renal cell cancer or renal adenocarcinoma) is a disease in which malignant cells are found in the lining of tubules in the kidney. Kidney cancer may be treated by surgery, radiation therapy, chemotherapy and immunotherapy. Some possible surgical options to treat kidney cancer are partial nephrectomy, simple nephrectomy and radical nephrectomy. Radiation therapy may be external beam radiation therapy or brachytherapy. Stem cell transplant may be used to treat kidney cancer.

The methods provided by the invention can provide a beneficial effect for kidney cancer patients, by administration of a nitrobenzamide compound or a combination of administration of a nitrobenzamide compound and surgery, radiation therapy, chemotherapy, immunotherapy and stem cell transplant, or a combination thereof.

Thyroid Cancer

In another aspect, the invention provides methods to treat thyroid cancer. Thyroid cancer is a disease in which cancer (malignant) cells are found in the tissues of the thyroid gland. The four main types of thyroid cancer are papillary, follicular, medullary and anaplastic. Thyroid cancer may be treated by surgery, immunotherapy, radiation therapy, hormone therapy and chemotherapy. Surgery is the most common treatment of thyroid cancer. Some possible surgical options for treatment of thyroid cancer are lobectomy, near-total thyroidectomy, total thyroidectomy and lymph node dissection. Radiation therapy may be external radiation therapy or may required intake of a liquid that contains radioactive iodine. Hormone therapy uses hormones to stop cancer cells from growing. In treating thyroid cancer, hormones can be used to stop the body from making other hormones that might make cancer cells grow.

The methods provided by the invention can provide a beneficial effect for thyroid cancer patients, by administration of a nitrobenzamide compound or a combination of administration of a nitrobenzamide compound and surgery, surgery, radiation therapy, hormone therapy and chemotherapy, or a combination thereof.

AIDS Related Cancers

AIDS-Related Lymphoma

In another aspect, the invention provides methods to treat AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma may occur in AIDS patients, but non-Hodgkin's lymphoma is more common. When a person with AIDS has non-Hodgkin's lymphoma, it is called an AIDS-related lymphoma. Non-Hodgkin's lymphomas may be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Treatment of AIDS-related lymphoma combines treatment of the lymphoma with treatment for AIDS. Patients with AIDS have weakened immune systems and treatment can cause further damage. For this reason, patients who have AIDS-related lymphoma are usually treated with lower doses of drugs than lymphoma patients who do not have AIDS. Highly-active antiretroviral therapy (HAART) is used to slow progression of HIV. Medicine to prevent and treat infections, which can be serious, is also used. AIDS-related lymphomas may be treated by chemotherapy, immunotherapy, radiation therapy and high-dose chemotherapy with stem cell transplant. Radiation therapy may be external beam radiation therapy or brachytherapy. AIDS-related lymphomas can be treated by monoclonal antibody therapy.

The methods provided by the invention can provide a beneficial effect for AIDS-related lymphoma patients, by administration of a nitrobenzamide compound or a combination of administration of a nitrobenzamide compound and chemotherapy, radiation therapy and high-dose chemotherapy, or a combination thereof.

Kaposi's Sarcoma

In another aspect, the invention provides methods to treat Kaposi's sarcoma. Kaposi's sarcoma is a disease in which cancer cells are found in the tissues under the skin or mucous membranes that line the mouth, nose, and anus. Classic Kaposi's sarcoma usually occurs in older men of Jewish, Italian, or Mediterranean heritage. This type of Kaposi's sarcoma progresses slowly, sometimes over 10 to 15 years. Kaposi's sarcoma may occur in people who are taking immunosuppressants. Kaposi's sarcoma in patients who have Acquired Immunodeficiency Syndrome (AIDS) is called epidemic Kaposi's sarcoma. Kaposi's sarcoma in people with AIDS usually spreads more quickly than other kinds of Kaposi's sarcoma and often is found in many parts of the body. Kaposi's sarcoma may be treated with surgery, chemotherapy, radiation therapy and immunotherapy. External radiation therapy is a common treatment of Kaposi's sarcoma. Some possible surgical options to treat Kaposi's Sarcoma are local excision, electrodeiccation and curettage, and cryotherapy.

The methods provided by the invention can provide a beneficial effect for Kaposi's sarcoma, by administration of a nitrobenzamide compound or a combination of administration of a nitrobenzamide compound and surgery, chemotherapy, radiation therapy and immunotherapy, or a combination thereof.

Viral-Induced Cancers

In another aspect, the invention provides methods to treat viral-induced cancers. Several common viruses are clearly or probable causal factors in the etiology of specific malignancies. These viruses either normally establish latency or few can become persistent infections. Oncogenesis is probably linked to an enhanced level of viral activation in the infected host, reflecting heavy viral dose or compromised immune control. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer. In general, these malignancies occur relatively early in life, typically peaking in middle-age or earlier Virus-Induced Hepatocellular Carcinoma The causal relationship between both HBV and HCV and hepatocellular carcinoma or liver cancer is established through substantial epidemiologic evidence. Both appear to act via chronic replication in the liver by causing cell death and subsequent regeneration. Different types of treatments are available for patients with liver cancer. These include surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

The methods provided by the invention can provide a beneficial effect for virus induce hepatocellular carcinoma patients, by administration of a nitrobenzamide compound or a combination of administration of a nitrobenzamide compound and surgery, radiation therapy, chemotherapy, percutaneous ethanol injection, hyperthemia therapy and immunotherapy, or a combination thereof.

Viral-Induced Adult T Cell Leukemia/Lymphoma

The association between HTLV-1 and Adult T cell leukemia (ATL) is firmly established. Unlike the other oncogenic viruses found throughout the world, HTLV-1 is highly geographically restricted, being found primarily in southern Japan, the Caribbean, west and central Africa, and the South Pacific islands. Evidence for causality includes the monoclonal integration of viral genome in almost all cases of ATL in carriers. The risk factors for HTLV-1-associated malignancy appear to be perinatal infection, high viral load, and being male sex.

Adult T cell leukemia is a cancer of the blood and bone marrow. The standard treatments for adult T cell leukemia/lymphoma are radiation therapy, immunotherapy, and chemotherapy. Radiation therapy may be external beam radiation therapy or brachytherapy. Other methods of treating adult T cell leukemia/lymphoma include immunotherapy and high-dose chemotherapy with stem cell transplantion.

The methods provided by the invention can provide a beneficial effect for Adult T cell leukemia patients, by administration of a nitrobenzamide compound or a combination of administration of a nitrobenzamide compound and radiation therapy, chemotherapy, immunotherapy and high-dose chemotherapy with stem cell transplantion, or a combination thereof.

Viral-Induced Cervical Cancer

Infection of the cervix with human papillomavirus (HPV) is the most common cause of cervical cancer. Not all women with HPV infection, however, will develop cervical cancer. Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas. The standard treatments for cervical cancers are surgery, immunotherapy, radiation therapy and chemotherapy. The types of surgery that may be used are conization, total hysterectomy, bilateral salpingo-oophorectomy, radical hysterectomy, pelvic exenteration, cryosurgery, laser surgery and loop electrosurgical excision procedure. Radiation therapy may be external beam radiation therapy or brachytherapy.

The methods provided by the invention can provide a beneficial effect for adult cervical cancer, by administration of a nitrobenzamide compound or a combination of administration of a nitrobenzamide compound and radiation therapy, chemotherapy, or a combination thereof.

CNS Cancers

Brain and spinal cord tumors are abnormal growths of tissue found inside the skull or the bony spinal column, which are the primary components of the central nervous system (CNS). Benign tumors are noncancerous, and malignant tumors are cancerous. The CNS is housed within rigid, bony quarters (i.e., the skull and spinal column), so any abnormal growth, whether benign or malignant, can place pressure on sensitive tissues and impair function. Tumors that originate in the brain or spinal cord are called primary tumors. Most primary tumors are caused by out-of-control growth among cells that surround and support neurons. In a small number of individuals, primary tumors may result from specific genetic disease (e.g., neurofibromatosis, tuberous sclerosis) or from exposure to radiation or cancer-causing chemicals. The cause of most primary tumors remains a mystery.

The first test to diagnose brain and spinal column tumors is a neurological examination. Special imaging techniques (computed tomography, and magnetic resonance imaging, positron emission tomography) are also employed. Laboratory tests include the EEG and the spinal tap. A biopsy, a surgical procedure in which a sample of tissue is taken from a suspected tumor, helps doctors diagnose the type of tumor.

Tumors are classified according to the kind of cell from which the tumor seems to originate. The most common primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme) and account for 65% of all primary central nervous system tumors. Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma, anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma, anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma;

astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the Sellar Region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumours, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

Chemotherapeutics available are, but not limited to, alkylating agents such as, Cyclophosphamide, Ifosphamide, Melphalan, Chlorambucil, BCNU, CCNU, Decarbazine, Procarbazine, Busulfan, and Thiotepa; antimetabolites such as, Methotraxate, 5-Fluorouracil, Cytarabine, Gemcitabine (Gemzar®), 6-mercaptopurine, 6-thioguanine, Fludarabine, and Cladribine; anthracyclins such as, daunorubicin. Doxorubicin, Idarubicin, Epirubicin and Mitoxantrone; antibiotics such as, Bleomycin; camptothecins such as, irinotecan and topotecan; taxanes such as, paclitaxel and docetaxel; and platinums such as, Cisplatin, carboplatin, and Oxaliplatin.

The treatments are surgery, radiation therapy, immunotherapy, hyperthermia, gene therapy, chemotherapy, and combination of radiation and chemotherapy. Doctors also may prescribe steroids to reduce the swelling inside the CNS.

The methods provided by the invention can provide a beneficial effect for adult cervical cancer, by administration of a nitrobenzamide compound or a combination of administration of a nitrobenzamide compound and radiation therapy, chemotherapy, or a combination thereof.

PNS Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. These tumors are non-malignant, meaning that they do not spread or metastasize to other parts of the body. The location of these tumors is deep inside the skull, adjacent to vital brain centers in the brain stem. As the tumors enlarge, they involve surrounding structures which have to do with vital functions. In the majority of cases, these tumors grow slowly over a period of years.

The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus. The most common symptom is pain which usually prompts a biopsy. It is a rare, aggressive, and lethal orbital neoplasm that usually arises from sensory branches of the trigeminal nerve in adults. Malignant PNS tumor spreads along nerves to involve the brain, and most patients die within 5 years of clinical diagnosis. The MPNST may be classified into three major categories with epithelioid, mesenchymal or glandular characteristics. Some of the MPNST include but not limited to, Subcutaneous malignant epithelioid schwannoma with cartilaginous differentiation, Glandular malignant schwannoma, Malignant peripheral nerve sheath tumor with perineurial differentiation, Cutaneous epithelioid malignant nerve sheath tumor with rhabdoid features, Superficial epithelioid MPNST, Triton Tumor (MPNST with rhabdomyoblastic differentiation), Schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

The treatments are surgery, radiation therapy, immunotherapy, chemotherapy, and combination of radiation and chemotherapy.

The methods provided by the invention can provide a beneficial effect for PNS cancers, by administration of a nitrobenzamide compound or a combination of administration of a nitrobenzamide compound and radiation therapy, chemotherapy, or a combination thereof.

Oral Cavity and Oropharyngeal Cancer

Management of patients with central nervous system (CNS) cancers remains a formidable task. Cancers such as, hypopharyngeal cancer, laryngeal cancer, nasopharyngeal cancer, oropharyngeal cancer, and the like, have been treated with surgery, immunotherapy, chemotherapy, combination of chemotherapy and radiation therapy. Etoposide and actinomycin D, two commonly used oncology agents that inhibit topoisomerase II, fail to cross the blood-brain barrier in useful amounts.

The methods provided by the invention can provide a beneficial effect for Oral Cavity and Oropharyngeal cancer, by administration of a nitrobenzamide compound or a combination of administration of a nitrobenzamide compound and radiation therapy, chemotherapy, or a combination thereof.

Stomach Cancer

Stomach cancer is the result of cell changes in the lining of the stomach. There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach.

The causes of stomach cancer continue to be debated. A combination of heredity and environment (diet, smoking, etc) are all thought to play a part. Common approaches to the treatment include surgery, immunotherapy, chemotherapy, radiation therapy, combination of chemotherapy and radiation therapy or biological therapy.

The methods provided by the invention can provide a beneficial effect for stomach cancer, by administration of a nitrobenzamide compound or a combination of administration of a nitrobenzamide compound and radiation therapy, chemotherapy, or a combination thereof.

Testicular Cancer

Testicular cancer is cancer that typically develops in one or both testicles in young men. Cancers of the testicle develop in certain cells known as germ cells. The 2 main types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The 2 main types are Leydig cell tumors and Sertoli cell tumors. Secondary testicular tumors are those that start in another organ and then spread to the testicle. Lymphoma is the most common secondary testicular cancer.

Common approaches to the treatment include surgery, immunotherapy, chemotherapy, radiation therapy, combination of chemotherapy and radiation therapy or biological therapy. Several drugs are typically used to treat testicular cancer: Platinol (cisplatin), Vepesid or VP-16 (etoposide) and Blenoxane (bleomycin sulfate). Additionally, Ifex (ifosamide), Velban (vinblastine sulfate) and others may be used.

The methods provided by the invention can provide a beneficial effect for stomach cancer, by administration of a nitrobenzamide compound or a combination of administration of a nitrobenzamide compound and radiation therapy, chemotherapy, or a combination thereof.

Thymus Cancer

The thymus is a small organ located in the upper/front portion of your chest, extending from the base of the throat to the front of the heart. The thymus contains 2 main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus also contains another much less common type of cells called Kulchitsky cells, or neuroendocrine cells, which normally release certain hormones. These cells can give rise to cancers, called carcinoids or carcinoid tumors that often release the same type of hormones, and are similar to other tumors arising from neuroendocrine cells elsewhere in the body.

Common approaches to the treatment include surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone). Often, these drugs are given in combination to increase their effectiveness. Combinations used to treat thymic cancer include cisplatin, doxorubicin, etoposide and cyclophosphamide, and the combination of cisplatin, doxorubicin, cyclophosphamide, and vincristine.

The methods provided by the invention can provide a beneficial effect for stomach cancer, by administration of a nitrobenzamide compound or a combination of administration of a nitrobenzamide compound and radiation therapy, chemotherapy, or a combination thereof.

Combination Therapy

One aspect of the invention provides methods for treating cancer using different combinations of treatment regimens. For example, such combinations may include, but are not limited to, the use of one or more of the nitrobenzamide compounds in conjunction with one or more various antineoplastic chemotherapeutic agents, chemopreventative agents, and/or side-effect limiting agents.

Antineoplastic Chemotherapeutic Agents

Suitable antineoplastic chemotherapeutic agents to be used in the present invention include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and antimetastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Antineoplastic Agents

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD121974, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

RNA Inhibitors

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sima-027, fomivirsen, and angiozyme.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents can be used to prevent initial occurrences of cancer, or to prevent recurrence or metastasis. Administration with such chemopreventative agents in combination with one or more other anticancer agents including the nitrobenzamide compounds can act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylomithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in the present invention is cancer vaccines. These can be created through immunizing a patient with all or part of a cancer cell type that is targeted by the vaccination process.

Side-Effect Limiting Agents

Treatment of cancer with nitrobenzamide compounds alone or in combination with other antineoplastic compounds may be accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with the nitrobenzamide compounds and other compounds described herein are also available. For example, see *Goodman & Gilman's The Pharmacological Basis of Therapeutics* 11th ed. Brunton L L, Lazo J S, and Parker K L, ed. McGraw-Hill, New York, 2006.

Formulations, Routes of Administration, and Effective Doses

Another aspect of the present invention relates to formulations and routes of administration for pharmaceutical compositions comprising a nitrobenzamide compound. Such pharmaceutical compositions can be used to treat cancer in the methods described in detail above.

The compounds of formula Ia may be provided as a pro-drug and/or may be allowed to interconvert to a nitrosobenzamide form in vivo after administration. That is, either the nitrobenzamide form and/or the nitrosobenzamide form, or pharmaceutically acceptable salts may be used in developing a formulation for use in the present invention. Further, in some embodiments, the compound may be used in combination with one or more other compounds or in one or more other forms. For example a formulation may comprise both the nitrobenzamide compound and acid forms in particular proportions, depending on the relative potencies of each and the intended indication. The two forms may be formulated together, in the same dosage unit e.g. in one cream, suppository, tablet, capsule, or packet of powder to be dissolved in a beverage; or each form may be formulated in a separate unit, e.g., two creams, two suppositories, two tablets, two capsules, a tablet and a liquid for dissolving the tablet, a packet of powder and a liquid for dissolving the powder, etc.

In compositions comprising combinations of a nitrobenzamide compound and another active agent can be effective. The two compounds and/or forms of a compound may be formulated together, in the same dosage unit e.g. in one cream, suppository, tablet, capsule, or packet of powder to be dissolved in a beverage; or each form may be formulated in separate units, e.g., two creams, suppositories, tablets, two capsules, a tablet and a liquid for dissolving the tablet, a packet of powder and a liquid for dissolving the powder, etc.

The term "pharmaceutically acceptable salt" means those salts which retain the biological effectiveness and properties of the compounds used in the present invention, and which are not biologically or otherwise undesirable. For example, a pharmaceutically acceptable salt does not interfere with the beneficial effect of the compound of the invention in treating a cancer.

Typical salts are those of the inorganic ions, such as, for example, sodium, potassium, calcium and magnesium ions. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

For oral administration, the compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the compounds of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions may contain a nitrobenzamide compound with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In some embodiments, oils or non-aqueous solvents may be required to bring the compounds into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., J. Mol. Biol, 23: 238-252 (1965) and Szoka et al., Proc. Natl. Acad. Sci. 75: 4194-4198 (1978), incorporated herein by reference. Ligands may also be attached to the liposomes to direct these compositions to particular sites of action. Compounds of this invention may also be integrated into foodstuffs, e.g, cream cheese, butter, salad dressing, or ice cream to facilitate solubilization, administration, and/or compliance in certain patient populations.

Pharmaceutical preparations for oral use may be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

For injection, the inhibitors of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P. These compounds may also be formulated for transmucosal administration, buccal administration, for administration by inhalation, for parental administration, for transdermal administration, and rectal administration.

In addition to the formulations described previously, the compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for use in the present invention include compositions wherein the active ingredients are present in an effective amount, i.e., in an amount effective to achieve therapeutic and/or prophylactic benefit in at least one of the cancers described herein. The actual amount effective for a particular application will depend on the condition or conditions being treated, the condition of the subject, the formulation, and the route of administration, as well as other factors known to those of skill in the art. Determination of an effective amount of a nitrobenzamide compound is well within the capabilities of those skilled in the art, in light of the disclosure herein, and will be determined using routine optimization techniques.

EXAMPLES

Example 1

In Vitro Studies—Cytotoxicity Assays

Different types of cancer cell lines of different origin or primary cells were seeded ($5 \times 10^4$) on 48 wells plate, or ($2 \times 10^4$) on 96 wells plate. The cells were cultured in the appropriate medium. Cultures were maintained in a 37° C. incubator in a humidified atmosphere of 95% $O_2$/5% $CO_2$.

After the cells were seeded (24 hours), medium was removed and replaced with culture medium in the presence of various concentrations of INO2BA or INH2BP, in the presence or not of 200 μM BSO. After 6 days of incubation at 37° C., cell viability was measured using the Cell Titer-Blue, Cell Viability Assay (Promega) (See O'Brien, J. et al. (2000) Investigation of the Alamar Blue (resazurin) fluorescent dye for the assessment of mammalian cell cytotoxicity. Eur. J. Biochem. 267, 5421-26 and Gonzalez, R. J. and Tarloff, J. B. (2001) Evaluation of hepatic subcellular fractions for Alamar Blue and MTT reductase). This assay incorporates a fluorometric/colorometric growth indicator based on detection by vital dye reduction. Cytotoxicity is measured by growth inhibition.

Cytotoxicity was also assessed by counting the number of viable cells. Cells were harvested by washing the monolayer with PBS, followed by a brief incubation in 0.25% trypsin and 0.02% EDTA. The cells were then collected, washed twice by centrifugation and resuspended in PBS. Cell number and viability were determined by staining a small volume of cell suspension with a 0.2% trypan blue saline solution and examining the cells in a hemocytometer. See Kerley-Hamilton et al. (2005) p53-dominant transcriptional response to cisplatin in testicular germ cell tumor-derived human embryonal carcinoma and Cheol et al. (2005) Induction of apoptosis and inhibition of cyclooxygenase-2 expression by N-methyl-N'-nitro-N-nitrosoguanidine in human leukemia cells.

The results of this cell proliferation assay using different cell lines are shown in FIGS. 1-10.

Example 2

Cell Proliferation Measured with BrdU-ELISA

The cells were incubated in the presence of various concentrations of the test substance (drugs) in a black 96-well MP (tissue culture grade; flat, clear bottom) at a final volume of 100 μl/well in a humidified atmosphere at 37° C. 10 μl/well BrdU labeling solution was added if the cells were cultured in 100 μl/well (final concentration: 10 μM BrdU) and the cells were reincubated for additional 2 to 24 hours at 37° C. (if the cells were cultured in 200 μl/well, 20 μl/well BrdU labeling solution was added). The MP was centrifuged at 300×g for 10 min and the labeling medium was removed with suction using a canulla. The cells were dried using a hair-dryer for about 15 min or, alternatively, at 60° C. for 1 h. 200 μl/well FixDenat was added to the cells and incubated for 30 min at 15-25° C. FixDenat solution was removed thoroughly by flicking off and tapping. 100 μl/well Anti-BrdU-POD working solution was added. This was incubated for approx. 90 min at 15-25° C. Alternatively, this incubation period was varied between 30-120 min, depending on individual requirements. Antibody conjugate was removed by flicking off and wells were rinsed three times with 200-300 μl/well washing solution. Washing solution was removed by tapping. The clear bottom was sealed with a black adhesive foil and 100 μl/well substrate solution was added to each well with a multi-channel pipette. The light emission of the samples was measured in a microplate luminometer with photomultiplier.

Figure 11:
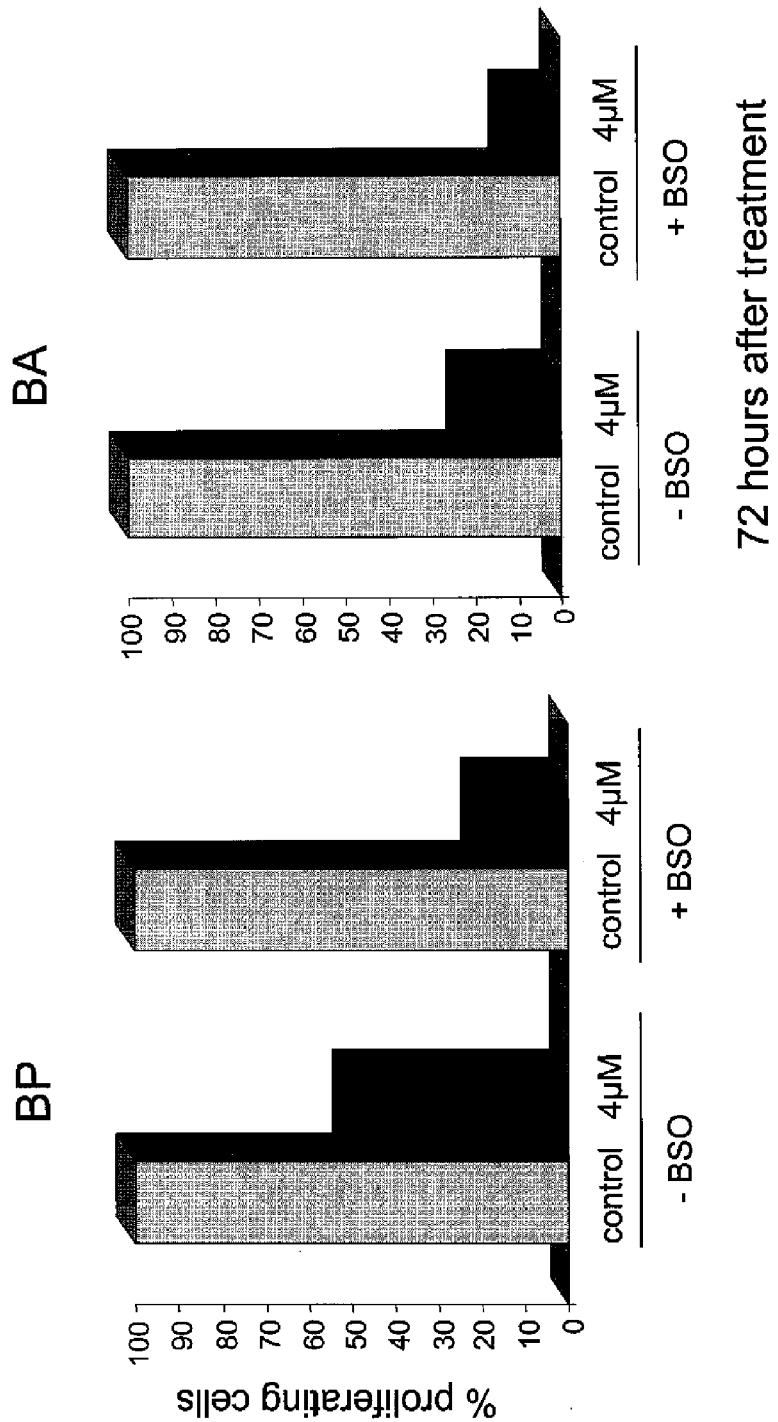
FIG. 11 depicts the effect of nitrobenzamide and benzopyrone compounds on a cervical cancer cell line, with and without the co-treatment of BSO.

The results of this cell proliferation assay using different cell lines and drugs are shown in FIG. 11.

Example 3

| | | Study Design | | | |
|---|---|---|---|---|---|
| Group | Implant conditions | Cells implanted | # Mice | # Tumors needed | Treatment (BID) |
| 1 | sc | 2 × 10⁷ | 20 | 10 | none |
| 2 | sc | 2 × 10⁷ | 20 | 10 | Vehicle (10% DMSO in saline) |
| 3 | sc | 2 × 10⁷ | 20 | 10 | BP + BSO (175 mg/kg + 220 mg/kg) P.O. |
| 4 | sc | 2 × 10⁷ | 20 | 10 | BA (5 g/kg) I.P. |
| 5 | sc | 2 × 10⁷ | 20 | 10 | Combo* (30 mg/kg) I.P. and P.O. |

Figure 12:
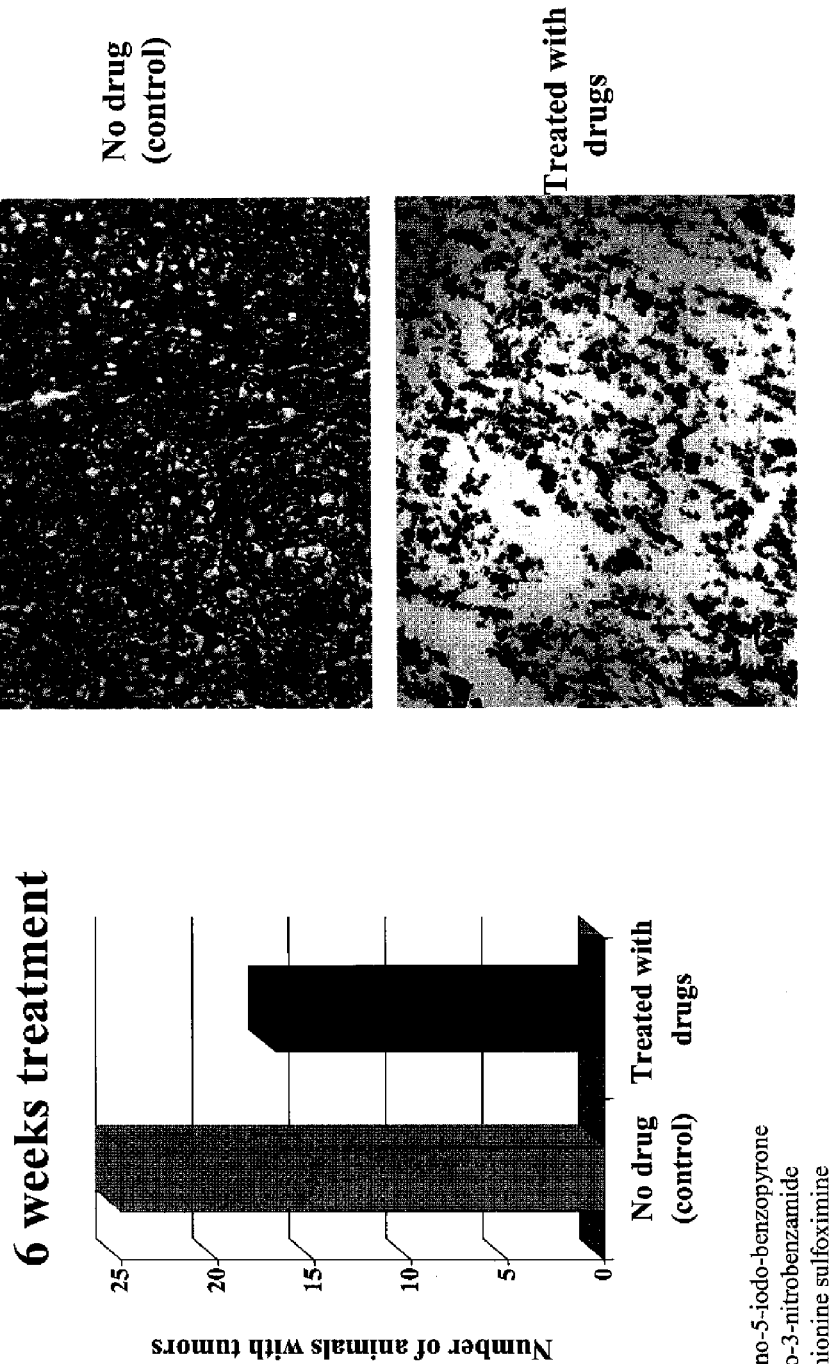
FIG. 12 depicts the effect of nitrobenzamide and benzopyrone compounds on an in vivo subcutaneous breast cancer model, with and without the co-treatment of BSO.

*combination of BP + BSO and BA 100 female NU/NU-nuBR mice (Charles River, 5-6 wks) were implanted with 0.72 mg 17 β-estradiol (human) pellets, ear tagged using clips and weighed 24-48 hours prior to tumor cell implantation. Tumor cells, BT474, (2×10⁷ cells/mouse) were injected into the subscapular mammary fat pad (0.2 ml volume). Caliper measurements began on day 21 and three times weekly thereafter (Mon. Wed, Fri). Animals were segregated according to the presence and absence of tumor and then by tumor volume. Animals were weighed twice weekly beginning the 3$^{rd}$ week post implantation (Mon and Fri.). Drug treatment was started when tumor sizes were 150-250 mm³ (L*W*H). Drug and vehicle administration was BID by gavage (BP+BSO) and SID by IP (BA) for five days. There was a two day rest period before the next cycle began. It was planned that animals received three cycles (5 days each) unless there was unexpected toxicity. Body weight loss that exceeded 15% of initial values or display of certain symptoms was criteria for animal euthanasia. Drug was administered by gavage and IP in volume of 5 ml/kg. Drug and vehicle were stored at 4° C. in foil-covered bottle. Results of this experiment are shown in FIG. 12.

Example 4

The effects of the compounds were evaluated on ovarian human cancer cells (OVCAR) xenografts in nude mice.

Female NU/NU 37-BU-04-BAC mice (Charles River, 5-6 weeks) were ear tagged using clips and weighed 24-48 hours prior to tumor cell implantation. Tumor cells Ovcar3 (5×10⁶ cells/mouse) were implanted subcutaneously into the subcapular mammary fat pad of female nude mice hosts. Caliper measurement began on day 7 post tumor cells implantation and 2 times weekly thereafter (Mon and Fri). Animals were segregated according to the presence or absence of tumor and then tumor volume. Animals were weighed once a week. Drug treatment started when sizes were 0.4-0.5 cm in largest diameter. 4-Iodo-3-nitrobenzamide (BA) (in 50 μl of 100% DMSO/mouse and vehicle (50 μl of 100% DMSO/mouse) were injected by IP twice per day for five days. There was a two days rest period before the next cycle began.

| STUDY DESIGN | | | |
|---|---|---|---|
| Group | Implant conditions | Cells implanted | TREATMENT |
| 1 | SC | $5 \times 10^6$ | Vehicle × 2 (50 μl of 100% DMSO/mouse) |
| 2 | SC | $5 \times 10^6$ | BA 25 mg/kg × 2/day (in 50 μl of 100% DMSO/mouse) |
| 3 | SC | $5 \times 10^6$ | BA 50 mg/kg × 2/day (in 50 μl of 100% DMSO/mouse) |
| 4 | SC | $5 \times 10^6$ | Nothing (Control) |

Figure 13:
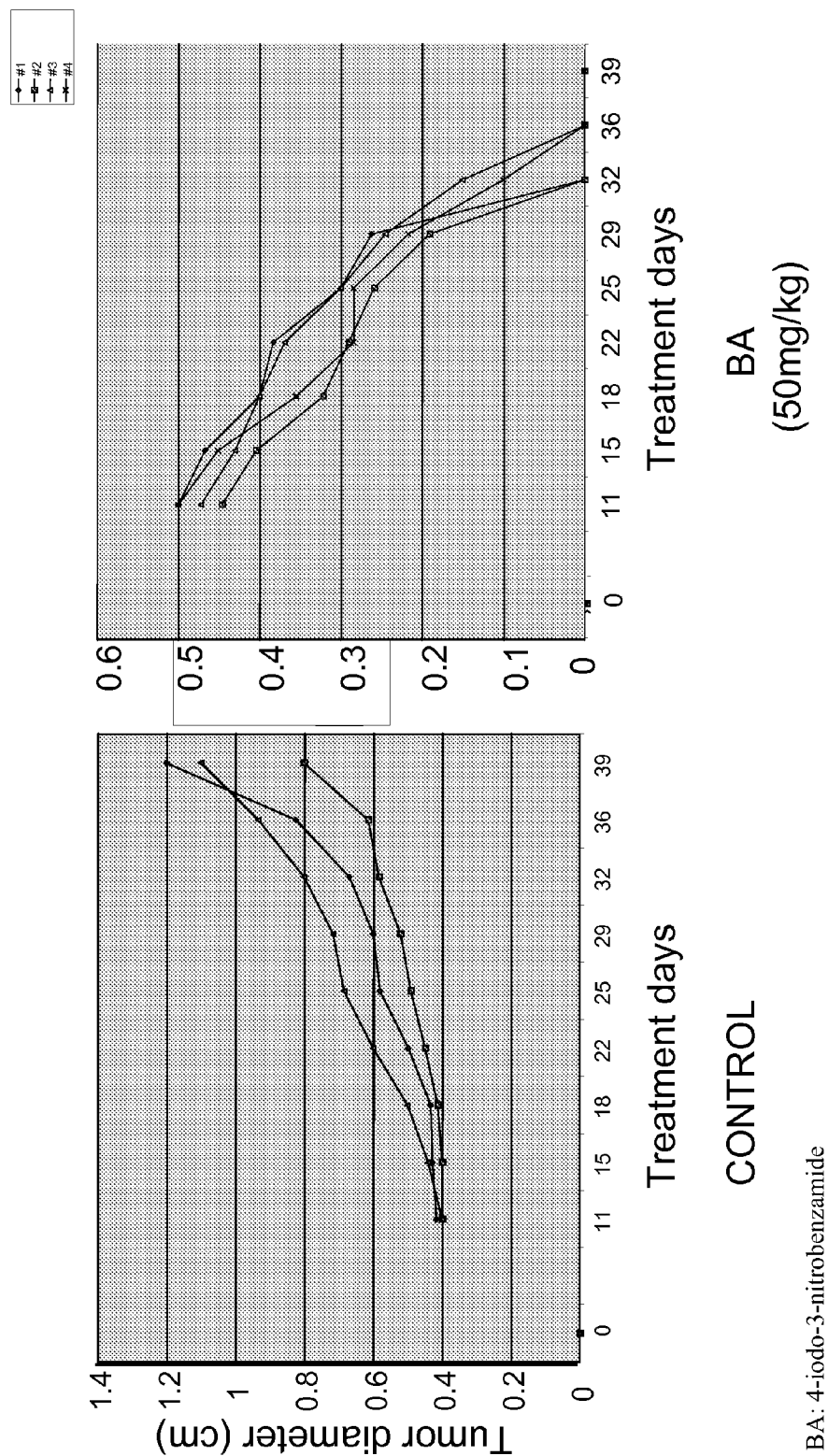
FIG. 13 depicts the effect of 4-Iodo-3-nitrobenzamide in OVCAR3 (human ovarian adenocarcinoma) xenograft model in nude mice.
Figure 14A:
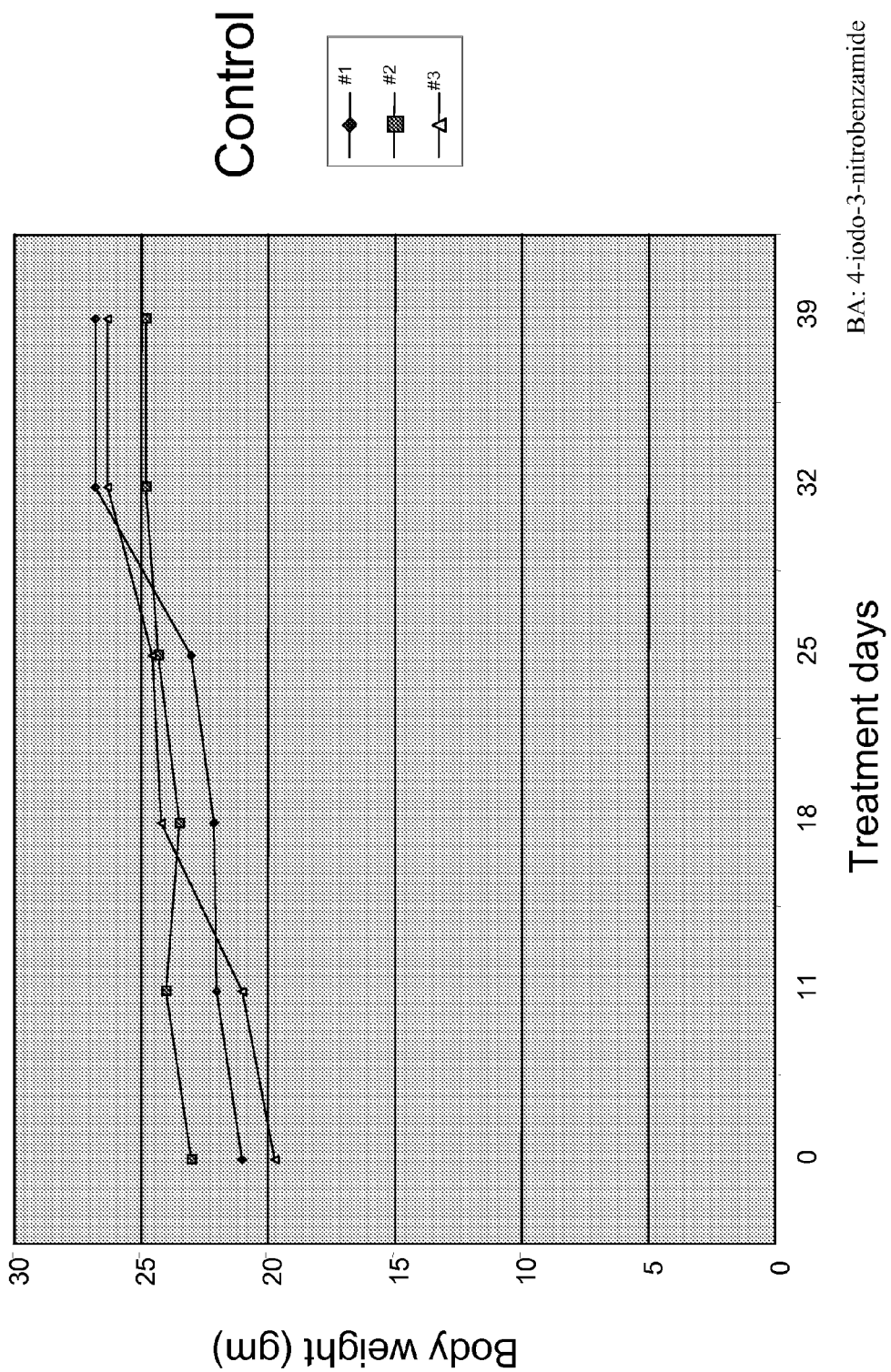
FIG. 14A and 14B depicts the effect on body weight during the evaluation of 4-Iodo-3-nitrobenzamide in OVCAR3 (human ovarian adenocarcinoma) xenograft model in nude mice.
Figure 14B:
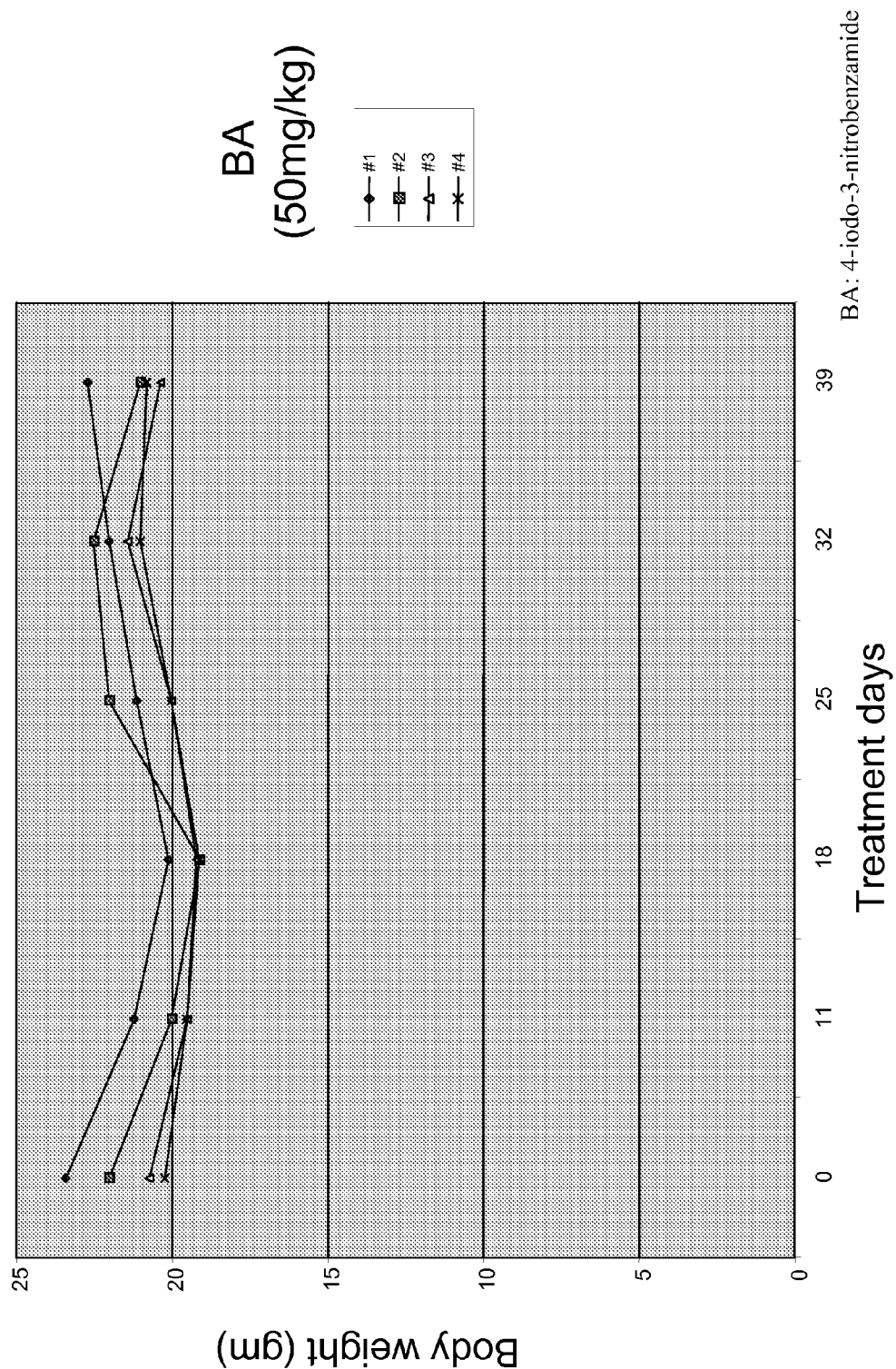

Results of the experiments are shown in FIGS. 13 and 14.

Example 5

The objective of this study was to evaluate the efficacy of the coumarin analog 6-amino-5-iodo-2H-1-benzopyran-2-one (BP) in mammary (MDA MB 231) cancer nude mouse xenografts.

Tumor-bearing female mice were treated 5 days a week, Monday through Friday, with BP (two dose levels). The study was divided into two tasks: Task 1 was to test the effect of pretreating the animals with BP prior to tumor implantation, and Task 2 was to test the effect of initiating treatment after tumors had formed. For Task 1, female nude mice were pretreated with BP (either 300 or 1000 mg/kg) for one week, tumor cells were then implanted subcutaneously, and treatment continued for 4-8 weeks with oral doses of either corn oil:PEG 400 or BP. In Task 2, BP was compared to chemotherapeutic agents used clinically. Female nude mice bearing tumors of 20-30 mm3 (MDA MB 231) were treated five times a week with oral doses of either corn oil:PEG 400, BP, or cyclophosphamide (CTX, positive control for MDA MB 231). Treatment for the MDA MB 231 tumors was continued until the tumors of each animal reached $\geq 1600$ mm$^3$ or ulcerated. Some MDA MB 231 tumors in Task 2 did not reach 1600 mm$^3$. Follow-up of regressed tumors continued for 3 months.

The MDA MB 231 mammary tumors responded to treatment with BP and CTX (positive control). In Task 1, BP at 300 mg/kg and 1000 mg/kg appeared to prevent tumor formation in 2/9 animals and 2/10 animals, respectively. All 8 control animals formed tumors. In Task 2, treatment of animals with BP (1000 mg/kg or 2000 mg/kg body weight) resulted in regression of 3/5 tumors.

General Methods

MDA MB 231 human mammary cancer cells were injected subcutaneously into the right flank of female nude mice. For Task 1, BP was administered for 5 consecutive days prior to tumor cell implantation, and drug administration continued 5 days a week for 4-8 weeks thereafter. For Task 2, cancer cells were injected when the tumors reached a mean tumor volume of 50-60 mm$^3$, and mice were divided into groups of eight and treated with corn oil:PEG 400 (control), BP, or CTX (MDA MB 231 positive control). Tumor volumes were monitored for 90 days (for MDA MB 231) after the beginning of treatment.

Experimental Procedures
Cell Lines

MDA MB 231 is a human mammary cancer cell line that was established in 1973 from a pleural effusion of a patient who had been treated with 5-FU, doxorubicin, methotrexate, and CTX in the 3 months before the cell line was initiated. This line is estrogen receptor negative and has been used in screening anticancer drugs that are not targeted as hormone antagonists. MDA MB 231 was grown in Dulbecco's modified Eagle medium (DMEM) with 1.5 g NaHCO$_3$/L, 10% fetal bovine serum (FBS), and 2 mM L-glutamine and was kept at 37° C. in a humidified 5% CO$_2$/air incubator. Antibiotics were not added to the medium.

Animal Tumor Model

Swiss NCr nude (nu/nu) female mice, age 4-5 weeks, were purchased from Taconic (Germantown, N.Y.). The animals were housed three per cage in sterile filter-topped cages in a barrier clean room purchased from Bio Bubble, Inc. (Fort Collins, Colo.). Upon arrival, they were quarantined for four working days before use. Temperature was maintained at 72±5° F. and relative humidity at 35-70%, and a 12-hr light/dark cycle was used. The mice were fed sterile, autoclavable, certified Purina rodent chow ad libitum. Drinking water was acidified and autoclaved, and the source water was recirculated, deionized, UV-treated, and 5 μm filtered.

After the animals were released from quarantine, the mice were injected subcutaneously in the right flank with 1 or 5×10$^6$ MDA MB 231 cells (0.1-ml injection volume). The mice for Task 1 received pretreatment for 5 days before cell injection. Tumor dimensions and body weight were measured twice weekly. Vernier calipers were used to measure tumors in three planes, and tumor volume (V) was calculated as follows: $V=\pi(x \times y \times z)/6$, where x, y, and z were the tumor measurements minus skin thickness. At the end of the experiment, the mice were sacrificed by CO$_2$ inhalation followed by cervical dislocation.

Pharmaceuticals

BP was made up in corn oil:PEG 400 (2:1, V/V) at concentrations of 30 mg/ml and 100 mg/ml. The drug was a suspension at these concentrations. Positive control drugs were made up on phosphate buffered saline (PBS) and CTX at 15 mg/ml. Both drugs were filter-sterilized (0.2-μm filter) before use.

Treatment Protocol

For Task 1, mice to be implanted with MDA MB 231 tumor cells were pretreated for 5 days with BP (300 or 1000 mg/kg), and following subcutaneous injection of the cell suspension, drug treatment was continued 5 days a week (Monday through Friday) for a minimum of 4 weeks.

For Task 2, after the tumor volumes reached a predetermined size (mean tumor volume 50-60 mm$^3$), mice were divided into treatment groups of eight mice each. All treatments of BP were administered five times per week (Monday through Friday) for at least 4 weeks. CTX was administered intraperitoneally one time only at a dose of 150 mg/kg. All BP treatments were administered orally; the dosage was 1000 or 2000 mg/kg for those implanted with MDA MB 231 cells. For each task, all treatments began on the same day.

The tumors were measured twice weekly for at least 9 weeks (MDA MB 231) after the first treatment. The mean tumor volume for each group was calculated for each time point. Comparisons between groups at specific times were made using an unpaired, two-tailed t-test, and the results were analyzed using analysis of variance (ANOVA). For Task 2, individual tumor volumes (V) were expressed as a fraction of the tumor volume on Day 0, the first day of treatment (V$_0$). For each group, the mean of the ratio V/V$_0$ was plotted as a function of time after treatment. Response to treatment was measured in two ways, depending on the tumor response to treatment. The tumor volume doubling time (VDT) and volume quadrupling time (VQT) were determined for each tumor by linear regressions on the plot of time as a function of log (tumor volume) in groups where there was a response to treatment. Tumor growth delay for each treatment group was determined and comparisons between groups were analyzed using ANOVA.

Systemic toxicity was assessed from reductions in body weight after treatment. The mice were sacrificed at the end of the follow-up period, or earlier in their tumor volumes reached 1600 mm$^3$ or the tumors ulcerated.

Statistical Analysis

Statistical analysis as described above was performed using InStat (Graphpad Software, San Diego, Calif.).

Tumor Growth

MDA MB 231 tumors were measurable within 3 weeks of tumor cell injection and grew more slowly, with a doubling time of 7 days. These values were calculated from the control group. Mean tumor volumes and body weights at the start of treatment are shown in Table 1 for Task 1 and Table 2 for Task 2.

TABLE 1

MOUSE PARAMETERS AT THE START OF TREATMENT - TASK 1

| Treatment Group | Tumor Volume (mm$^3$ ± SEM*) | Mouse Weight (g ± SEM*) |
|---|---|---|
| PBS (control) MDA MB 231 | 0 | 24.0 ± 0.8 |
| 300 mg/kg | 0 | 24.6 ± 0.9 |
| 1000 mg/kg | 0 | 23.6 ± 07 |

*SEM = Standard error of the mean.

TABLE 2

MOUSE PARAMETERS AT THE START OF TREATMENT - TASK 2

| Treatment Group | Tumor Volume (mm$^3$ ± SEM*) | Mouse Weight (g ± SEM*) |
|---|---|---|
| MDA MB 231 | | |
| Corn oil (control) | 19.1 ± 5.1 | 24.4 ± 0.54 |
| 1000 mg/kg | 24.4 ± 5.8 | 24.5 ± 0.7 |
| 2000 mg/kg | 23.5 ± 5.8 | 23.0 ± 0.8 |
| CTX, 150 mg/kg | 24.0 ± 4.4 | 23.8 ± 0.4 |

*SEM = Standard error of the mean
Tumor Response to Treatment

Pretreatment of mice implanted with MDA MB 231 resulted in prevention of tumor formation in 1/9 mice and regression of one small tumor which grew to a size of 10 mm$^3$ before disappearing. Pretreatment of mice with 1000 mg/kg BP prevented tumor growth in 2/10 animals (20%), and one tumor which grew to a size of 195 mm$^3$ by Day 63 had regressed to 93 mm$^3$ by Day 86, when the study was ended. The mean survival time of animals pretreated with 1000 mg/kg BP was 115 days, compared with 72 days in the control group (p=0.01), if we assume that animals which did not form tumors survived 6 months (180 days).

The MDA MB 231 tumors in Task 2 responded to both treatments. CTX (150 mg/kg) and BP (1000 or 2000 mg) slowed tumor growth substantially, and treatment induced complete regressions with both drugs. Two animals treated with 1000 mg/kg BP showed no reduction in growth rate of the tumors compared with the controls, whereas of the 2 of the tumors regressed completely. Tumors implanted in all three of the animals in the 2000 mg/kg BP treatment group regressed. Treatment was stopped on Day 42, when 2 of the tumors had completely regressed, and one relatively large tumor had started to regress (310 mm$^3$ on Day 31 to 163 mm$^3$ on Day 45). None of the tumors which had completely regressed started to regrow during the 3 month follow-up period, however the tumor which had partially regressed began to regrow after treatment was stopped and had reached a size of 1835 mm$^3$ at the time the experiment was terminated. There was a trend toward increased survival time in animals treated with 2000 mg/kg BP.

Figure 15:
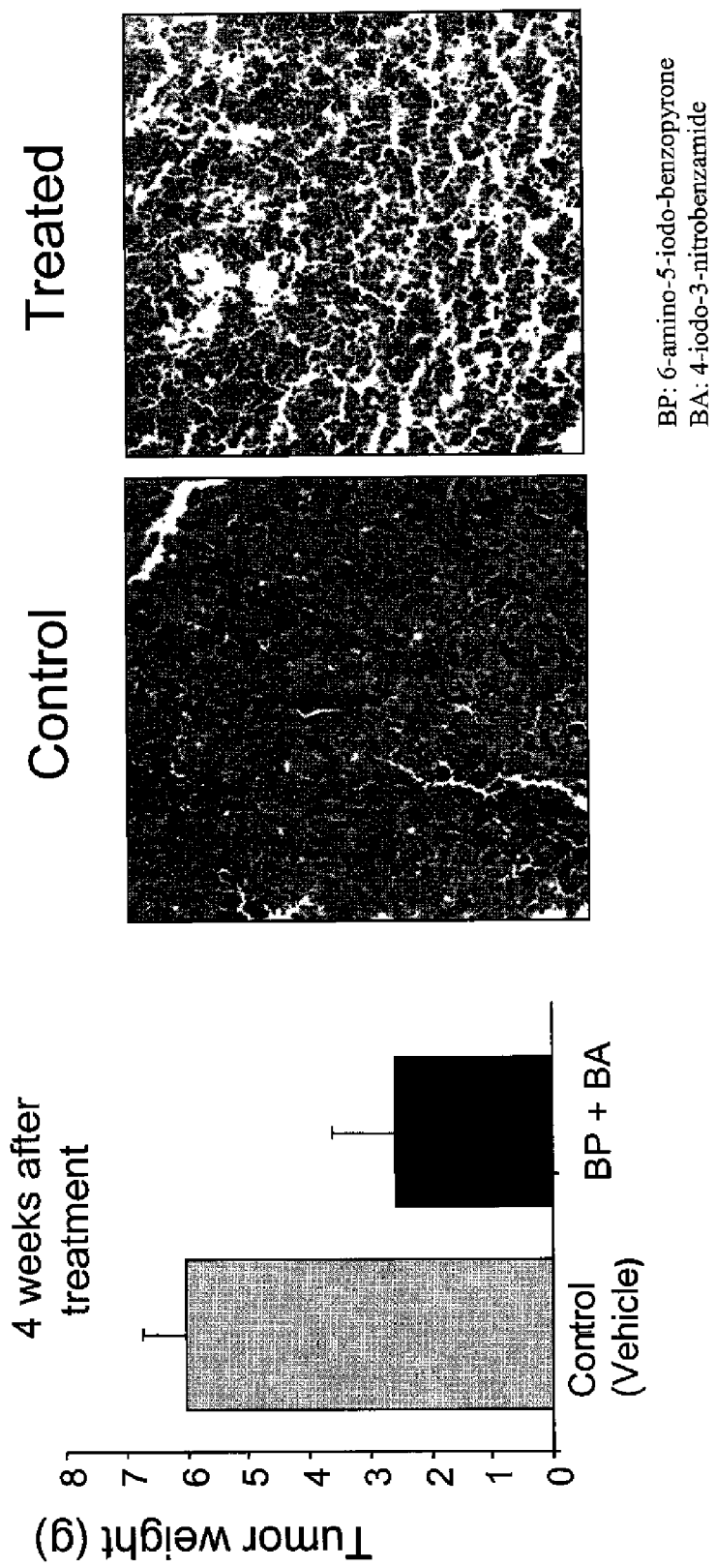
FIG. 15 depicts the effect of 6-amino-5-iodo-2H-1-benzopyran-2-one (BP) in mammary (MDA MB 231) cancer nude mouse xenografts.
Figure 16:
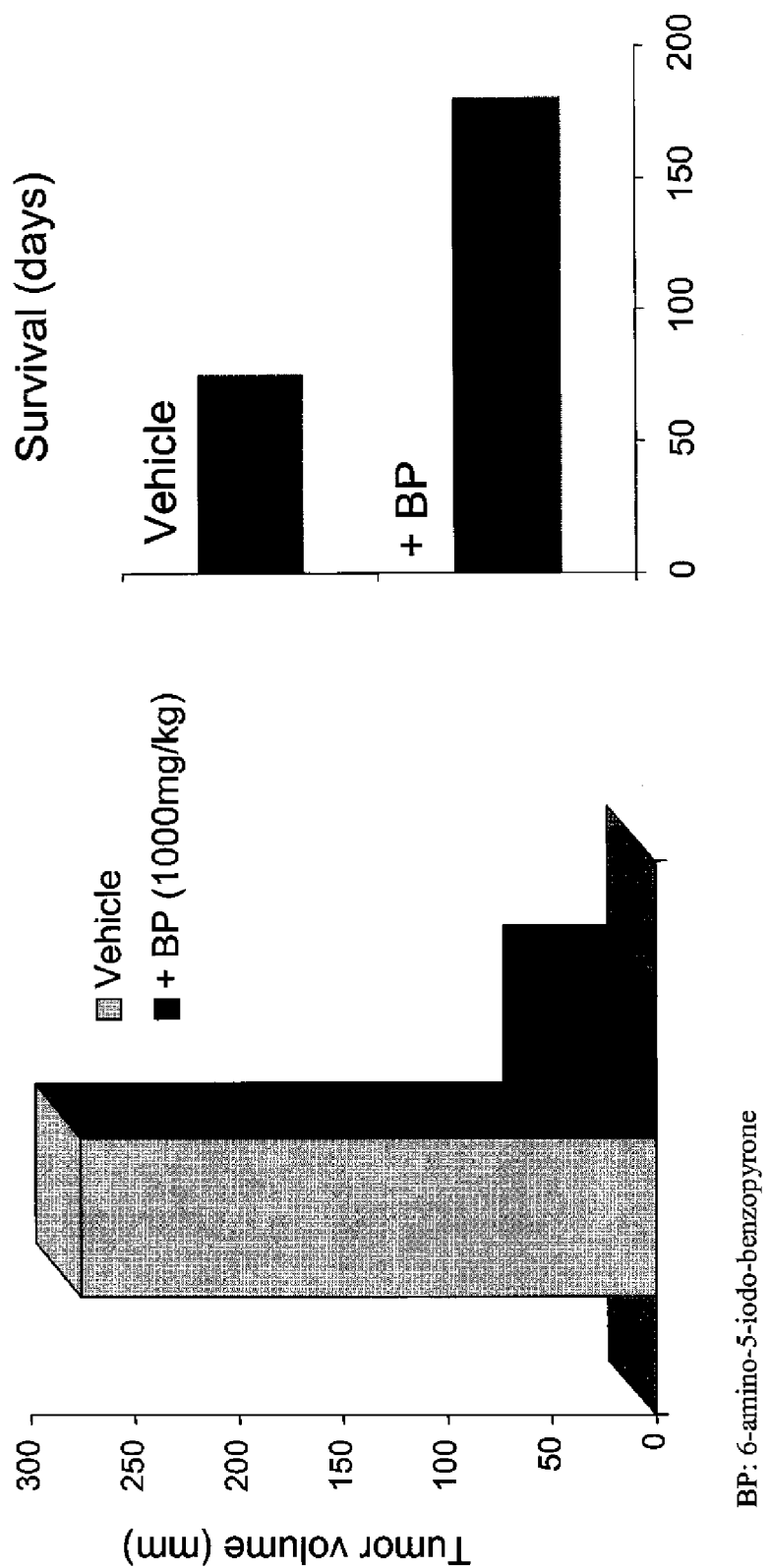
FIG. 16 depicts the effect of 6-amino-5-iodo-2H-1-benzopyran-2-one (BP) and 4-Iodo-3-nitrobenzamide (BA) in mammary (MA MB 231) cancer nude mouse xenografts.

Results of the experiments are shown in FIGS. 15 and 16.

Example 6

Nonclinical Toxicology

The nonclinical toxicology program supporting the oncology application with 4-iodo-3-nitrobenzamide (BA) consisted of acute (single-dose), two-week (multiple-dose), dose-range, and multiple-dose (4-week) toxicology studies conducted in rats and dogs in which BA was administered intravenously. These studies used BA formulated in beta-hydroxypropylcyclodextrin (25%) (Kleptose).

The definitive 4-week studies involved the twice-weekly administration of BA at doses as great as 60 mg/kg/day and included comprehensive clinical evaluations and/or the microscopic assessment of a full list of tissues. The multiple-dose dog study included electrocardiographic measurements and physical examinations including heart rate, respiratory rate, and body temperature evaluations. Toxicokinetic data also was collected in the 4-week multiple-dose rat and dog studies. In addition, two special studies were conducted, an in vitro hemolytic potential/plasma compatibility study with dog and human blood and plasma and an IV local tolerance study in the rabbit. A single-dose investigative study was also conducted in rats to assess the influence of dosing rate upon BA-induced neurobehavioral effects in this model.

BA was well tolerated following single intravenous doses as great as 50 mg/kg in rats and dogs. Following single-bolus intravenous doses of 100 mg/kg, clinical signs, including convulsions in rats and ataxia in dogs, were noted. Repeat doses of 100 mg/kg in dogs caused clinical changes that consisted primarily of excessive salivation and reductions in body weight and food consumption.

Example 7

Title: A Phase 1, first in human, open-label, dose escalation study evaluating the safety and pharmacokinetics of BA in subjects with advanced solid tumors.

Study Phase: 1

Indication: Treatment of advanced solid tumors

Primary Objective: To assess the safety, establish the maximum tolerated dose (MTD) and generate pharmacokinetic profiles of BA after IV administration in adult subjects with histologically documented advanced solid tumors that are refractory to standard therapy or for which no standard therapy is available.

Secondary Objective(s): To evaluate the response in study subjects (per RECIST criteria) with measurable disease. To assess safety profiles: significant laboratory changes and adverse events (AEs) not defined as a dose limiting toxicity (DLT).

Exploratory Objective(s): To assess the effect of treatment on biological markers of tumor status.

Study Design: A phase 1, first in human, open-label, sequential dose escalation study designed to determine safety, MTD and PK profile of BA. BA will be administered intravenously twice weekly (days 1 and 4 of each week) for 3 weeks, followed by a one week BA treatment free period per one 28-day cycle. Cycle one (day 1 thru day 28) will be defined as the safety phase of the study during which the MTD will be determined. The remainder of the study will be termed the maintenance phase. Subjects may participate in this study until a subject experiences a drug intolerance or disease progression.

Safety assessment will follow the guidelines provided in the Cancer Therapy Evaluation Program Common Terminology Criteria for Adverse Events (CTCAE) Version 3.0 dated December, 2003. The first assessment of tumor response, for measurable disease, will be performed during week 8 of the study, and approximately every 8 weeks thereafter. The modified Response Evaluation Criteria in Solid Tumors (RECIST) criteria will be used to establish disease progression. For non-measurable disease, best medical practices will be used to determine time of disease progression Primary Endpoint and Secondary Endpoints: Primary endpoints being safety/tolerability to characterize DLT and PK profiles: BA half life (t½), maximum observed concentration ($C_{max}$), area under the plasma concentration-time curve (AUC), and clearance (CL). Secondary endpoints being tumor response per RECIST criteria; safety profiles: significant laboratory changes and other AEs (not defined as a DLT). Exploratory being reduction in circulating tumor cell (CTC) levels.

Sample Size: As many as 36 subjects are expected to participate in this study. Study subjects will be assigned to sequential cohorts of 1, 3, or 6 subjects at varying dose levels. As many as 10 dose cohorts may be needed to define the MTD.

Summary of Subject Eligibility Criteria:

Inclusion criteria include: (a) ≧18 years old with a pathologically documented, advanced solid tumor that is refractory to standard treatment or for which no standard therapy is available, (b) Eastern Oncology Cooperative Group (ECOG) performance status of ≦2, and (c) absolute neutrophil count (ANC) ≧1.5×109/L (without GCF support within 2 weeks of study day 1); platelet count ≧100.0×109/L (without transfusion within 2 weeks of study day 1); and hemoglobin ≧9.0 g/dL (erythropoietic agents allowed).

Exclusion Criteria include: subject enrolled in another investigational device or drug trial, or is receiving other investigational agents; hematological malignancies; symptomatic or untreated brain metastases requiring concurrent treatment, inclusive of but not limited to surgery, radiation, and corticosteroids; history of seizure disorder; MI within 6 months of study day 1, unstable angina, congestive heart failure (CHF) with New York Heart Association (NYHA) >class II, uncontrolled hypertension; concurrent or prior (within 7 days of study day 1) anticoagulation therapy; specified concomitant medications (see Section 4.2.3); serum creatinine >1.5×ULN; elevated liver enzymes (AST/ALT) >2.5×ULN, or >5.0 if secondary to liver metastases, alkaline phosphatase >2.5×ULN or >5.0 if secondary to liver or bone metastases; total bilirubin >1.5×ULN; systemic chemotherapy within 28 days of study day 1 (42 day washout period for BCNU or mitomycin C); radiation therapy within 28 days of study day 1; antibody therapy for the treatment of an underlying malignancy within 1 month of study day 1, and; concurrent chemotherapy with any agent other than BA or radiation therapy is not permitted throughout the course of the study.

Investigational Product Dosage and Administration: BA will be provided in 10 mL vials of 10 mg/mL concentration. t is estimated that as many as 10 subject cohorts may be necessary to determine the MTD.

Starting Dose (Cohort A): In cohort A, a single subject will receive BA twice weekly at a dose level of 0.5 mg/kg based on weight measured at screening. If this subject experiences a grade 2 toxicity or higher, then 3 additional subjects will be enrolled in this cohort. If no additional subjects dosed in this cohort experience a DLT, then dose escalation will occur as below. If no DLT occurs in the initial subject, dose escalation will occur as below.

Dose Escalation Prior to Grade 2 Toxicity (Potential Cohorts B-J): Until a subject experiences a grade 2 toxicity or higher, one subject will be initially enrolled in all subsequent cohorts at planned 100% dose level increases, with possible cohort expansion as described for cohort A. Safety data will be reviewed after 6 doses of BA, and a decision to escalate to the next cohort will be made if no subject experiences a grade 2 toxicity or higher. If 1 subject in this cohort experiences a grade 2 toxicity or higher, then 3 additional subjects will be enrolled in this cohort. If none of these three additional subjects dosed in this cohort experience a DLT, then further dose escalation will occur. If 1 of 3 subjects experience a DLT, then 3 additional subjects will be enrolled in the same cohort with the same dose. If 0 of these 3 subjects experience a DLT then escalation will occur. If one or more of the additional subjects in a cohort experience a DLT, then the previous lower dose level will be defined as the MTD. Additional subjects may be accrued at the MTD if needed to ensure at least 18 subjects receive BA in the study.

Dose Escalation After Grade 2 Toxicity Level (Potential Cohorts B-J): After the dose associated with the initial grade 2 toxicity is expanded and cleared for dose escalation to the next level, then three subjects will be initially enrolled in all future cohorts (cohorts B, C, D, E, F, G, H, I, or J). If 0 of the 3 initial subjects experience a DLT, then dose escalation to the next cohort will proceed. If 1 of 3 subjects experience a DLT, then 3 additional subjects will be enrolled in the same cohort with the same dose. If 0 of these 3 subjects experience a DLT, then escalation will occur. If one or more of the additional subjects in a cohort experience a DLT, then the previous lower dose level will be defined as the MTD. Additional subjects may be accrued at the MTD if needed to ensure that at least 18 subjects receive BA in the study.

Intra-subject Dose Escalation: Once a BA dose level has been declared safe and tolerable based on the criteria defined above all subjects currently on lower doses may be escalated to the highest safe dose as appropriate (determined by the principal investigator). Once a MTD is determined, all subjects in the study may be escalated as appropriate to receive the MTD.

Overall Dose Escalation Limitations: When a grade 2 toxicity has been observed and that dose level subsequently cleared, individual dose escalations between cohorts will be more conservative, and will be limited to approximately a maximum 40% increase from the previous dose level until a grade 3 toxicity is seen, with subsequent escalations limited to approximately 25% dose increases. Absolute dose escalation will be decided by the safety review group after review of all available data.

Control Group: None

Procedures:

Screening: Pre-enrollment screening tests and evaluation will be performed only after a signed, written Institutional Review Board (IRB) approved informed consent is obtained from each subject. Procedures will be performed within 2 weeks of study day 1 unless otherwise noted. Clinical evaluation includes complete history, physical examination, ECOG status, height, weight, vital signs, and documentation of concomitant medications. Laboratory studies include hematology (with differential, reticulocyte count, and platelets); prothrombin time (PT) and partial thromboplastin time (PTT); comprehensive chemistry panel (sodium, potassium, chloride, CO2, creatinine, calcium, phosphorous, magnesium, BUN, uric acid, albumin, AST, ALT, alkaline phosphatase, total bilirubin, and cholesterol, HDL, and LDL), urinalysis with microscopic examination, serum tumor markers, serum or urine pregnancy test for women of child bearing potential. Cardiac studies include creatine kinase (CK), and 12-lead electrocardiogram (EKG). Clinical staging includes imaging for measurable disease by computed tomography (CT) or magnetic resonance (MRI) within 4 weeks of study day 1. Documentation of clinical staging for non-measurable disease will occur.

Treatment: Eligible subjects will be enrolled into the study and receive study drug on Day 1. Pre-dose and post-dose tests will be performed as outlined in the study protocol. Dosing of BA will occur twice weekly at days 1, 4, 8, 11, 15, and 18 of each 28 day cycle; and administered over an infusion period as long as 2 hours. On day 29, subjects will start cycle 2 and resume dosing at days 1, 4, 8, 11, 15, and 18 of that and each subsequent cycle. Subjects may participate in this study until they experience a drug intolerance or disease progression or withdraw consent. Subjects meeting the modified RECIST criteria of disease progression may continue in the study if they are demonstrating clinical benefit.

The first scheduled tumor response measurement for measurable disease will be performed during week 8 (study day 50±5 days) of the study, and every 8 weeks thereafter. Tumor response according to the modified Response Evaluation Criteria in Solid Tumors (RECIST) criteria will be used to establish disease progression by CT or MRI (the same technique used during screening must be used). For non-measurable disease, best medical practices will be used to determine time of disease progression.

End of Study: All subjects should have the end of study procedures as described in the protocol completed no more than 30 days after the last dose of BA. Additionally, subjects will have overall tumor response assessed via clinical imaging if not done within 30 days prior to the last dose of BA.

Statistical Considerations: Descriptive statistics will be calculated for safety, PK, and PD endpoints. Response data, to establish time to progression, will be reported descriptively in the form of listings. Tumor progression data will be categorized using the modified RECIST criteria.

PK parameters will be estimated using non-compartmental methods. PK parameters will be summarized by the arithmetic mean, standard deviation, coefficient of variation, maximum, minimum, median, and geometric mean. Summary statistics will be calculated with SPlus version 5.1 (or later).

If appropriate, data may also be analyzed by a non-linear mixed-effects modeling approach (population approach) to compartmental analysis. Other analyses will be done descriptively as appropriate.

Results will be analyzed after all subjects have received at least one cycle (6 doses) of BA at the MTD dose level (or their highest dose level received in the study). This will coincide with the completion of the safety phase of the study. Additional analyses will be performed on an ongoing basis as necessary to provide information for design of future trials.

The above examples are in no way intended to limit the scope of the instant invention. Further, it can be appreciated to one of ordinary skill in the art that many changes and modifications can be made thereto without departing from the spirit or scope of the appended claims, and such changes and modifications are contemplated within the scope of the instant invention.

It will be apparent to one of ordinary skill in the art that many changes and modifications can be made thereto without departing from the spirit or scope of the appended claims.

The invention claimed is:

1. A method of treating a cancer comprising administering to a subject in need thereof an effective amount of a composition comprising a compound of formula (Ia)

wherein $R_1$, $R_2$, $R_3$, $R_4$, and $R_5$ are, independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, or a pharmaceutically acceptable salt or solvate, thereof,
wherein said cancer is bone cancer, and wherein said bone cancer is not a bone metastasis cancer or leukemia originating in bone marrow.

2. The method of claim 1 further comprising surgery, radiation therapy, chemotherapy, gene therapy, immunotherapy, or a combination thereof.

3. The method of claim 1 further comprising administering an effective amount of buthionine sulfoximine.

4. The method of claim 1 wherein a bone cancer cell undergoes apoptosis, cell cycle arrest, and/or necrosis in a patient.

5. The method of claim 1 further comprising administering an effective amount of a benzopyrone compound of formula (II):

wherein $R_1$, $R_2$, $R_3$ and $R_4$ are independently selected from the group consisting of H, halogen, optionally substituted hydroxy, optionally substituted amine, optionally substituted lower alkyl, optionally substituted phenyl and optionally substituted $C_3$-$C_8$ cycloalkyl or a salt thereof.

6. The method of claim 5, wherein the compound of formula II is 5-iodo-6-aminobenzopyrone:

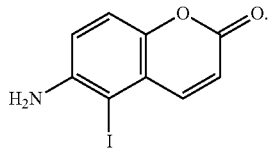 [SMILES: Nc1ccc2oc(=O)ccc2c1I]

7. The method of claim 1, wherein said compound of formula (Ia) is

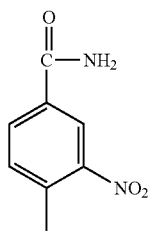

or a pharmaceutically acceptable salt thereof.

8. The method of claim 1, wherein the bone cancer is from the Ewing's family of tumors.

9. The method of claim 1, wherein the bone cancer is an osteosarcoma.

* * * * *

UNITED STATES PATENT AND TRADEMARK OFFICE
CERTIFICATE OF CORRECTION

| | |
|---|---|
| PATENT NO. | : 8,377,985 B2 |
| APPLICATION NO. | : 12/165437 |
| DATED | : February 19, 2013 |
| INVENTOR(S) | : Kun et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 254 days.

Signed and Sealed this
Eighth Day of October, 2013

Teresa Stanek Rea
*Deputy Director of the United States Patent and Trademark Office*

Disclaimer

8,377,985 B2 — Ernest Kun, Mill Valley, CA (US); Jerome Mendeleyev, San Francisco, CA (US); Carol Basbaum, San Francisco, CA (US); Hassan Lemjabbar-Alaoui, Danville, CA (US); Valeria S. Ossovskaya, San Francisco, CA (US), TREATMENT OF CANCER. Patented date February 19, 2013. Disclaimer filed December 19, 2013 by the Assignee, BiPar Sciences, Inc.

Hereby enter this disclaimer for the entire term of said patent.

*(Official Gazette, April 1, 2014)*